US005891991A

United States Patent [19]

Wasco et al.

[11] Patent Number: 5,891,991

[45] Date of Patent: Apr. 6, 1999

[54] AMYLOID PRECURSOR-LIKE PROTEIN AND USES THEREOF

[75] Inventors: Wilma Wasco, Boston, Mass.; Keith Bupp, Chalfont, Pa.; Margaret Magendantz, Summerville, Mass.; Rudolph Tanzi, Canton, Mass.; Frank Solomon, Cambridge, Mass.

[73] Assignees: The General Hospital Corporation, Boston; The Massachusetts Institute of Technology, Cambridge, both of Mass.

[21] Appl. No.: 689,276

[22] Filed: Aug. 6, 1996

Related U.S. Application Data

[60] Division of Ser. No. 7,999, Jan. 21, 1993, which is a continuation-in-part of Ser. No. 930,022, Aug. 17, 1992, abandoned, which is a continuation-in-part of Ser. No. 872,642, Apr. 20, 1992, abandoned.

[51] Int. Cl.$^6$ .................... A61K 38/00

[52] U.S. Cl. .................... 530/300; 530/350; 530/810; 424/184.1; 424/185.1; 424/193.1

[58] Field of Search .................... 530/350, 300, 530/810; 424/184.1, 185.1, 193.1

[56] References Cited

U.S. PATENT DOCUMENTS

| | | |
|---|---|---|
| 4,376,110 | 3/1983 | David et al. . |
| 4,579,821 | 4/1986 | Palmiter et al. . |
| 4,666,829 | 5/1987 | Glenner et al. . |
| 4,728,605 | 3/1988 | Fudenberg et al. . |
| 4,912,206 | 3/1990 | Goldgaber et al. . |
| 5,221,607 | 6/1993 | Cordell et al. . |
| 5,441,931 | 8/1995 | Sprecher et al. . |

FOREIGN PATENT DOCUMENTS

| | | |
|---|---|---|
| 0 125 023 | 11/1984 | European Pat. Off. . |
| 0 171 496 | 2/1986 | European Pat. Off. . |
| 0 173 494 | 3/1986 | European Pat. Off. . |
| 0 184 187 | 6/1986 | European Pat. Off. . |
| WO 86/01533 | 3/1986 | WIPO . |
| WO 87/02671 | 5/1987 | WIPO . |
| WO 88/03951 | 6/1988 | WIPO . |
| WO 90/14840 | 12/1990 | WIPO . |
| 9615265 | 10/1994 | WIPO . |

OTHER PUBLICATIONS

Abe, K. et al., "Induction of amyloid precursor protein mRNA after heat shock in cultured human lymphoblastoid cells," *Neurosci. Lett. 125*(*2*):169–171 (Apr. 1991).

Abe, K. et al., "Selective induction of Kunitz–type protease inhibitor domain–containing amyloid precursor protein mRNA after persistent focal ischemia rat cerebral cortex," *Neurosci. Lett. 125*(*2*):172–174 (Apr. 1991).

Anonymous, "At last, animal models for studying Alzheimer's: A tale of four mice," *Biotech. Newswatch 11*(*15*):1,4 (Aug. 1991).

Bradley, J. E. et al., "A Simple, Rapid Method for the Purification of Poly A$^+$ RNA," *Biotechniques 6*(*2*):114–116 (1988).

Beidler, C. B. et al., "Cloning and High Level Expression of a Chimeric Antibody with Specificity for Human Carcinoembryonic Antigen," *J. Immunol. 141:*4053–4060 (1988).

Beltz, G. A. et al., "Isolation of Multigene Families and Determination of Homologies by Filter Hybridization Methods," *Meth. Enzymol. 100:*266–285 (1983).

Benes, F. M. et al., "Structural Diversity and Infrastructure of Amyloid Deposits in Alzheimer Brain," *Soc. Neurosci. 13:*1153, Abstr. No. 316.15 (1987).

Benoist, C. and P. Chambon, "In vivo sequence requirements of the SV40 early promoter region," *Nature 290:*304–310 (1981).

Better, M. et al., "*Escherichia coli* Secretion of an Active Chimeric Antibody Fragment," *Science 240:*1041–1043 (1988).

Birghauer E. and F. Solomon, "A Marginal Band–associated Protein Has Properties of Both Microtubule–and Microfilament–associated Proteins," *J. Cell. Biol. 109:*1609–1620 (1989).

Blobel, G., "Intracellular protein topogenesis," *Proc. Natl. Acad. Sci. USA 77*(*3*):1496–1500 (1980).

Bollon, A. P. and M. Stauver, "DNA Transformation Efficiency of Various Bacterial and Yeast Host–Vector Systems" *J. Clin. Hematol. Oncol. 10*(*2 & 3*): 39–48 (1980).

Botstein, D. et al., "Making Mutations In vitro and Putting Them Back Into Yeast," in: *From Gene to Protein: Translation Into Biotechnology,* Ahmad, F. et al., eds., Academic Press, Inc.: New York pp. 265–274 (1982).

Brandis, J. et al., "Preparation of cDNA Libraries and the Detection of Specific Gene Sequences," in: *Genetic Engineering,* Setlow, J. K. et al., eds., Plenum Press: New York, pp. 299–316 (1986).

Broach, J. R., "The Yeast Plasmid 2$\mu$ Circle," *Cell 28:* 203–204 (1982).

Broach, J. R., "The Yeast Plasmid 2$\mu$ Circle," in: *The Molecular Biology of the Yeast Saccharomyces: Life Cycle and Inheritance,* Strathern, J. N. et al., eds., Cold Spring Harbor Laboratory Press: Cold Spring Harbor, NY, pp. 445–470 (1981).

(List continued on next page.)

*Primary Examiner*—Paula K. Hutzell
*Assistant Examiner*—Heather A. Bakalyar
*Attorney, Agent, or Firm*—Sterne, Kessler, Goldstein & Fox P.L.L.C.

[57] ABSTRACT

The present invention is directed to isolated amyloid precursor-like proteins (APLPs), nucleotide sequences coding for and regulating expression of these protein, antibodies directed against these proteins, and recombinant vectors and host cells containing the genetic sequences coding for and regulating the expression of these protein sequences. The invention is also directed to isolated genomic. DNA, cDNA anti-sense RNA, and RNA containing the protein sequence. Antibodies can be used to detect an APLP in biological specimens, including, for example, fluid, serum or tissue samples. APLP1 and APLP2 are candidate genes for late onset familial Alzheimer's disease.

5 Claims, 21 Drawing Sheets

OTHER PUBLICATIONS

Brook, J. D. et al., "The physical map of chromosome arm 19q: some new assignments, confirmations and re–assessments," *Hum. Genet. 87*(*1*): 65–72 (May. 1991).

Bush, A. I. et al., "Specific and Saturable Binding of the Amyloid Protein Precursor of Alzheimer's disease by Zinc(II)," *Neurobiol. Aging 13* (*Suppl 1*):S84 Abstr. No. A. 331 (Jul. 1992).

Buxbaum, J. D. et al., "Processing of Alzheimer β/A4 amyloid precursor protein: Modulation by agents that regulate protein phosphorylation," *Proc. Natl. Acad. Sci. USA 87*:6003–6006 (1990).

Chartier–Harlin, M.–C. et al., "Early–onset Alzheimer's disease caused by mutations at condon 717 of the β–amyloid precursor protein gene," *Nature 353:*844–846 (Oct. 1991).

Chen, W.–J et al., "NPXY, a Sequence Often Found in Cytoplasmic Tails, Is Required for Coated Pit–mediated Internalization of the Low Density Lipoprotein Receptor," *J. Biol. Chem. 256(6):*3116–3123 (1990).

Cheng, S. V. et al., "Comparative mapping of DNA markers from the familial Azheimer disease and Down syndrome regions of human chromosome 21 to mouse chromosmes 16 and 17," *Proc. Natl. Acad. Sci. USA 85:*6032–6036 (1988).

Church, G. M. and W. Gilbert, "Genomic sequencing," *Proc. Natl. Acad. Sci. USA 81:*1991–1995 (1984).

Church, G. M. and W. Gilbert, "The Genomic Sequencing Technique," in: *Medical Genetics: Past. Present. Future*, Alan R. Liss, Inc.: New York, pp. 17–21 (1985).

Cullen, B. R., "Use of Eukaryotic Technology in the Functional Analysis of Cloned Genes," *Meth. Enzymol. 152:*684–704 (1987).

Deen, K. C. et al., "Use of T4 DNA Polymerase Replacement Synthesis for Specific Labeling of Plasmid–Cloned Inserts,"*Analytical Biochem. 135:*456–465 (1983).

De Sauvage, F. and J.–N. Octave, "A Novel mRNA of the A4 Amyloid Precursor Gene Coding for a Possible Secreted Protein," *Science 245* :651–653 (1989).

Donaldson, J. G. et al., "Dissociation of a 110–kD Peripheral Membrane Protein from the Golgi Apparatus Is an Early Event in Brefeldin A Action," *J. Cell Biol. 111*(*6*):2295–2306 (1990).

Esch, F. S. et al., "Cleavage of Amyloid β Peptide During Constitutive Processing of Its Precursor," *Science 248*: 1122–1124 (1990).

Estus, S. et al., "Potentially Amyloidogenic, Carboxyl–Terminal Derivatives of the Amyloid Protein Precursor," *Science 255* :726–728 (Feb. 1992).

Fabrice, D. et al., "A new TaqI polymorphism detected by the cDNA encoding amyloid beta protein of Alzheimer's disease," *Chem. Abstr. 108*:154, Absr. No. 17130p (1988).

Feinberg, A. P. and B. Vogelstein, "A Technique for Radiolabeling DNA Restriction Endonuclease Fragments to High Specific Activity," *Analytical Biochem. 132* :6–13 (1983).

Fidani, L. et al., "Screening for mutations in the open reading frame and promotor of the β–amyloid precursor protein gene in familial Alzheimer's disease: identification of a Further family with APP717 Val→Ile," *Human Mol. Genet. 1*(*3*):165–168 (Jun. 1992).

Frohman, M. A. et al., "Rapid production of full–length cDNAs from rare transcripts: Amplification using a single gene–specific oligonucleotide primer," *Proc. Natl. Acad. Sci. USA 85*:8998–9002 (1988).

Gamzu, E., "Animal Behavioral Models in the Discovery of Compounds to Treat Memory Dysfunction," *Ann. New York Acad. Sci. 444*:370–393 (1985).

Gandy, S. et al., "Phosphorylaton of Alzheimer disease amyloid precursor peptide by protein kinase C and $Ca^{2+}$/calmodul in–dependent protein kinase II," *Proc. Natl. Acad. Sci. USA 85*:6218–6221 (1988).

Geissler, E. N. et al., "Stem Cell Factor (SCF), a Novel Hematopoietic Growth Factor and Ligand for c–kit Tyrosine Kinase Receptor, Maps on Human Chromosome 12 between 12q14.3 and 12qter," *Somatic Cell Mol. Genet. 17*(*2*):207–214 (Jan. 1991).

Glenner, G. G. and C. W. Wong, "Alzheimer's Disease: Initial Report of the Purification and Characterization of a Novel Cerebrovascular Amyloid Protein," *Biochem. Biophys. Res. Comm. 120*(*2*):885–890 (1984).

Goate, A. et al., "Segregation of a Missense mutation in the amyloid precursor protein gene with familial Alzheimer's disease," *Nature 349* :704–706 (Feb. 1991).

Goedert, M., "Neuronal localization of amyloid beta protein precursor mRNA in normal human brain and in Alzheimer's disease," *EMBO J. 6*(*12*):3627–3632 (1987).

Golde, T. E. et al., "Processing of the Amyloid Protein Precursor to Potentially Amyloidogenic Derivatives," *Science 255*:728–730 (Feb. 1992).

Goldgaber, D. et al., "Characterization and Chromosomal Localization of a cDNA Encoding Brain Amyloid of Alzheimer's Disease," *Science 235*:877–880 (1987).

Graw, S. et al., "Irradiation–Reduced Human Chromosome 21 Hybrids," *Somatic Cell Mol. Genet. 14*(*3*):233–242 (1988).

Gusella, J. F. et al., "DNA Markers for Nervous System Diseases," *Science 255*:1320–1326 (1984).

Gusella, J. F. et al., "Genetic Linkage Map for Chromosome 21," *Ann. New York Acad. Sci. 450*:25–31 (1985).

Haass, C. et al., "Targeting of cell–surface β–amyloid precursor protein to lysosomes: alternative processing into amyloid–bearing fragments," *Nature 357*:500–503 (Jun. 1992).

Haass, C. et al., "Amyloid β–peptide is produced by cultured cells during normal metabolism," *Nature 359*:322–325 (Sep. 1992).

Haines, J. L. et al., "Chromosome 21 genetic linkage data set based on the Venezuelan reference pedigree," *Cytogenet. Cell Genet. 59*(*2–3*):88–89 (February 1992).

Hamer, D. H. and M. Walling, "Regulation In Vivo of a Cloned Mammalian Gene: Cadmium Induces the Transcription of a Mouse Metallothionein Gene in SV40 Vectors," *J. Mol. Applied Genet. 1*:273–288 (1982).

Hammerling, G. J. et al., eds., in: *Monoclonal Antibodies and T–Cell Hybridomas: Perspectives and Technical Advances,* Elsevier: New York, pp. 565–587 (1981).

Hyman, B. T. et al., "Kunitz Protease Inhibitor–Containing Amyloid β Protein Precursor Immunoreactivity in Alzheimer's Disease," *J. Neuropathtol. Exp. Neurol. 51*(*1*):76–83 (Jan. 1992).

Hyman, B. T. et al., "Nonisotopic in situ hybridization of amyloid beta protein precursor in Alzheimer's disease: expression in neurofibrillary tangle bearing neurons and in the microenvironment surrounding senile plaques," *Mol. Brain Res. 18*(*3*):253–258 (May 1993).

Hyman, B. and R. E. Tanzi, "Amyloid dementia and Alzheimer's disease," *Current Opinion in Neurol. Neurosurgery 5*(*1*):88–93 (Feb. 1992).

Ishii, T. et al., "The Immunohistochemical Demonstration of Subsequences of the Precursor of the Amyloid A4 Protein in Senile Plaques in Alzheimer's Disease," *Neuropathol. Appl. Neurobiol. 15:*135–147 (1989).

Jacobsen, J. S. et al., "A Novel Species–Specific RNA Related to Alternatively Spliced Amyloid Precursor Protein mRNAs," *Neurobiol. Aging 12*(*5*):575–583 (Sep. /Oct. 1991).

Johnston, S. A. and J. E. Hopper, "Isolation of the yeast regulatory gene *GAL4* and analysis of its dosage effects on the galactose/melibiose regulon," *Proc. Natl. Acad. Sci. USA 79* :6971–6975 (1982).

Jones, P. T. et al., "Replacing the complementarity–determining regions in a human antibody with those from a mouse,"*Nature 321*:522–525 (1986).

Kang, J. et al., "The precursor of Alzheimer's disease amyloid A4 protein resembles a cell–surface receptor," *Nature 325*: 733–736 (1987).

Kawabata, S. et al., "Alzheimers's retraction," *Nature 356*:23 (Mar. 1992).

Kawabata, S. et al., "Amyloid plaques, neurofibrillary tangles and neuronal loss in brains of transgenic mice overexpressing a C–terminal fragment of human amyloid precursor protein," *Nature 354*:476–478 (Dec. 1991).

Kitaguchi, N. et al., "Novel precursor of Alzheimer's disease amyloid protein shows protease inhibitory activity," *Nature 331*:530–532 (1988).

Kittur, S.D. et al., "A linkage map of three anonymous human DNA fragments and SOD–1 on chromosome 21," *EMBO J. 4*(*9*):2257–2260 (1985).

Köhler, G. and Milstien, "Continous culture of fused cells secreting antibody of predefined specificity," *Nature 256*:495–497 (1975).

Köhler, G. et al., "Fusion between immunoglobulin–secreting myeloma cell lines," *Eur. J. Immunol. 6*:292–295 (1976).

Köhler, G. and C. Milstein, "Derivation of specific antibody–producing tissue culture and tumors lines by cell fusion," *Eur. J. Immunol. 6*:511–519 (1976).

König, G. et al., "Identification and Differential Expression of a Novel Alternative Splice Isoform of the βA4 Amyloid Precursor Protein (APP) mRNA in Leukocytes and Brain Microglial Cells," *J. Biol. Chem. 267*(*15*):10804–10809 (May 1992).

Kozak, M., "Compilation and analysis of sequences upstream from the translational start site in eukaryotic mRNAs," *Nucl. Acids Res. 12*(*2*):857–872 (1984).

Lal, H. and M. J. Foster, "Congnitive Disorders Related to Immune Dysfunction: Novel Animal Models for Drug Development," *Drug Develop. Res. 7*:195–208 (1986).

Lathe, R., "Synthetic Oligonucleotide Probes Deduced from Amino Acid Sequence Data: Theoretical and Pratical Considerations," *J. Mol. Biol. 183*:1–12 (1985).

Leary, J. J. et al., "Rapid an sensitive colorimetric method for visualizing biotin–labeled DNA probes hybridized to DNA or RNA immobilized on nitrocellulose: Bio–blots," *Proc. Natl. Acad. Sci. USA 80*:4045–4049 (1983).

Lendahl, U. et al., "CNS Stem Cells Express a New Class of Intermediate Filament Protein," *Cell 60*:585–595 (1990).

Lichtenstein, C., "Antisense RNA as a tool to study plant gene expression," *Nature 333*:801–802 (1988).

Liu, A. Y. et al., "Chimeric mouse–human IgG1 antibody that can mediate lysis of cancer cells," *Proc. Natl. Acad. Sci. USA 84*:3439–34443 (1987).

Liu, A. Y. et al., "Production of a Mouse–Human Chimeric Monoclonal Antibody to CD20 with Potent Fc–Dependent Biologic Activity," *J. Immunol. 139*(*10*):3521–3526 (1987).

Luo, L et al., "Human Amyloid Precursor Protein Ameliorates Behavioral Deficit of Flies Deleted for Appl Gene," *Neuron 9*:595–605 (Oct. 1992).

Luo, L. et al., "Identification, Secretion, and Neural Expression of APPL, a Drosophila Protein Similar to Human Amyloid Protein Precursor," *J. Neurosci. 10*(*12*):3849–3861 (1990).

Magendantz, M. and F. Solomon, "Analyzing the components of microtubules: Antibodies against chartins, associated proteins from cultured cells," *Proc. Natl. Acad. Sci. USA 82*:6581–6585 (1985).

Majocha, R. E. et al., "Laminar–specific distribution and infrastructural detail of amyloid in the Alzheimer disease cortex visualized by computer–enhanced imaging of epitopes recognized by monoclaonal antibodies," *Proc. Natl. Acad. USA 85*:6182–6186 (1988).

Maniatis, T., "Recombinant DNA Procedures in the Study of Eukaryotic Genes," *Cell Biol. 3*:563–608 (1980).

Marcantonio, E. E. and R. O. Hynes, "Antibodies to the Conserved Cytoplasmic Domain of the Integrin $\beta_1$ Subunit React with Proteins in Vertebrates, Invertebrates, and Fungi," *J. Cell. Biol. 106*:1765–1772 (1988).

Marotta, C. A. et al., "In vitro Synthesis of Human Brain Proteins Including Tubulin and Actin by Purified Postmortem Polysomes," *J. Neurochem. 36*(*3*):966–975 (1981).

Marotta C. A. et al., "Transcriptional and translational regulatory mechanisms during normal aging of the mammalian brain and in Alzheimer's disease," in: *Progress in Brain Research,* Swaab, D. F. et al., eds., Elsevier Science Publishers B. V.: New York, pp. 303–320 (1986).

Marx, J., "Major Setback for Alzheimer's Models," *Science 255*:200–1202 (Mar. 1992).

Masters, C. L. et al., "Neuronal origin of a cerebral amyloid: Neurofibrillary tangles of Alzheimer's disease contain the same protein as the amyloid of plaque cores and blood vessels," *EMBO J. 4*(*11*):2757–2763 (1985).

Masters, C. L. et al., "Amyloid plaque core protein in Alzheimer disease and Down syndrome," *Proc. Natl. Acad. Sci. USA 82*:4245–4249 (1985).

McKnight, S. L. "Functional Relationships between Transcriptional Control Signals of the Thymidine Kinase Gene of Herpes Simplex Virus," *Cell 31*:355–365 (1982).

Moreman, K.W. and O. Touster, "Biosynthesis an Modification of Golgi Mannosidase II in HeLa and 3T3 Cells," *J. Biol. Chem. 260*(*11*) 6654–6692 (1985).

Morrison, S. L., "Transfectomas Provide Novel Chimeric Antibodies,"*Science 229*:1202–1207 (1985).

Mullan, M. et el., "A locus for familial early–onset Alzheimer's disease on the long arm of chromosome 14, proximal to the α1–antichymotrypsin gene," *Nature Genetics 2*:340–342 (Dec. 1992).

Murrel, J. et al., "A Mutation in the Amyloid Precursor Protein Associated with Hereditary Alzheimer's Disease," *Science 254*:97–99 (Oct. 1991).

Nishimura, Y. et al., "Recombinan Human–Mouse Chimeric Monoclonal Antibody Specific for Common Acute Lymphocytic Leukemia Antigen," *Cancer Res. 47*:999–1005 (1987).

Ohara, O et al., "One–sided polymerase chain reaction: The amplification of cDNA," *Proc. Natl. Acad. Sci. USA 86*:5673–5677 (1989).

Oi, V. T. and S. L. Morrison, "Chimeric Antibodies," *BioTechniques 4*(*3*):214–221 (1986).

Oltersdorf, T. et al., "The Alzheimer Amyloid Precursor Protein: Identification of a Stable Intermediate in the Biosynthetic/Degradative Pathway," *J. Biol. Chem. 265* (*8*):4492–4497 (1990).

Palacios, G. et al., "β–Amyloid precursor protein localization in the Golgi apparatus in neurons and oligodendrocytes. An immunocytochemical structural and ultrastructal study in normal and axotomized neurons," *Mol. Brain Res. 15*(*3–4*): 195–206 (Oct. 1992).

Palmert, M. R. et al., "Amyloid Protein Precursor Messenger RNAs: Different Expression in Alzheimer's Disease," *Science 241*:1080–1084 (1988).

Palmert, M. R. et al., "The β Amyloid Protein Precusor: mRNAs, Membrane–Associated Forms, and Soluble derivatives," in: *Alzheimer's Disease and Related Disorders,* Iqbal, K. et al., eds., Alan R. Liss: New York, pp. 971–984 (1989).

Palmert, M. R. et al., "The β–amyloid protein precursor of Alzheimer disease has soluble derivatives found in human brain and cerebrospinal fluid," *Proc. Natl. Acad. Sci. USA 86*:6338–6342 (1989).

Palmert, M. R. et al., "Analysis of the β–Amyloid Protein Precursor of Alzheimer's Disease: mRNAs and Protein Products," in: *Advances in Neurology, vol. 51: Alzheimer's Disease,* Wurtman, R. J. et al., eds. Raven Press, Ltd.: New York, pp. 181–184 (1990).

Palmiter, R. D. et al., "Dramatic growth of mice that develop from eggs microinjected with metallothionein–growth hormone fusion genes," *Nature 300*:611–615 (1982).

Pardridge, W. M. et al., "High Molecular Weight Alzheimer's Disease Amyloid Peptide Immunoreactivity in Human Serum and CSF is an Immunoglobulin G," *Biochem. Biophys. Res. Comm. 145*(*1*):241–248 (1987).

Patterson, D. et al., "Mapping of the gene encoding the β–amyloid precursor protein and its relationship to the Down syndrome region of chromosome 21," *Proc. Natl. Acad. Sci. USA 85*:8266–8270 (1988).

Pelletier, J. et al., "Assignment of Two of the Translation Initiation Factor–4E (EIF4EL1 and EIF4EL2) Genes to Human Chromosomes 4 and 20," *Genomics 10*(*4*):1079–1082 (Aug. 1991).

Pericak–Vance, M. A. et al., "Linkage Studies in Familial Alzheimer Disease: Evidence for Chromosome 19 Linkage," *Am. J. Hum. Genet. 48*(*6*):1034–1050 (Jun. 1991).

Perkins, A. S. et al., "Design of a Retrovirus–Derived Vector for Expression and Transduction of Exogenous Genes in Mammalian Cells," *Mol. Cell. Biol. 3*(*6*):1123–1132 (1983).

Phelan, M. C. et al., "Molecular and Ctyogenetic Characterization of a De Novo t(5p;21q) in a Patient Previously Diagnosed as Monosomy 21," *Am. J. Hum. Genet. 43*:511–519 (1988).

Ponte, P. et al., "A new A4 amyloid mRNA contains a domain homologous to serine proteinase inhibitors," *Nature 331* :525–527 (1988).

Renz, M., "Polynuleotide–histone H1 complexes as probes for blot hybridization," *EMBO J. 2*(*6*):817–822 (1983).

Renz, M. and C. Kurz, "A colorimetric method for DNA hybridization," *Nucl. Acids Res. 12*(*8*):3435–3444 (1984).

Rigby, P. W. J. et al., "Labeling Deoxyribonucleic Acid to High Specific Activity in Vitro by Nick Translation with DNA Polymerase I," *J. Mol. Biol. 133*:237–251 (1977).

Robakis, N. K. et al., "Molecular cloning an characterization of a cDNA encoding the cerebrovascular and the neuritic plaque amyloid plaques," *Proc. Natl. Acad Sci USA 84*:4190–4194 (1987).

Rosen, D. R. "A Drosophila gene encoding a protein resembling the human β–amyloid protein precursor," *Proc. Natl. Acad. Sci. 86*:2478–2482 (1989).

Sacchi, N. et al., "The ETS Genes on Chromosome 21 Are Distal to the Breakpoint of the Acute Myelogenous Leukemia Translocation (8;21)," *Genomics 3*:110–116 (1988).

St. George–Hyslop. P. H. et al., "The Genetic Defect Causing Familial Alzheimer's Disease Maps on Chromosome 21," *Science 235*:885–890 (1987).

St. George–Hyslop, P. H. et al., "Absence of Duplication of Chromosome 21 Genes in Familial and Sporadic Alzheimer's Disease," *Science 238*:664–666 (1987).

St. George–Hyslop. P. et al., "Search for the Familial Alzheimer's Disease gene," *J. Neural Transm.* [*Suppl* ]*24*:13–21 (1987).

St. George–Hyslop, P.H. et al., "Familial Alzheimer's Disease: Progress and Problems," *Neurobiol. Aging 10*: 417–425 (1989).

St. George–Hyslop. P. H. et al., "Molecular Genetics of Familial Alzheimer's Disease," *Eur. Neurol. 29*(*suppl. 3*):25–27 (1989).

St. George–Hyslop, P. H. et al., "Genetic linkage studies suggest that Alzheimer's disease is not a single homogeneous disorder," *Nature 347*:194–197 (1990).

St. George–Hyslop, P. et al., "Genetic evidence for a novel familial Alzheimer's disease locus on chromosome 14," *Nature Genetics 2*:330–334 (Dec. 1992).

Saitoh, T. et al., "Secreted Form of Amyloid β Protein Precursor Is Involved in the Growth Regulation of Fibroblasts," *Cell 58*:615–622 (1989).

Sajdel–Sulkowska, E. et al., "In Vitro Synthesis of Polypeptides of Moderately Large Size by Poly(A)–Containing Messenger RNA from Postmortem Human Brain and Mouse Brain," *J. Neuochem. 40*(*3*):670–680 (1983).

Sajdel–Sulkowska, E. M. et al., "Genetic Expression of Amyloid and Glial–specific Protein in the Alzheimer Brain," *JAGS 36*:558–564 (1988).

Salim, M. et al., "Molecular Cloning of Amyloid cDNA from Alzheimer's Brain Messenger RNA: Correlative Neuroimmunological and in Situ Hybridization Studies," in: *Familial Alzheimr's Disease: Molecular Genetics, Clinical Prospects and Societal Issues,* Patterson, D. and C. J. Epstein, eds. Marcel Dekker: New York, pp. 153–165 (1989).

Sasaki, H. et al., "A HindIII polymorphism detected by the cDNA encoding amyloid beta protein of Alzheimer's disease," *Chem. Abstr. 107*(*13*):Abstr. No. 110352b (1987).

Schatz, P. J. et al., "Insertions of up to 17 Amino Acids into a Region of α–Tubulin Do Not Disrupt Function in Vivo," *Mol. Cell. Biol. 7*(*10*):3799–3805 (1987).

Schellenberg, G. D. et al., "Absence of Linkage of Chromosome 21q21 Markers to Familial Alzheimer's Disease," *Science 241*: 1507–1510 (1988).

Schellenberg, G. D. et al., "Genetic Linakge Evidence for a Familial Alzheimer's Disease Locus on Chromosome 14," *Science 258*:668–671 (Oct. 1992).

Selkoe, D. J. et al., "β–Amyloid precursor protein of Alzheimer disease occurs as 110– to 135– Kilodalton membrane–associated proteins in neural and nonneural tissues," *Proc. Natl. Acad. Sci. USA 85*: 7341–7345 (1988).

Selkoe, D. J. "In the beginning . . . ," *Nature 354* :432–433 (Dec. 1991).

Seubert, P. et al., "Isolation and quantification of soluble Alzheimer's β–peptide from biological fluids," *Nature 359*:325–327 (Sep. 1992).

Shaw, D. R. et al., "Mouse/Human Chimeric Antibodies to a Tumor–Associated Antigen: Biologic Activity of the Four Human IgG Subclasses," *J. Natl. Cancer Inst. 80*(*19*):1553–1559 (1988).

Shoji, M. et al., "Production of the Alzheimer Amyloid β Protein by Normal Proteolytic Processing," *Science 258*:126–129 (Oct. 1992).

Silver, P. A. et al., "Amino terminus of the yeast GAL4 gene product is sufficient for nuclear localization," *Proc. Natl. Acad. Sci. USA 81*:5951–5955 (1984).

Sisodia, S. S. et al., "Evidence That β–Amyloid Protein in Alzheimer's Disease Is Not Derived by Normal Processing," *Science 248*:492–495 (1990).

Stewart, G. D. et al., "RFLPs at the D21S19 locus of human chromosome 21" *Nucleic Acids Res. 13*(*19*):7168 (1985).

Stewart, G. D. et al., "Trisomy 21 (Down Syndrome): Studying Nondisjunction and Meiotic Recombination by Using Cytogenetic and Molecular Polymorphisms That Span Chromosome 21," *Am. J. Hum. Genet. 42*:227–236 (1988).

Stout, J. T. et al., "Expression of Human HPRT in the central nervous system of transgenic mice," *Nature 317*:250–252 (1985).

Stryer, L. ed., "Exploring Genes: Analyzing, Constructing, and Cloning DNA," in: *Biochemistry,* W. H. Freeman and Company: New York, pp. 117–141 (1988).

Suggs, S. V. et al., "Use of synthetic oligonucleotides as hybridization probes: Isolation of cloned cDNA sequences for human $\beta_2$ –microglobulin," *Proc. Natl. Acad. Sci. USA 78*(*11*):6613–6617 (1981).

Sun, L. K. et al., "Chimeric antibody with human constant regions and mouse variable regions directed against carcinoma–associated antigen 17–1A," *Proc. Natl. Acad. Sci. USA 84* :214–218 (1987).

Tamkun, J. W. et al., "Structure of Integrin, a Glycoprotein Involved in the Transmembrane Linkage between Fibronectin and Actin," *Cell 46*:271–282 (1986).

Tanzi, R. E. et al., "Amyloid β Protein Gene: cDNA, mRNA Distribution, and Genetic Linkage Near the Alzheimer Locus," Science 235:880–884 (1987).

Tanzi, R. E. et al., "The genetic defect in familial Alzheimer's disease is not tightly linked to the amyloid β–protein gene," Nature 329:156–157(1987).

Tanzi, R. E. et al., "The Amyloid β Protein Gene is Not Duplicated in Brains from Patients with Alzheimer's Disease," *Science 238*:666–669 (1987).

Tanzi, R. E. e al., "Protease inhibitor domain encoded by an amyloid protein precursor mRNA associated with Alzheimer's disease," *Nature 221*:528–530 (1988).

Tanzi, R. E. et al., "Molecular genetic approaches to Alzheimer's disease," *Trends Neurosci. 12*(*4*): 152–158 (1989).

Tanzi, R. E., "Molecular Genetics fo Alzheimer's Disease and the Amyloid β Peptide Presursor Gene," *Ann. Med. 21*(*2*):91–94 (1989).

Tanzi, R. E. et al., "Detailed Genetic Linkage Map of Human Chromosome 21: Patterns of Recombination According to Age and Sex," in: *Molecular Genetics of Chromosome 21 and Down Syndrome,* Wiley–Liss, Inc.: New York, pp. 15–26 (1990).

Tanzi, R. E., "The Alzheimer Disease–Associated Amyloid Beta Protein Precursor Gene and Familial Alzheimer Disease," in: *Molecular Genetics of Chromosome 21 and Down Syndrome,* Wiley–Liss, Inc.: New York, pp. 187–200 (1990).

Tanzi, R. E. and B. T. Hyman, "Alzheimer's mutation, " *Nature 350*:564 (April 1991).

Tanzi, R. E., "Genetic linkage studies of human neurodegenerative disorders," *Current Opinion Neurobiol. 1*:455–461 (Oct. 1991).

Tanzi, R. E., "Invited Editorial : Gene Mutations in Inherited Amyloidopathies of the Nervous System," *Am. J. Hum. Genet. 49*:507–510 (Sep. 1991).

Tanzi, R. E. et al., "Molecular Genetics of Alzheimer Disease Amyloid," *J. Biol. Chem. 266*(*31*):20579–20582 (Nov. 1991).

Tanzi, R. E. et al., "A Genetic Linkage Map of Human Chromosome 21: Analysis of Recombination as a Function of Sex and Age," *Am. J. Hum. Genet. 50*(*3*):551–558 (Mar. 1992).

Tanzi, R. E. et al., "Assessment of Amyloid β–Protein Precursor Gene Mutations in a Large Set of Familial and Sporadic Alzheimer Disease Cases," *Am. J. Hum. Genet. 51*(*2*):273–283 (Aug. 1992).

Tanzi, R. E. and B. T. Hyman, "Studies of Amyloid β–Protein Precursor Expression in Alzheimer's Disease," *Ann. New York Acad. Sci. 640*:149–154 (Feb. 1991).

Tanzi, R. E. et al., "Cellular specificity and regional distribution of amyloid β protein precursor alternative transcripts are unaltered in Alzheimer in hippocampal formation," *Mol. Brain Res. 18*(*3*):246–252 (May 1993).

Van Broeckhoven, C. et al., "Mapping of a gene predisposing to early–onset Alzheimer's disease to chromosome 14q24.3," *Nature Genetics 2*:335–339 (Dec. 1992).

Vaula, G. et al., "A novel but non–pathogenic mutation in exon 4 of the human amyloid precursor protein (APP) gene," *Neurosci. Lett. 144*:46–68 (Sep. 1992).

Verhoeyen, M. et al., "Reshaping Human Antibodies: Grafting an Atilysozyme Activity," *Science 239*:1534–1536 (1988).

Wahl, R. L. et al., "Improved Radioimaging and Tumor Localization with Monoclonal F(ab')$_2$" *J. Nucl. Med. 24*:316–325 (1983).

Wands, J. R. and Zurawski, Jr., V. R., "High Affinity Monoclonal Antibodies to Hepatitis B Surface Antigen (Hb$_s$ Ag) Produced by Somatic Cell Hybrids," *Gastroenterol. 80*:225–232 (1981).

Wasco, W. et al., "Identification of an Amyloid Precursor–Like Protein Localized on Chromosome 19," *Neurobiol. Aging 13* (*Suppl. 1*):S71 Abstr. No. 280 (Jun. 1992).

Wasco, W. et al, "Identification of a mouse brain cDNA that encodes a protein related to the Alzheimer disease–associated amyloid β protein precursor," *Proc. Natl. Acad. Sci. USA 89*:10758–10762 (Nov. 1992).

Wasco, W. et al., "The Amyloid Precursor–like Protein (APLP) Gene Maps to the Long Arm of Human Chromosme 19," *Genomics 15*:237–239 (Jan. 1993).

Wasco, W. et al., "Amyloid precursor–like protein: a member of the highly conserved APP gene family," in: *Alzheimer's Disease and Related Disorders,* Nicolini, M. et al., eds., Pergamon Press: Great Britain, pp. 229–231 (Jul. 1993).

Watkins, P.C. et al., "Isolation of polymorphic DNA segments from human chromosome 21," *Nucl. Acids Res. 13(17)* :6075–6088 (1985).

Watkins, P. C. et al., "Molecular genetics of human chromosome 21," *J. Med. Genet. 24*:257–270 (1987).
Weidemann, A. et al., "Identification, Biogenesis, and Localization of Precursors of Alzheimer's Disease A4 Amyloid Protein," *Cell 57*:115–126 (1989).
Wong, C. W. et al., "Neuritic plaques and cerebrovascular amyloid in Alzheimer disease are antigenically related," *Proc. Natl. Acad. Sci. USA 82*:8729–8732 (1985).
Wood, C. R. et al., "The synthesis and in vivo assembly of functional antibodies in yeast,"*Nature 314*:446–449 (1985).
Yamada, T. et al., "Structure and Expression of the Alternatively–Spliced forms of mRNA for the Mouse Homolog of Alzheimer's Disease Amyloid Beta Protein Precursor," *Biochem. Biophys. Res. Comm. 158*(*3*):906–912 (1989).
Yan, Y. C. et al., "Characterization of cDNA encoding a human sperm membrane protein related to A4 amyloid protein," *Proc. Natl. Acad. Sci. USA 87* :2405–2408 (1990).
Zain, S. B. et al., "Molecular Cloning of cDNA Transcribed from Messenger RNA of the Alzheimer Brain, Identification of cDNA for Amyloid and Glial Fibrillary Acidic Protein," *Soc. Neurosci. 13*:558 Abstr. No. 154.5 (1987).
Zain, S. B. et al., "Molecular Cloning an In Vitro Translation Studies of GFAP mRNA from Normal and Alzheimer Disease Brain Tissue," *J. Cell. Biochem. 11D* (*Suppl*): 198 Abstr. No. S415 (1987).
Zain, S. B. et al., "Molecular cloning of amyloid cDNA derived from mRNA of the Alzheimer disease brain: Coding an noncoding regions of the fetal precursor mRNA are expressed in the cortex," *Proc. Natl. Acad. Sci. USA 85*:929–933 (1988).
Zimmerman, K. et al., "Localization of the putative precursor of Alzheimer's disease–specific amyloid at nuclear envelopes of adult human muscle," *EMBO J. 7*(*2*):367–372 (1988).

```
CGGCACGAGG TGGCGCTGGG AGCTCCTGTC ACCGCTGGGG CCGGGTAGGG GCGGGCGGGA    60

GCGCAGGGAC GTGAGGGCCG AGCGGAC ATG GGG CCC ACC AGC CCC GCC GCT       111
                              Met Gly Pro Thr Ser Pro Ala Ala
                                1               5

CGC GGT CAG GGT CGC CGC TGG CGA CCG CCG CTG CCG CTG TTG CTG CCA     159
Arg Gly Gln Gly Arg Arg Trp Arg Pro Pro Leu Pro Leu Leu Leu Pro
     10                  15                  20

CTG TCA TTG CTG CTT CTG CGC GCG CAG CTC GCC GTC GGG AAC CTG GCT     207
Leu Ser Leu Leu Leu Leu Arg Ala Gln Leu Ala Val Gly Asn Leu Ala
 25                  30                  35                  40

GTT GGG AGC CCC AGC GCG GCC GAG GCT CCG GGG TCG GCT CAA GTG GCT     255
Val Gly Ser Pro Ser Ala Ala Glu Ala Pro Gly Ser Ala Gln Val Ala
                 45                  50                  55

GGA CTA TGT GGG CGT CTA ACC CTT CAC CGG GAC TTG CGC ACC GGC CGC     303
Gly Leu Cys Gly Arg Leu Thr Leu His Arg Asp Leu Arg Thr Gly Arg
             60                  65                  70

TGG GAA CCA GAC CCA CAG CGA TCA CGA CGC TGT CTT CTG GAC CCG CAG     351
Trp Glu Pro Asp Pro Gln Arg Ser Arg Arg Cys Leu Leu Asp Pro Gln
         75                  80                  85

CGC GTG CTG GAG TAC TGC AGA CAG ATG TAC CCC GAG CTG CAC ATA GCA     399
Arg Val Leu Glu Tyr Cys Arg Gln Met Tyr Pro Glu Leu His Ile Ala
     90                  95                 100

CGC GTG GAG CAG GCT GCA CAG GCC ATC CCG ATG GAG CGC TGG TGT GGG     447
Arg Val Glu Gln Ala Ala Gln Ala Ile Pro Met Glu Arg Trp Cys Gly
105                 110                 115                 120

GGT ACC CGG AGT GGC AGA TGC GCC CAC CCC CAC CAT GAG GTT GTG CCC     495
Gly Thr Arg Ser Gly Arg Cys Ala His Pro His His Glu Val Val Pro
                125                 130                 135

TTC CAT TGC CTG CCT GGC GAA TTC GTG AGT GAA GCC CTG CTA GTG CCC     543
Phe His Cys Leu Pro Gly Glu Phe Val Ser Glu Ala Leu Leu Val Pro
            140                 145                 150
```

FIG.2A

```
GAA GGC TGT CGG TTC TTG CAC CAG GAG CGT ATG GAC CAG TGT GAG AGT    591
Glu Gly Cys Arg Phe Leu His Gln Glu Arg Met Asp Gln Cys Glu Ser
        155                 160                 165

TCA ACC AGG AGG CAT CAG GAG GCT CAG GAG GCC TGC AGC TCT CAG GGC    639
Ser Thr Arg Arg His Gln Glu Ala Gln Glu Ala Cys Ser Ser Gln Gly
        170                 175                 180

CTC ATC CTG CAC GGC TCT GGC ATG CTT TTG CCC TGT GGC TCT GAT CGG    687
Leu Ile Leu His Gly Ser Gly Met Leu Leu Pro Cys Gly Ser Asp Arg
185                 190                 195                 200

TTC CGA GGT GTG GAG TAT GTA TGC TGT CCA CCT CCC GCA ACT CCC AAC    735
Phe Arg Gly Val Glu Tyr Val Cys Cys Pro Pro Pro Ala Thr Pro Asn
                205                 210                 215

CCA TCT GGG ATG GCA GCT GGT GAC CCC TCT ACC CGG TCC TGG CCC CTG    783
Pro Ser Gly Met Ala Ala Gly Asp Pro Ser Thr Arg Ser Trp Pro Leu
            220                 225                 230

GGG GGC AGA GCA GAG GGA GGT GAG GAT GAA GAG GAG GTG GAA TCT TTC    831
Gly Gly Arg Ala Glu Gly Gly Glu Asp Glu Glu Glu Val Glu Ser Phe
                235                 240                 245

CCT CAG CCA GTA GAC GAT TAC TTC GTA GAG CCC CCT CAG GCT GAA GAA    879
Pro Gln Pro Val Asp Asp Tyr Phe Val Glu Pro Pro Gln Ala Glu Glu
            250                 255                 260

GAA GAG GAA GAG GAG GAA GAA AGG GCC CCA CCT CCC AGC TCC CAC ACC    927
Glu Glu Glu Glu Glu Glu Glu Arg Ala Pro Pro Pro Ser Ser His Thr
265                 270                 275                 280

CCT GTC ATG GTT AGC AGA GTC ACT CCC ACC CCA AGG CCT ACT GAT GGT    975
Pro Val Met Val Ser Arg Val Thr Pro Thr Pro Arg Pro Thr Asp Gly
                285                 290                 295

GTG GAT GTT TAC TTT GGC ATG CCT GGG GAA ATC GGC GAG CAT GAG GGT    1023
Val Asp Val Tyr Phe Gly Met Pro Gly Glu Ile Gly Glu His Glu Gly
            300                 305                 310
```

FIG.2B

TTC CTG AGG GCC AAG ATG GAC CTG GAG GAG CGT AGG ATG CGC CAG ATT 1071
Phe Leu Arg Ala Lys Met Asp Leu Glu Glu Arg Arg Met Arg Gln Ile
315 320 325

AAT GAG GTG ATG CGT GAA TGG GCC ATG GCT GAC AGC CAA TCT AAG AAC 1119
Asn Glu Val Met Arg Glu Trp Ala Met Ala Asp Ser Gln Ser Lys Asn
330 335 340

CTG CCA AAG GCG GAC AGG CAG GCC CTG AAT GAG CAC TTC CAG TCC ATT 1167
Leu Pro Lys Ala Asp Arg Gln Ala Leu Asn Glu His Phe Gln Ser Ile
345 350 355 360

CTG CAG ACC CTG GAA GAA CAA GTG TCT GGT GAA CGG CAA CGC CTG GTG 1215
Leu Gln Thr Leu Glu Glu Gln Val Ser Gly Glu Arg Gln Arg Leu Val
365 370 375

GAG ACC CAC GCC ACC AGA GTC ATC GCT CTG ATC AAC GAC CAG CGC CGA 1263
Glu Thr His Ala Thr Arg Val Ile Ala Leu Ile Asn Asp Gln Arg Arg
380 385 390

GCA GCC CTG GAA GGT TTC CTG GCA GCC TTA CAG GGC GAT CCG CCT CAG 1311
Ala Ala Leu Glu Gly Phe Leu Ala Ala Leu Gln Gly Asp Pro Pro Gln
395 400 405

GCT GAG CGA GTT CTG ATG GCC CTG AGG CGC TAC CTG CGC GCC GAG CAG 1359
Ala Glu Arg Val Leu Met Ala Leu Arg Arg Tyr Leu Arg Ala Glu Gln
410 415 420

AAA GAG CAG AGG CAC ACT CTG AGG CAC TAC CAG CAC GTG GCC GCA GTG 1407
Lys Glu Gln Arg His Thr Leu Arg His Tyr Gln His Val Ala Ala Val
425 430 435 440

GAT CCT GAG AAG GCC CAG CAG ATG CGC TTT CAG GTC CAG ACC CAC CTT 1455
Asp Pro Glu Lys Ala Gln Gln Met Arg Phe Gln Val Gln Thr His Leu
445 450 455

CAG GTG ATC GAA GAG CGA ATG AAT CAG AGC CTG GGG CTG CTC GAC CAG 1503
Gln Val Ile Glu Glu Arg Met Asn Gln Ser Leu Gly Leu Leu Asp Gln
460 465 470

FIG.2C

AAC CCT CAC CTG GCT CAG GAG CTG CGG CCA CAG ATC CAG GAG CTT CTC 1551
Asn Pro His Leu Ala Gln Glu Leu Arg Pro Gln Ile Gln Glu Leu Leu
475 480 485

CTT GCT GAA CAC TTG GGT CCC AGT GAA CTG GAC GCC TCT GTG CCC GGG 1599
Leu Ala Glu His Leu Gly Pro Ser Glu Leu Asp Ala Ser Val Pro Gly
490 495 500

AGC AGC AGT GAG GAC AAA GGT AGC CTC CAG CCT CCC GAA TCC AAG GAC 1647
Ser Ser Ser Glu Asp Lys Gly Ser Leu Gln Pro Pro Glu Ser Lys Asp
505 510 515 520

GAT CCC CCA GTG ACC CTT CCA AAA GGG TCC ACA GAT CAA GAG TCA TCC 1695
Asp Pro Pro Val Thr Leu Pro Lys Gly Ser Thr Asp Gln Glu Ser Ser
525 530 535

TCC TCT GGG AGA GAG AAG CTA ACT CCA CTG GAG CAG TAT GAG CAA AAG 1743
Ser Ser Gly Arg Glu Lys Leu Thr Pro Leu Glu Gln Tyr Glu Gln Lys
540 545 550

GTG AAT GCA TCC GCC CCG AGG GGG TTT CCG TTC CAC TCG TCA GAT ATC 1791
Val Asn Ala Ser Ala Pro Arg Gly Phe Pro Phe His Ser Ser Asp Ile
555 560 565

CAG CGG GAT GAA CTG GCT CCT TCC GGG ACT GGA GTG TCC CGA GAG GCC 1839
Gln Arg Asp Glu Leu Ala Pro Ser Gly Thr Gly Val Ser Arg Glu Ala
570 575 580

TTG TCA GGT CTG CTG ATC ATG GGA GCT GGA GGA GGC TCT CTC ATT GTC 1887
Leu Ser Gly Leu Leu Ile Met Gly Ala Gly Gly Gly Ser Leu Ile Val
585 590 595 600

CTA TCC TTG CTG CTT CTG CGC AAG AAG AAA CCC TAT GGG ACT ATC AGC 1935
Leu Ser Leu Leu Leu Leu Arg Lys Lys Lys Pro Tyr Gly Thr Ile Ser
605 610 615

CAT GGA GTG GTG GAG GTG GAC CCC ATG CTG ACC CTG GAG GAG CAG CAG 1983
His Gly Val Val Glu Val Asp Pro Met Leu Thr Leu Glu Glu Gln Gln
620 625 630

FIG.2D

```
CTC CGG GAA CTT CAG AGG CAT GGC TAT GAG AAC CCC ACC TAC CGC TTC      2031
Leu Arg Glu Leu Gln Arg His Gly Tyr Glu Asn Pro Thr Tyr Arg Phe
            635                 640                 645

CTG GAA GAA CGA CCT TGACCCCTAC CCTAGCTGCC TTCAGCTGAG CCCTACTGCC      2086
Leu Glu Glu Arg Pro
    650

TTCTTCCGGC CCCCCAAACC CAACTCCCAG CTTCCGGTGG GGGAGGGAGA TCTTGACAAA    2146

TTCATTCTTG TTTCCCCTTC CTAGTTCCAA ATTCCACACC CTTAGAAATC CCCAGCTCCT    2206

GTCCCACAAG GGACCTCTTC ACCTTAATTT ATTTTACGTT AATTTATTGC TCCTTAAGGT    2266

GACCTGGGTC CCAGGTATGT ATGTCACTCC CTGGAATTCA CCATCCCACG TTTCTTCACT    2326

AACATCCCAA TAAACTCCTC TTTCCCTCCG GC                                  2358
```

FIG.2E

```
                  .         .         .         .         .
APLP1     1  LLLPLSLLLLRAQLAVGNLAVGSPSAAEAPGSAQVAGLCGRLTLHRDLRT  70
             :| .|.|||| |.:.. .|.|...:.|:  :.:|:| :||||.:|.::..
APP       1  MLPGLALLLL.AAWTARALEVPTDGNAGLLAEPQIAMFCGRLNMHMNVQN  49
                  .         .         .         .         .
         71  GRWEPDPQRSRRCLLDPQRVLEYCRQMYPELHIARVEQAAQAIPMERWCG 120
             |:|:.||  .: |: ..: :|:||.::||||:|..| :|.|::.::.||
         50  GKWDSDPSGTKTCIDTKEGILQYCQEVYPELQITNVVEANQPVTIQNWCK  99
                  .         .         .         .         .
        121  GTRSGRCAHPHHEVVPFHCLPGEFVSEALLVPEGCRFLHQERMDQCESST 170
              .|.. .||| |:|::||.|||||:|||||: |:|||||||| ||.
        100  RGRKQCKTHPHF.VIPYRCLVGEFVSDALLVPDKCKFLHQERMDVCETHL 148
                  .         .         .         .         .
        171  RRHQEAQEACSSQGLILHGSGMLLPCGSDRFRGVEYVCCPPPATPN..PS 218
             ::|  |.|.||..:  ||: ||||||| |:|||||:|||| :...:  .|
        149  HWHTVAKETCSEKSTNLHDYGMLLPCGIDKFRGVEFVCCPLAEESDNVDS 198
                  .         .         .         .         .
        219  GMAAGDPSTRSWPLGGR..AEGGED.......EEEVESFPQPVDDYFVEP 259
             : |.:|.|. .|. ::   |:|:||       ||||....:. .|   :.
        199  ADAEEDDSDVWWGGADTDYADGSEDKVVEVAEEEEVAEVEEEEADDDEDD 248
                  .         .         .         .         .
        260  PQAEEEEEEEEERAPPPSSHTPVM.............VSRVTPTPRPT.D 295
             .:::| |||.||. ..:..:|. :             | ||..|: .| |
        249  EDGDEVEEEAEEPYEEATERTTSIATTTTTTTESVEEVVRVPTTAASTPD 298
                  .         .         .         .         .
        296  GVDVYFGMPGEIGEHEGFLRAKMDLEERRMRQINEVMREWAMADSQSKNL 345
             :|| |:: ||: .||. | :||  ||.::. .:.:|||||. |:.|.|||
        299  AVDKYLETPGDENEHAHFQKAKERLEAKHRERMSQVMREWEEAERQAKNL 348
                  .         .         .         .         .
        346  PKADRQALNEHFQSILQTLEEQVSGERQRLVETHATRVIALINDQRRAAL 395
             ||||:.|: :|||. ::.||::...|||.||||| .|| |::||.|| ||
        349  PKADKKAVIQHFQEKVESLEQEAANERQQLVETHMARVEAMLNDRRRLAL 398
                  .         .         .         .         .
        396  EGFLAALQGDPPQAERVLMALRRYLRAEQKEQRHTLRHYQHVAAVDPEKA 445
             |.::.|||: ||.: :|:  |::|:||||||:..|||:|::||  |||.||
        399  ENYITALQAVPPRPRHVFNMLKKYVRAEQKDRQHTLKHFEHVRMVDPKKA 448
                  .         .         .         .         .
        446  QQMRFQVQTHLQVIEERMNQSLGLLDQNPHLAQELRPQIQELLLAEHLGP 495
             .|:| || |||.|| |||||||:|| . | :|:|:..:::||| |:  .
        449  AQIRSQVMTHLRVIYERMNQSLSLLYNVPAVAEEIQDEVDELLQKEQNYS 498
```

FIG.3A

```
              .         .         .         .         .
496 SELDASVPGSS..SEDKGSLQPPESKDDPPVTLPKGSTD......QESSS 537
    .:: |.: :..  | :.:.| |. ......|.| ....:      |.. |
499 DDVLANMISEPRISYGNDALMPSLTETKTTVELLPVNGEFSLDDLQPWHS 548

              .         .         .         .         .
538 SGREKLTPLEQYE.QKVNA..SAPRGFPFHSS....DIQRDELA...... 574
     | :.:.: .: | :.|:|  .|.||:. :.:    :|. :|:.
549 FGADSVPANTENEVEPVDARPAADRGLTTRPGSGLTNIKTEEISEVKMDA 598

              .         .         .         .         .
575 ..................PSGTGVSREALSGLLIMGAGGGSLIVLSLLLL 606
                      :.:.| .::|: ||:: |.. :.:||:.|::|
599 EFRHDSGYEVHHQKLVFFAEDVGSNKGAIIGLMVGGVVIATVIVITLVML 648

              .         .         .         .
607 RKKKPYGTISHGVVEVDPMLTLEEQQLRELQRHGYENPTYRFLEERP 653
     |||.|..| |||||||: :| ||.:|..:|.:|||||||:|:|:..
649 .KKKQYTSIHHGVVEVDAAVTPEERHLSKMQQNGYENPTYKFFEQMQ 694
```

FIG.3B extracellular domain I

```
                 .. |  |||.  . . . . .    .|  .  .|.| | | . . . .
APLP1      1  ILlpL  sLLLLrAqlaVgnLaVgspsAAeaPgsaQvAgLC  G RLtlHrdlrt
APP        1  MLpgL  aLLLL AaWtarALeVptdgnAgllaePQIAmfC  G RLnmHnmvqn
APPL       1  McaaLrrnLLLr slWvVlAigtaqvqAAssPrwPQIAvLCeaGqiyqpqylsee
                                                    ^

              |.| |..  . .|.| . . || ||..|....... . ..||
APLP1     71  GRWepDPq  rs rrCLlDpqrvLe YCrqmYPELhlarVeqAaQaipmerWCg
APP       50  GkWdsDPS  gT kTCi DtKegilqYCqevYPELqITNVVEAnQpvtIqnWCk
APPL      55  GRWvtDISkktTgpTCLrD KmdLd YCkkaYPnrdITNiVEsshyqkIggWCr
                         ^           ^                        ^

               .. ..   | . |..|| |.|.|.|||||..| |.|..... |. ..
APLP1    122  gtRsgrCA hp hHeV vPFhCLpGEFVSeALLVPEGCrFLHQERMDqCEsst
APP      100  rGRk qCk th pHfV iPyRCLvGEFVSDALLVPdkCkFLHQERMDvCEthl
APPL     108  qGaln aAkckgsHrwikPFRCL GpFqSDALLYPEGClFdHihnasrCwpfv
                                 ^          ^        ^

              ... ....|.. . . .||||||.. |.|||.||||
APLP1    172  RrHQeAqEACSsqGliLHgsGMLLPCGsDrFRGVEyVCCP
APP      148  hWHtvAkEtCSEkstnLHdyGMLLPCGIDkFRGVEFVCCP
APPL     159  RWnQtgaaACqErGmgmrtfaMLLPCGIsvFsGVEFVCCP
                      ^          ^           ^^
```

extracellular domain II

```
              .. ||. ..  || |  .. | ..| |||  .... .|| ..|
APLP1    316  AKmdLEErrmrqineVMREW amAdsQsKNL PKA DrQAlneHFQsilQtL
APP      318  AKeRLEakHRErmsqVMREW eEAerQaKNL PKA DKkAviqHFQekVesL
APPL     413  sqkRLEEsHREkvtrVMkdWsdIEekyQdmrLadPKAaqsfKQrmtarFQtsVQaL

              |.. |...|...| || | .|...| |.. . ||. || . .| | ...
APLP1    365  EEqvsgERQrLVETHatRViAIINDqRRaALEgflaALQgdPPqAerVlmaLrrYL
APP      368  EqEaanERQQLVETHmaRVeAmINDRRRIALEnYitALQavPPrprHVfnmLkKYv
APPL     470  EEEgnaEkhQLaamHqqRVIAhINqRkReAmtcYtqALteqPPnAhHVekcLqKIL

              ||..|...|.| |. | . ..| ..|.. | .. ..| .| ...|||. .|
APLP1    421  RAEQKeqrHTLrHYqH VaaVDP  EKAqQmRfQVqTHLqVIeERMNQSLgLL
APP      424  RAEQKDRqHTLkHfeH VrmVDP  kKAAQiRsQVmTHLrVIyERMNQSLsLL
APPL     523  RAIhKDRaHaLaHYrHIInsggPggIEaAAseRprtlerLidIdravNQSmtmL
```

FIG.4A cytoplasmic domain

```
                ........... .|..|||...|   .   ||... ..| .|||||||...|...
APLP1      609 KKKpYGTIS HGVVEVDPMLT   I   EEqqLrelQrHGYENPTYrFLEerp*
APP        649 KKKQYtSIH HGVVEVDaaVT   P   EERHLsKMQqNGYENPTYKFFEQMQn*
APPL       834 KwRtsrSpHaqGfiEVDqnVTthhPivrEEkivpnMQiNGYENPTYKYFEvke*
testis     145 rKRQYGTIS HGiVEVDPMLT   P   EERHLnKMQnHGYENPTYKYLEQMQi*
```

FIG.4B

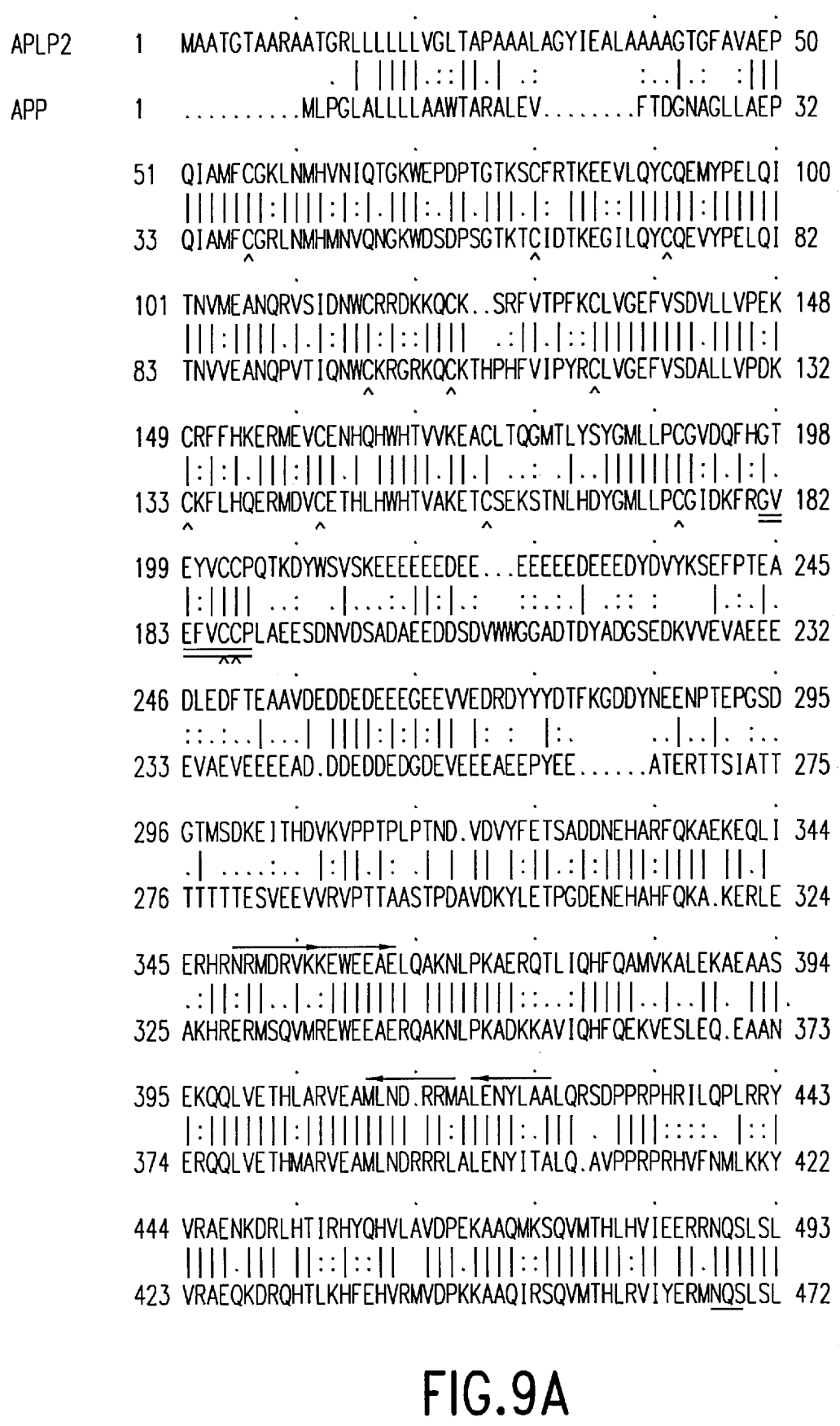

```
APLP2    1  MAATGTAARAATGRLLLLLLVGLTAPAAALAGYIEALAAAAGTGFAVAEP  50
              . | ||||.::||.|  .:          ...|.:  :|||
APP      1  ..........MLPGLALLLLAAWTARALEV........FTDGNAGLLAEP  32

        51  QIAMFCGKLNMHVNIQTGKWEPDPTGTKSCFRTKEEVLQYCQEMYPELQI 100
            ||||||:||||:|:|.|||:.||.|||.|:  |||::||||||:||||||
        33  QIAMFCGRLNMHMNVQNGKWDSDPSGTKTCIDTKEGILQYCQEVYPELQI  82
                  ^                   ^     ^

       101  TNVMEANQRVSIDNWCRRDKKQCK...SRFVTPFKCLVGEFVSDVLLVPEK 148
            |||:||||.|.|:|||:|::||||    .:||.|::|||||||||.||||.|
        83  TNVVEANQPVTIQNWCKRGRKQCKTHPHFVIPYRCLVGEFVSDALLVPDK 132
                  ^        ^  ^                      ^

       149  CRFFHKERMEVCENHQHWHTVVKEACLTQGMTLYSYGMLLPCGVDQFHGT 198
            |:|:|.|||:|||.| |||||.||.| ...: .|..|||||||:|.|:|.
       133  CKFLHQERMDVCETHLHWHTVAKETCSEKSTNLHDYGMLLPCGIDKFRGV 182
              ^        ^        ^          ^          ^

       199  EYVCCPQTKDYWSVSKEEEEEEDEE...EEEEEDEEEDYDVYKSEFPTEA 245
            |:||||  ..:  .|....:.||:|.:   :::.|  .:: :   |.:.|.
       183  EFVCCPLAEESDNVDSADAEEDDSDVWWGGADTDYADGSEDKVVEVAEEE 232
                ‾‾

       246  DLEDFTEAAVDEDDDEDEEEGEEVVEDRDYYYDTFKGDDYNEENPTEPGSD 295
            ::::..|...|  ||||:|:|:||  |: :   |:.       ..|..|. :..
       233  EVAEVEEEEAD.DDEDDEDGDEVEEEAEEPYEE......ATERTTSIATT 275

       296  GTMSDKEITHDVKVPPTPLPTND.VDVYFETSADDNEHARFQKAEKEQLI 344
            .|  ......:..  |:||.|:  .| | |||  |:||.:|||||:||||   ||.|
       276  TTTTTESVEEVVRVPTTAASTPDAVDKYLETPGDENEHAHFQKA.KERLE 324

       345  ERHRNRMDRVKKEWEEAELQAKNLPKAERQTLIQHFQAMVKALEKAEAAS 394
            .:||:||..|.:||||||||  ||||||||:...::|||||...|..||.  |||.
       325  AKHRERMSQVMREWEEAERQAKNLPKADKKAVIQHFQEKVESLEQ.EAAN 373

       395  EKQQLVETHLARVEAMLND.RRMALENYLAALQRSDPPRPHRILQPLRRY 443
            |:||||||||:||||||||||  ||:|||||:..|||  .  |||||::::.  |::|
       374  ERQQLVETHMARVEAMLNDRRRLALENYITALQ.AVPPRPRHVFNMLKKY 422

       444  VRAENKDRLHTIRHYQHVLAVDPEKAAQMKSQVMTHLHVIEERRNQSLSL 493
            ||||.|||  ||:::||   |||.||||::|||||||||:||  ||.||||||
       423  VRAEQKDRQHTLKHFEHVRMVDPKKAAQIRSQVMTHLRVIYERMNQSLSL 472
```

FIG.9A

```
494 LYKDPYVARI..QENDELLQAER.......ADM..........DQFTASI 524
    ||. | ||    :| ||||| |.       |:|          |.: :|:
473 LYNVPAVAEEIQDEVDELLQKEQNYSDDVLANMISEPRISYGNDALMPSL 522

525 SETPVDVRVSSEESE.EIPPFHPFHPFPALPENEDTQPELYHPMKKGSGV 573
    .||...| : . ::| .:..::|:|.|.| .  .:|: |:
523 TETKTTVELLPVNGEFSLDDLQPWHSFGADSVPANTENEV.......... 562

574 GEQDGGLIGAEEKVINSKNKVDENMVIDETLDKEMIFNAERVGGLE.ERE 622
     |. ::  :|:  :........|: .:|. : .|  :  : :|.| .::
563 .EPVDARPAADRGLTTRPGSGLTNIKTEEISEVKMDAEFRHDSGYEVHHQ 611

623 SVGPLREDFSLSSSASIGLLVIAVAIATVIVISLVMLRKRQVCTISHGIV 672
    .:. : ||.: ..:| |||:| :|.|||||||.||||:|:| ..| ||:|
612 KLVFFAEDVGSNKGAIIGLMVGGVVIATVIVITLVMLKKKQYTSIHHGVV 661

673 EVDPMLTPEERHLNKMQNHGYEMPTYKTLEQNQI* 706
    |||: :|||||||.|||.:|||||||| :||||
662 EVDAAVTPEERHLSKMQQNGYENPTYKFFEQMQN* 695
```

FIG.9B

```
APP695   ..........  M-....P-L-  LLLL-AWTA-  A--V......  ..---G-A--
APLP2    MAATG-AAR-  --....--L-  LLLLVGLTA-  AAALA----A  LA-A-G---A
APLP1    MGPTS-AAR-  ------P-L-  LLL-LSL---  -A-LA----A  VG-P--.A-A

APP695   LAEPQIAMFC  GRLNMHVNVQ  -GKWDSDP-G  TK-CI-TKEG  ILQYCQEVYP
APLP2    VAEPQIAMFC  GKLNMHMNIQ  TGKWEPDP-G  TK-CF-TKEE  VLQYCQEMYP
APLP1    -G-AQVA-LC  GRL-LH-DL-  TGRWEPDP--  SR-CL---Q-  VLEYC-QMYP

APP695   ELQITNVVEA  NQPV-IQNWC  KRDRK.QCK-  --HFVIPYRC  LVGEFVSDAL
APLP2    ELQITNVMEA  NQ-V-IDNWC  RRGKK.QCK.  .-RFV-PFKC  LVGEFVSD-L
APLP1    ELHI--V-QA  -QAI-ME-WC  ---R---C--  --H-VVPF-C  LPGEFVSEAL

APP695   LVPDKCKFLH  QERMDVCE-H  -HWHTVAKE-  CS--S--LHD  YGMLLPCGDD
APLP2    LVPEKCRFFH  -ERMEVCE-H  -HWHTV-KEA  C--QG--L-S  YGMLLPCGVD
APLP1    LVPEGCRFLH  QERMD-CE--  -RRH--A-EA  CSSQG--LHG  -GMLLPCG-D

APP695   KFRGVEFVCC  P-A-E-D-V-  -AD-EEDD-D  ---GG-D-D-  -DG-E----E
APLP2    -FHG-EYVCC  P---D---VS  --E-EEED-E  ...EE-EEDE  EED-D----E
APLP1    RFRGVEYVCC  P-P---N--G  -A--D-----  ---GG--EGG  ED........

APP695   -A-EEEV-E-  -E---D.DDE  DDEDGDEVEE  E-E--YEE..  ....--ER-T
APLP2    -P-E-DLEDF  -E---D-DDE  DEEEGEEV-E  D-D--YD---  -----EE-PT
APLP1    ...EEEVE-F  -Q---D---E  --Q--EE-EE  E.........  .....EERA-

APP695   --A-TTT---  --V--VVRVP  -TA--T-DAV  D-YLETPGDE  NEHAHFQKA.
APLP2    -PGS--T---  --I---VKVP  PTP-PT-D.V  DVYFET-ADD  NEHARFQKA-
APLP1    -P-S-T---.  .....V-RV-  PTP-PT.DGV  DVYFG-PGE-  -EH--F-RA.

APP695   KE-LE-KHRE  RM-QVMREWE  EAE-QAKNLP  KADK-AVIQH  FQ--VE-LEQ
APLP2    KEQL-ERHRN  RMD-V-KEWE  EAE-QAKNLP  KAERQ-LIQH  FQ-MV--LE-
APLP1    K-DLEERR--  -INEVMREW-  -AD-Q-KNLP  KADRQAL-EH  FQ-ILQ-LEE

APP695   .EAA-ERQQL  VETHMARVEA  MLND-RRLAL  ENYI-ALQ.A  -PPRP--VF-
APLP2    -EAASE-QQL  VETHLARVEA  MLND.RRMAL  ENYLAALQ-S  DPPRP-RIL-
APLP1    .Q--GERQ-L  VETH--RV-A  LIND-RR-AL  E-FLAALQ.G  DPP-A-RVL-

APP695   -LKKYVRAEQ  KDR-HTLKHF  EHV--VDP-K  AAQIRSQVMT  HLRVI-ERMN
APLP2    PLRRYVRAE-  KDR-HTIRHY  QHV-AVDPEK  AAQMKSQVMT  HLHVIEER-N
APLP1    ALRRYLRAEQ  KE--HTLRHY  QHV-AVDPEK  A-QMR-QV-T  HL-VIEERMN
```

FIG.10A

```
APP695   QSLSLLY--P -VAEEI DE- DELLQ-E--- -----ANM-- --------D-
APLP2    QSLSLLY-DP -VA--..QE- DELLQAER.. .....ADM.. ........D-
APLP1    QSLGLL--NP -LAQEL -Q- QELL-AEH.. .......... ..........

APP695   L-PSL-ET-- -V-L---NGE -SL--LQPWH -F-A-----N TE-EV.....
APLP2    F-ASISET-- -V-VSS-ESE .-I-PFHPFH PFPA-----D TQ-EL-----
APLP1    ..---SE--- -V--SS-E-- -SL-P----D --PP------ T--E......

APP695   ......E--D A--AA---L- ----SG--NI --EE--E-KM -AE--H-SG-
APLP2    ------E--G G--GA---V- -S-----ENM --DE--D--M --NA-R-GGL
APLP1    .......... .......... .S--SG-E-- ---E--E-K- -A-A-R---F

APP695   ...E--HQ-L --F-ED-G-- -GA-IGLMV- GV-IATVIVI -LVMLKKKQ.
APLP2    ...E.ERE-V G-L-ED-S-S -SA-IGLLVI AVAIATVIVI SLVMLRKRQ.
APLP1    ---D-QRD-L A..--G-G-S --A--GLLIM G-G-G-LIVL SLLLLRKK--

APP695   Y--I-HGVVE VDA-VTPEER HL-KMQ-NGY ENPTYKFFEQ MQ-*
APLP2    --TISHGIVE VDPMLTPEER HL-KMQ-HGY ENPTYK-LEQ MQ-*
APLP1    Y-TISHGVVE VDPMLT-EE- QL--LQ-HGY ENPTY-FLEE --*
```

FIG.10B

AMYLOID PRECURSOR-LIKE PROTEIN AND USES THEREOF

This application is a divisional of U.S. application Ser. No. 08/007,999 filed Jan. 21, 1993, which is a continuation-in-part application of U.S. application Ser. No. 07/930,022 filed Aug. 17, 1992, now abandoned, which is a continuation-in-part application of U.S. application Ser. No. 07/872,642 filed Apr. 20, 1992, now abandoned, which disclosures are herein incorporated in their entirety.

The present invention was made utilizing funds of the United States Government. The United States Government is hereby granted a worldwide royalty fee, paid up, non-exclusive license in the invention.

BACKGROUND OF THE INVENTION

1. Field of the Invention

The present invention relates to amyloid precursor-like proteins (APLPs) including APLP1 and APLP2; products and processes involved in the cloning, preparation, and expression of genes for APLPs; antibodies with specificity to these proteins and to diagnostic and therapeutic uses thereof.

2. Brief Description of the Background Art

Alzheimer's disease (AD) is a neurodegenerative disorder characterized by the presence of neurofibrillary tangles, and amyloid in the form of senile plaques and blood vessel deposits in the brain. The main component of amyloid is Aβ, a 39–43 amino acid peptide derived from a larger amyloid precursor protein (APP) encoded by a gene on chromosome 21 (Glenner and Wong, *Biochem. Biophys. Res. Commun.* 120:885–890 (1984); Goldgaber et al., *Science* 235:877–880 (1987); Kang et al., *Nature* 325:733–736 (1987); Robakis et al., *Proc. Natl. Acad. Sci. USA* 84:4190–4194 (1987); Tanzi et al., *Science* 235:880–884 (1987)). A proportion of AD is inherited (reviewed in St. George-Hyslop et al., *Neurobiol. Aging* 10:417–425 (1989)) and the familial form (FAD) has been clearly shown to be a genetically heterogeneous disorder (Schellenberg et al., *Science* 241:1507–1510(1988); St. George-Hyslop et al., *Nature* 347:194–197 (1990)). An early-onset (<65 years of age) FAD locus was mapped to chromosome 21 (St. George-Hyslop et al., *Science* 235:885–889 (1987)), and a small percentage (less than 3%) of FAD is linked to point mutations within the APP gene (Goate et al., *Nature* 349:704–706 (1991); Murrell et al., *Science* 254:97–99 (1991); Chartier-Harlin et al., *Nature* 353:884–846 (1992); Tanzi and Hyman, Ann. N. Y. Acad. Sci 640:149–154 (1992); Mullan et al., *Nature Genetics* 2:340–342 (1992)). More recently, studies revealed the presence of a major early-onset FAD locus on chromosome 14 (Mullan et al., *Nature Genetics* 2:340–342 (1992); Schellenberg et al., *Science* 258:668–673 (1992); St. George-Hyslop et al., *Nature Genetics:* in press (1992); Broeckhoven et al., *Nature Genetics* 2:335–339 (1992)). Some early-onset FAD pedigrees do not demonstrate linkage to either the APP gene or chromosome 14 (Schellenberg et al., *Science* 241:1507–1510(1988); St. George-Hyslop et al., *Nature* 347:194–197 (1990); Schellenberg et al., *Science* 258:668–673 (1992); Tanzi, R. E., Am. J. *Human Genet.* 51:273–282 (1992)).

A subset of, but not all late-onset (>65 years of age) FAD pedigrees appear to be linked to a locus on chromosome 19 (Pericak-Vance et al.,*Am. J. Hum. Genet.* 48, 1034–1050 (1991)). Therefore, in addition to genes on chromosomes 14, 19 and 21 there would appear to be at least two additional FAD loci that remain unmapped. Candidate genes for other FAD loci include potential APP gene homologues which might either serve as alternative substrates for amyloid formation, or interfere with normal processing of APP.

APP resembles an integral membrane protein with a small cytoplasmic C-terminal domain and a larger, extracellular N-terminal domain (Kang et al., *Nature* 325:733–736 (1987)). The APP gene produces at least six transcripts (Ponte et al., *Nature* 331:525–527 (1988); Tanzi et al., *Nature* 331:528–530 (1988); Kitaguchi et al., *Nature* 331:530–532; De Sauvage et al., Science 245:651–655 (1989); Jacobsen et al., *Neurobiol. Aging* 12:575–583 (1991); Konig et al.,*J. Biol. chem.* 267:19804–19809 (1992) ), five of which include an alternatively spliced exon encoding a Kunitz type protease inhibitor domain. APP appears to be processed through at least two pathways. A secretory pathway results in the cleavage of APP at a site near the membrane of extracellular-junction, within the βA4 domain (Esch et al., *Science* 248:1122–1124 (1990); Sisodia et al., *Science* 248:492–495 (1990)), and precludes the formation of Aβ. Alternatively, processing in the endosomal-lysosomal pathway leads to the production of carboxy terminal derivatives that contain the Aβ peptide (Estus et al., *Science* 255:726–728 (1991); Golde et al., *Science* 255:728–730 (1991); Haass et al., *Science* 357:500–503 (1992)). More recently, it has been demonstrated that Aβ is generated in a soluble form by cultured cells (Haass et al., *Nature* 359:322–325 (1992); Sebubert et al., *Nature* 359:325–327 (1992); Shoji et al., *Science* 258:126–129 (1992)), although the exact pathway leading to the generation of soluble Aβ is unknown. Presumably, a precise balance among these pathways must be maintained in order to avoid the overproduction of amyloidogenic fragments.

It has previously been hypothesized that proteins resembling APP in amino acid sequence and overall structure may interact with, and effectively compete for factors playing a role in the maturation and/or metabolism of APP (Wasco et al., *Genomics*: in press (1992); Wasco et al., *Proc. Natl. Acad. Sci.* USA 89:10758–10762 (1992)). Recent evidence indicates that APP is a member of a family of proteins with specific domains that have been remarkably well conserved.

cDNA clones predict that APP is a transmembrane protein with a small intracellular C-terminal domain and a larger, extracellular N-terminal domain (Goldgaber et al., *Science* 235:877–880(1987); Kang et al., *Nature* 325:733–736 (1987); Robakis et al., *Proc. Natl. Acad. Sci.* USA 84:4190–4194 (1987); and Tanzi et al., *Science* 235:880–884 (1987)). There are at least four forms of APP that result in proteins of 563, 695, 751 and 770 amino acids (De Sauvage et al., *Science* 245:651–653 (1989); Kitaguchi et al., *Nature* 331:530–532 (1988); Ponte et al., *Nature* 331:525–527 (1988); and Tanzi et al., *Nature* 331:528–530 (1988)). At least three of these are the result of alternative splicing (Kitaguchi et al., *Nature* 331:530–532 (1988); Ponte et al., *Nature* 331:525–527 (1988); and Tanzi et al., *Nature* 331:528–530(1988)). The two larger forms of APP contain a 56 amino acid insert that has homology to the KuNa family of protease inhibitors (Kitaguchi et al., *Nature* 331:530–532 (1988); Ponte et al., *Nature* 331:525–527 (1988); and Tanzi et al., *Nature* 331:528–530(1988)).

One of the secreted forms of APP that contains a protease inhibitor domain has been found to be identical to protease nexin-II (Oltersdorf et al, *J. Biol. Chem.* 265:4492–4497 (1990); and Saitoh et al., *Cell* 58:615–622 (1989)).

The βA4 domain spans the predicted membrane-extracellular junction of APP. How this peptide is liberated from the precursor protein in Alzheimer's disease remains unclear. Results from a number of laboratories suggest that normally the precursor protein is secreted via cleavage at sites that are at or near the membrane-extracellular junction, apparently within the βA4-domain (Esch et al., *Science* 248:1122–1124 (1990); Selkoe et al., *Proc. Natl. Acad. Sci. USA* 85:7341–7345 (1988); Weidman et al., *Cell* 57:115–126 (1989); and Sisoda et al., *Science* 248:492–495 (1990)). If these findings are correct, normal processing of the secreted form of APP would preclude the formation of βA4, and therefore, of amyloid itself. Such a model implies that βA4 contained within the plaques and cerebrovascular deposits is the result of an abnormal processing event.

SUMMARY OF THE INVENTION

Presently, human and mouse cDNA clones encoding an amyloid precursor-like protein APLP1 on human chromosome 19 that is similar to APP in overall structure and amino acid sequence, have been isolated (Wasco et al., *Genomics*: in press (1992); Wasco et al., *Proc. Natl. Acad. Sci. USA* 89:10758–10762 (1992)).

Specifically, a mouse brain cDNA that encodes a protein whose predicted amino acid sequence is 42% identical and 64% similar to APP, has presently been identified. This amyloid precursor-like protein (APLP1) is clearly not encoded by the mouse homologue of human APP which homologue has been cloned previously and found to be 96.8% identical to human APP (Yamada et al., *Biochem. Biophys. Res. Comm.* 158:9060912 (1987)). An APP-like gene has also been isolated from Drosophila (APPL; Rosen et al., *Proc. Natl. Acad. Sci. USA* 86:2478–2482 (1989)) and another has been reported in the form of a partial cDNA clone isolated from a rate testes library (Yan et al., *Proc. Natl. Acad. Sci. USA* 87:2405–2408 (1990)). Interestingly, Luo et al. (Luo et al., *Neuron* 9:595–605 (1992)) have demonstrated a functional homology between APPL and APP. Transgenes expressing human APP or Drosophila APPL both show a similar level of rescue of Appl-fast phototaxis defect Drosophila mutants. These data would indicate that APP is a member of an evolutionarily highly conserved family of proteins that may share common functions and interact with similar proteins.

The present APLP1 shares three distinct regions of homology with APP. It is encoded by a 2.4 kb message that is present in mouse brain and neuroblastoma cells. Antibodies raised against a synthetic peptide derived from the C-terminus of APLP1 stain the Golgi in neuroblastoma cells.

In an attempt to isolate other members of the APP protein family, the mouse APLP1 sequence was first used to scan the Genbank database for homologous sequences. In addition to obtaining matches for APP, APPL, and the partial cDNA from rate testes, a match with an anonymous 274 base pair human brain cDNA entry (Genbank accession number M78104), was noted. This match, which was significant but not identical to mouse APLP1 (63% identity), indicated that M78104 was a small piece of a cDNA encoding a second APLP. In order to characterize the APP-like gene family in more detail, full length cDNAs for this second APLP, APLP2, were isolated. The isolation and characterization of APLP2 cDNA clones from human brain, provide further support for the hypothesis that APP is a member of a highly conserved gene family.

The cDNA described here, together with APP and two other genes—one from Drosophila (Rosen et al., *Proc. Natl. Acad. Sci. USA* 86:2478–2482 (1989)), and one from rat (Yan et al., *Proc. Natl. Acad. Sci. USA* 87:2405–2408 (1990))—encode a family of proteins with conserved domains of homology which may share common functions.

The present APLP is a membrane associated protein which is localized to the golgi.

The present invention relates to amyloid precursor-like proteins (APLPs), products and processes involved in the cloning, preparation and expression of genes for APLPs; antibodies with specificity to these proteins; and nucleotide probes corresponding to an APLP or portions of an APLP polypeptide. An APLP polypeptide is useful for producing antibodies thereto. The antibodies and probes are useful for detecting the presence of an APLP in biological specimens, including, for example, body fluid, serum or tissue samples from an animal or human.

The present invention relates to the identification, characterization and sequencing of cDNAs and genomic fragments which encode APLPs that are present in mammalian cells including brain cells and neuroblastoma cells.

According to the invention, there are provided genetic sequences encoding APLPs. The invention also provides for expression vectors containing such genetic sequences, hosts transformed with such expression vectors, and methods for producing the genetically engineered or recombinant APLPs.

The present invention also provides antibodies which specifically recognize an APLP.

The present APLP cDNA and recombinant protein are useful for making antibodies which specifically recognize an APLP. Such antibodies are useful for detecting an APLP in a biological specimen.

A cDNA from a mouse brain library that encodes a protein whose predicted amino acid sequence is 42% identical and 64% similar to the amyloid precursor protein (APP) has been isolated. This 653 amino acid amyloid precursor-like protein (APLP1) is similar to APP in overall structure as well as amino acid sequence. The amino acid sequence homologies are concentrated within three distinct regions of the two proteins where the identities are 47%, 54% and 56%. All three regions are also strongly conserved in the Drosophila APP-like gene APPL (Rosen, et al., *Proc. Natl. Acad. Sci. USA* 86:2478–2482 (1989)).

Notably, twelve cysteine residues are conserved in the cysteine-rich region of both APLP1 and APLP2, as are an extracellular N-glycosylation site and the cytoplasmic clathrin-binding domain. The cytoplasmic domain is also conserved in a partial cDNA clone reported to encode an APP-like gene in rat testes (Yan et al. *Proc. Natl. Acad. Sci. USA* 87:2405–2408 (1990)). These data suggest that APP is part of a highly conserved gene family.

The present mouse APLP1 cDNA hybridizes to two messages of approximately 2.4 and 1.6 kb that are present in mouse brain and neuroblastoma cells.

APLP1 has been mapped to chromosome 19 within the same general region as the locus that has been reported to be linked to a form of late-onset familial Alzheimer's disease. Specifically, the APLP1 gene locus is located on the long arm of chromosome 19 between 19q13.2 and the centromere. In situ hybridization studies show APP and APLP to be expressed in similar human brain regions and cell sub-populations. APLP1 is a candidate gene for the gene defect for late-onset familial Alzheimer's disease.

Human APLP2 is encoded by a 706 amino acid sequence that is similar to APP and APLP1 in overall structure as well as amino acid sequence. APLP2 is 52% identical, 69% similar to APP695 and 43% identical, 63% similar to APLP1. Virtually all of the identified domains and motifs that characterize APP, APPL and APLP1 are present in APLP2. Specifically, an N-terminal cysteine-rich region (consisting of 12 cysteines), a novel zinc-binding motif (Bush et al., *Neurobiol. Aging* 13 (supplement 1):A.331 (1992)), an acidic-rich domain, N-glycosylation sites, a hydrophobic membrane spanning domain and a cytoplasmic domain containing a clathrin binding motif and potential serine/threonine, casein kinase I, II and tyrosine phosphorylation sites are conserved in APLP2. APLP1 and APLP2 are candidate genes for late onset familial Alzheimers disease.

DESCRIPTION OF THE FIGURES

FIGS. 2A–2E Nucleotide and amino acid sequence of the APLP1 cDNA. The composite nucleotide sequence (SEQ ID NO:2) and the predicted amino acid sequence (SEQ ID NO:3) of APLP1 is shown. The predicted membrane spanning region is underlined. The location of the primers that were used for the RACE procedures are indicated by arrowed lines over the nucleotide sequences. The location of the peptide sequence used for the production of antisera is double underlined. Predicted N-glycosylation sites are underlined with a squiggly line and a region surrounding a potential tyrosine phosphorylation site is underlined by dots. The polyadenylation signal is indicated by bold face type and the stop codon is shown by an asterisk.

FIGS. 3A–3B Comparison of the APLP1 (SEQ ID NO:3) and APP (SEQ ID NO:5) amino acid sequences. The UWGCG Bestfit analysis of the mouse APLP1 and human APP 695 (Chen, et al., *J. Biol. Chem.* 265:3116–3123 (1990)) is shown. Identities are indicated by a vertical line between the two amino acids. Similarities are indicated by a single or double dot. Gaps produced by the Bestfit alignment are shown by dots in the sequence. The βA4-protein sequence is underlined in the APP sequence. The identities are concentrated in three regions: APLP amino acids 21–211, 316–488, and 609–654.

FIGS. 4A–4B Domains of homology. Regions of the amino acid sequences of the mouse amyloid precursor like protein (APLP1) (SEQ ID NOS:6,7,8), the human amyloid precursor protein APP (SEQ ID NOS:9,10,11), the Drosophila amyloid precursor-like protein (APPL1)(SEQ ID NOS:11,12,13) and the rat testis (SEQ ID NOS:13,14,15) cDNA (testis) are compared. Amino acids that are identical in all of the sequences in the domain are shown as capital letters in bold face type and are identified by the presence of a vertical line (|) above the sequences. Amino acids that are the same in more than one sequence are shown as capital letters and have a dot (°) over the sequences. Amino acids that are not identical to any others are shown as lower case letters. The conserved cysteines are identified by the presence of a carrot underneath the sequence. Spans of particularly conserved amino acids are underlined. An N-glycosylation signal is identified by a double underline. Stop codons are indicated by an asterisk and the amino acid numbers of the sequences are shown at the beginning of each line.

Figure 1:
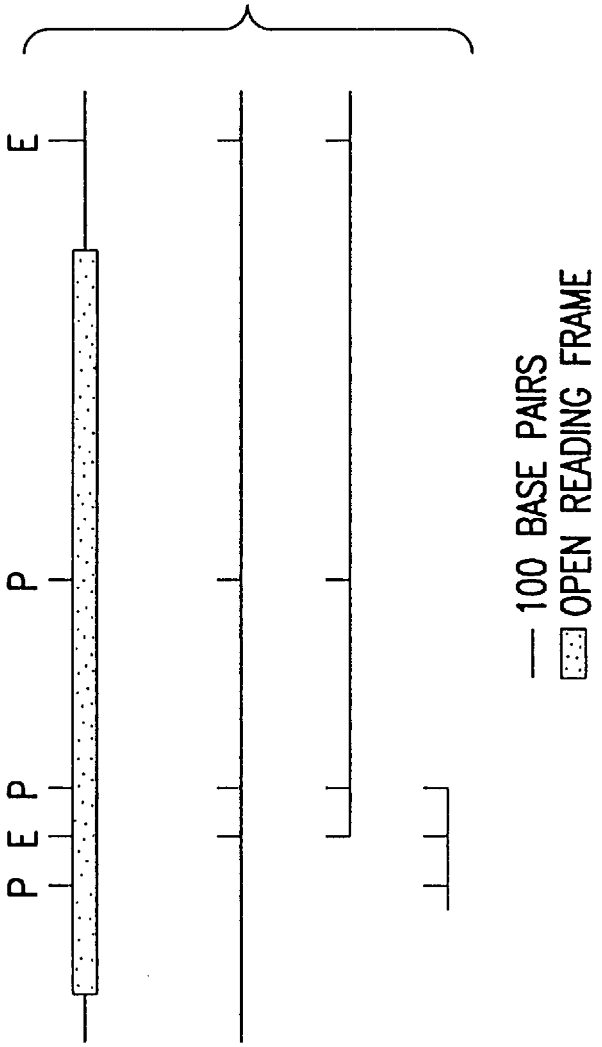
FIG. 1 Schematic representation of the mouse APLP1 open reading frame and the relation of various cDNA clones. The 2361 base pair open reading frame and the non-coding region of the APLP1 cDNA are shown. Also shown are the relative locations of two representative cDNA clones found in 11 libraries, 69A and 1A, and a clone obtained through the RACE procedure, J. Restriction enzyme sites: E=EcoRI, P=PstI.

A) Mouse brain protein was probed with antiserum 301 or preimmune serum at a dilution of 1:100. The binding of antiserum 301 to the 65 and 33 kDa proteins is inhibited by the presence of increasing amounts of the peptide QQLRELQRH, used to immunize the rabbit. Preimmune serum with no peptide (lane 1); immune serum with no peptide (lane 2); immune serum preabsorbed with 5 ng/ml peptide (lane 3); immune serum preabsorbed with 50 ng/ml of peptide (lane 4); immune serum preabsorbed with 500 ng/ml of peptide (lane 5). Preabsorption of immune serum with 500 ng of an irrelevant yeast β-tubulin peptide had no effect on the binding (lane 6).

B) Neuroblastoma cell extracts probed with preimmune serum (lane 1) and 301 antiserum (lane 2). Both sera were used at a dilution of 1:100.

C) Anti-peptide (QQLRELQRH) antiserum recognizes a β-galactosidase-APLP1 fusion protein. Western blots on bacterially produced proteins. Lanes 1–3 were stained with preimmune serum from rabbit 301. Lanes 4–6 were stained with immune serum. Lanes 1 and 4: induced (temperature sensitive induction and promoter) cells containing a plasmid with its β-galactosidase gene fused to an APLP1 cDNA fragment inappropriately oriented for production of an APLP1 epitope. Lanes 2 and 5: uninduced cells containing a plasmid with its β-galactosidase gene fused in frame to the APLP open reading frame. Lanes 3 and 6: same cells as in lanes 2 and 5 except induced. Induced cells were grown at 42° C. Uninduced cells were grown at 30° C. The arrowhead indicates a β-galactosidase-APLP1 fusion protein recognized by immune serum but not by preimmune serum. That protein is approximately 24 kDa larger than β-galactosidase alone, as predicted, due to the insertion of 222 additional residues of APLP1 open reading frame.

Figure 7A:
Figure 7B:
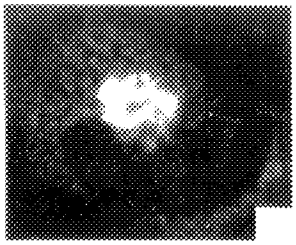
Figure 7C:
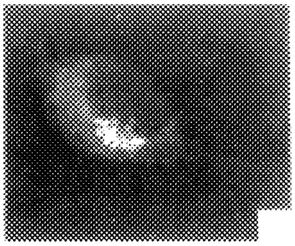
Figure 7D:
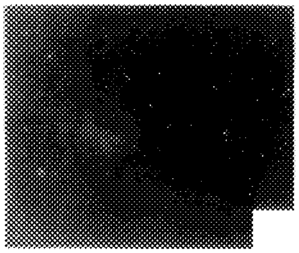
Figure 7E:
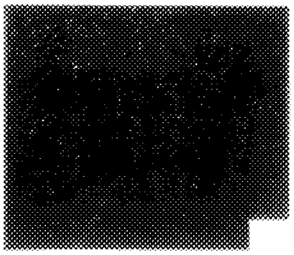

FIGS. 7A–7E Immunofluorescence staining of mouse neuroblastoma cells with antiserum 301. Cells were stained with antiserum 301 at a dilution of 1:10,000 as described in Materials and Methods. FIG. 7A shows neuroblastoma cells stained with antiserum 301. FIG. 7B shows a higher magnification of a cell stained with antiserum 301 where the reticular pattern is evident. This staining pattern is similar to that seen when an antibody to a known Golgi enzyme (mannosidase II) is used to stain the cells (FIG. 7C). The perinuclear staining is competed by the addition of the peptide that was used as the antigen (FIG. 7D), and is not seen in the presence of preimmune serum (FIG. 7E). The magnification in FIG. 7A and FIGS. 7C–7E is 720× and in FIG. 7B 950×.

Figure 8:
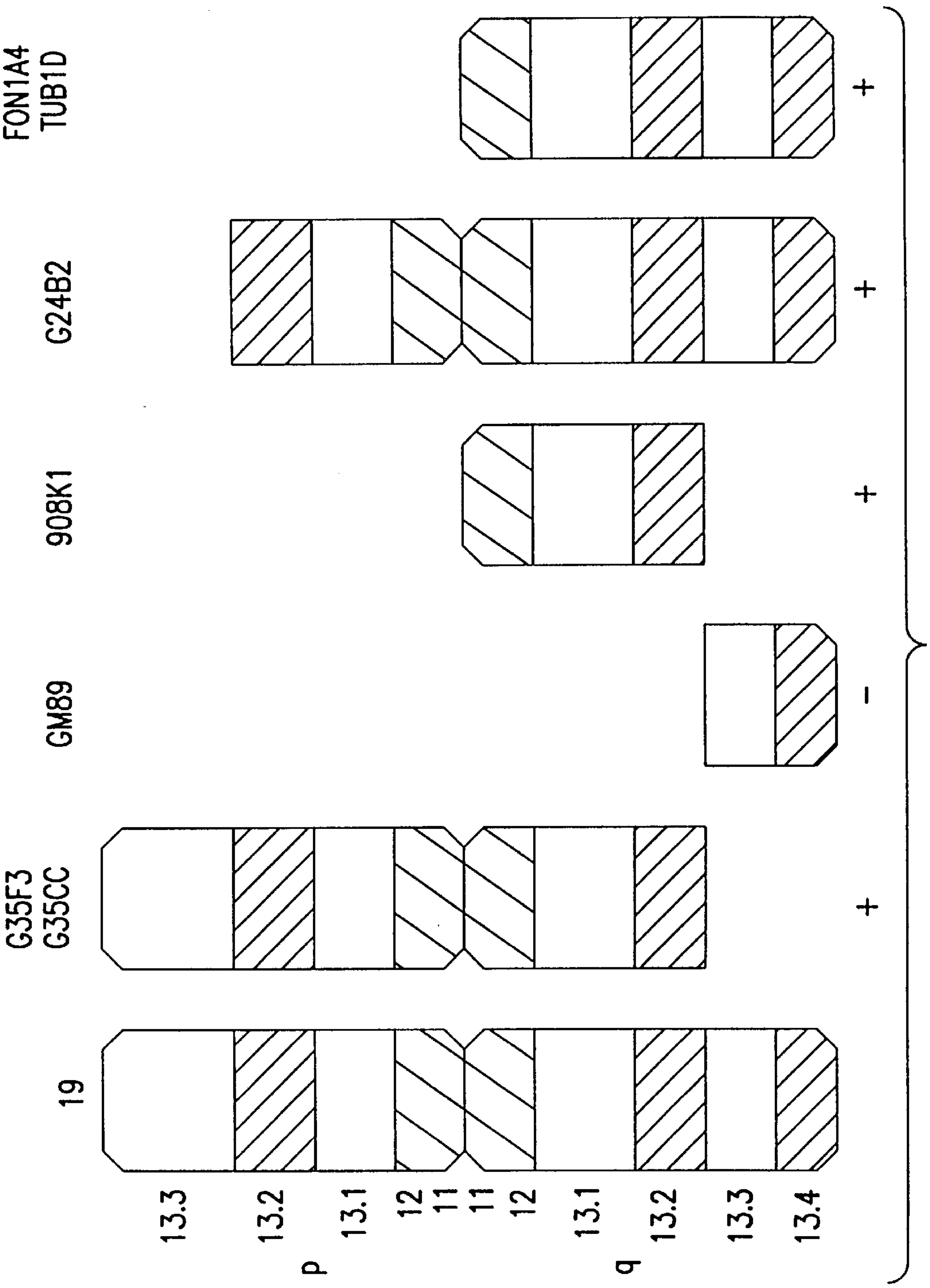

FIG. 8. Mapping of the APLP1 locus using a somatic cell hybrid panel. All hybrids have been previously described (Brook et al., *Hum. Genet.* 87:65–72 (1991); Chartier-Harlin et al., *Nature* 353:884–846 (1991); and Geissler et al., *Cell Mol. Genet.* 17:197–214 (1991)). The portions of chromosome 19 retained in each human-rodent cell hybrid are illustrated, and the names of the representative cell lines are shown above. The presence (+) or absence (−) of APLP1 in each hybrid cell line is indicated.

FIGS. 9A–9B. Comparison of APLP2 (SEQ ID NO:4) and APP (SEQ ID NO:5) amino acid sequences. An alignment of the human APLP2 amino acid sequence and the human APP695 (Kang et al., *Nature* 325:733–736 (1987)) was generated using the UWGCG GAP analysis. Gaps produced by the alignment are indicated by dots in the sequence. The location of the four PCR primers that were used to generate the SG190 probe (see Example 3) are indicated by arrows above the amino acid sequence. Twelve conserved cysteines are indicated by carets (^) under the sequence and a zinc-binding motif is indicated by a double underline. A conserved acidic-rich region is located between APLP2 amino acids 216 and 278. An N-glycosylation signal is underlined, an alternatively spliced exon is overlined, predicted transmembrane regions are shown in italics, and a clathrin binding motif is indicated by bold face type. Potential phosphorylation sites are indicated by a # sign (protein kinase C), a sign (casein kinase I and II) or a ° sign (tyrosine kinase) over the sequence. Stop codons are indicated by an asterisk.

FIGS. 10A–10B. Alignment of the amino acid sequences of the members of the APP-gene family. The sequences of human APP (SEQ ID NO:5) human APLP2 (SEQ ID NO:4), mouse APLP1 (SEQ ID NO:3) (Wasco et al., *Proc. Natl. Acad. Sci. USA* 89:10758–10762 (1992)) are presented as aligned by the UWGCG PILEUP program. Amino acids that are not identical or conservatively substituted are indicated by a dash. Gaps in the amino acid sequence that were created by the alignment are shown by dots. The predicted initiator methionine for each protein is shown and stop codons are indicated by an asterisk.

Figure 11A:
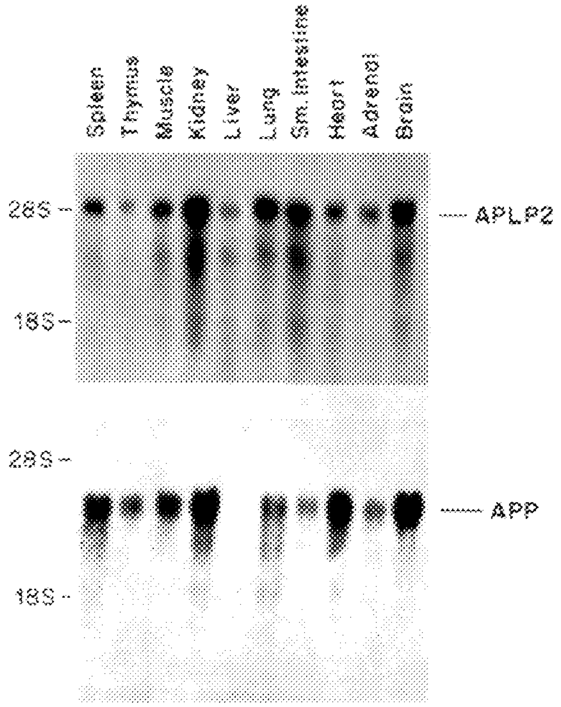
Figure 11B:
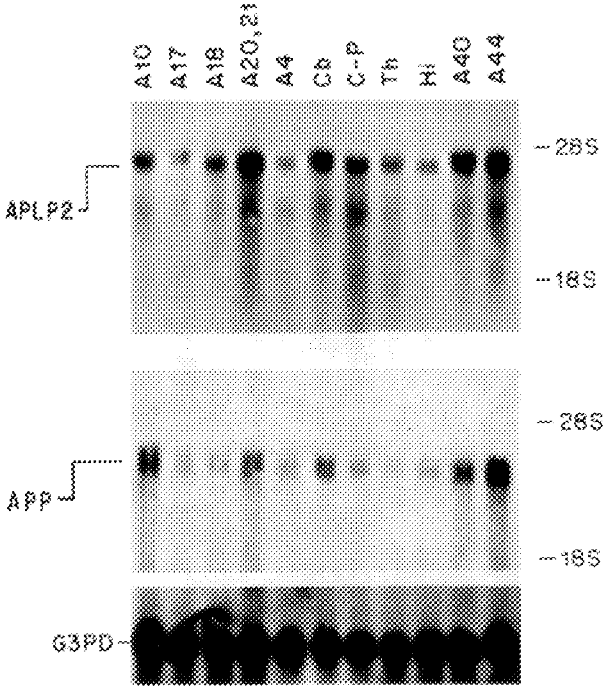

FIGS. 11A–11B. Distribution of human APLP2 gene transcripts. RNA from fetal human tissues (A) or adult human brain (B) was isolated, fractionated, transferred to nylon membranes, and hybridized with radiolabeled probe as previously described (Tanzi et al., *Science* 235:880–884 (1987)). (A) Hybridization of a PCR fragment corresponding to APLP2 amino acids 327 to 490 (APLP2) or a 3' 1.1 kb EcoRI APP cDNA fragment (FB63) were hybridized to RNA (20 μg) from human 20–22 week aborted fetal tissue obtained midtrimester under protocols approved by the institutional review board at Brigham and Women's Hospital. (B) Hybridization of the APLP2 PRC fragment or FB63 to RNA (10 μg) from adult human brain subregions: A10, frontal cortex; A17, striate cortex; A18, extrastriate cortex, A20, 21 temporal association cortex; A4, motor cortex; thalamus-VPL, thalamus-ventral posterolateral nucleus; A40, posterior perisylvian cortex-supramarginal gyri; A44, anterior perisylvian cortex-opercular gyri. Shown beneath FIG. 11B is a control hybridization with a glyceraldehyde-3-phosphate dehydrogenase cDNA (G3PD). The two autoradiograms are from independent hybridizations to the same filter.

Figure 12:
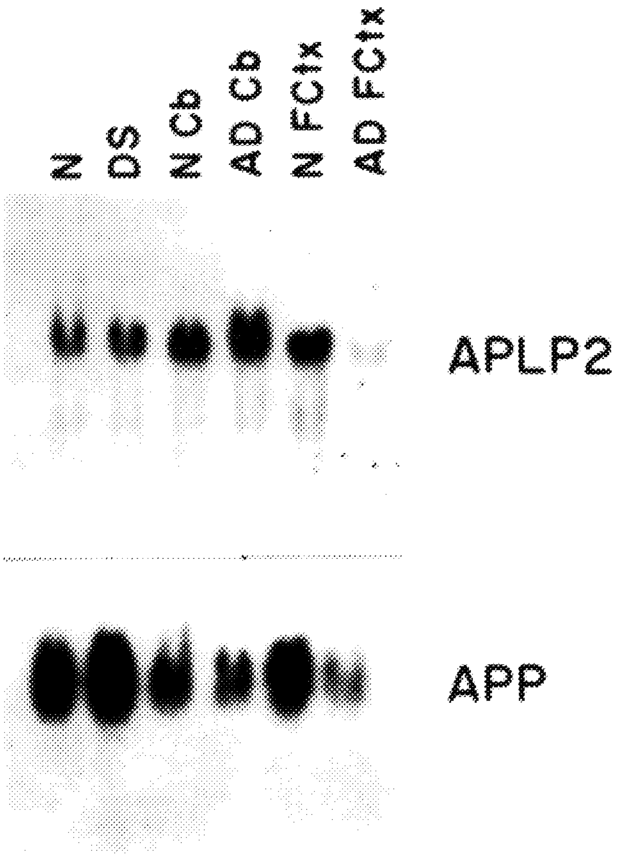

FIG. 12. Northern blot of APLP2 to total RNA from normal and Down syndrome brains, adult normal and ADA cerebellum and frontal cortex. A PCR generated fragment corresponding to APLP2 amino acid 327 to 490 and FB63 (APP) were hybridized to total RNA (25 μg) from 19-week normal (N) and Down syndrome (DS) brains, adult normal (N Cb) cerebellum, and adult normal (N FCtx) and AD (AD FCtx) frontal cortex. The two autoradiograms are from independent hybridizations to the same filter.

Figure 13A:
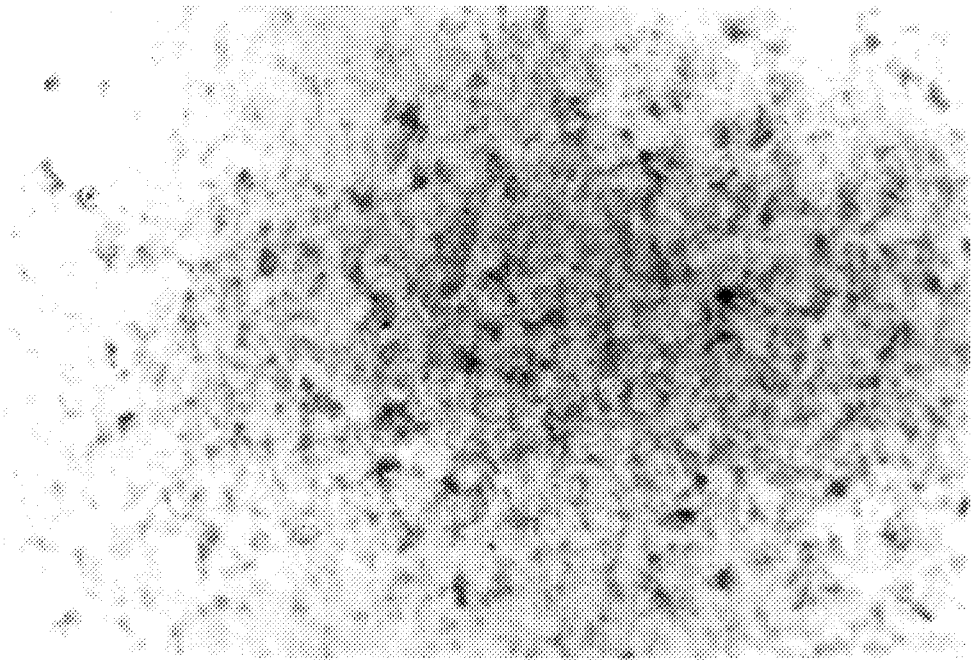
Figure 13B:
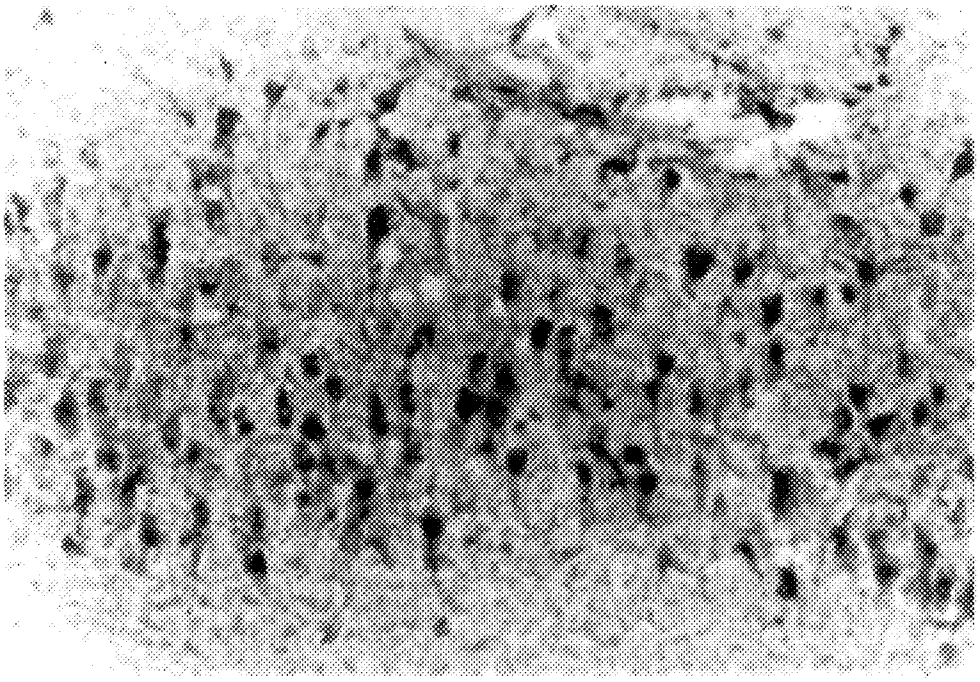

FIGS. 13A–13B. Nonisotopic in situ localization of APLP2-oligonucleotide. (A) In situ hybridization using a 45-mer specific for APLP2 (corresponding to amino acids 74–88 in FIGS. 9A–9B) reveals staining of CA1 pyramidal neurons. The probe was end-labeled with biotin-21-dUTP using 3' terminal transferase and visualized by avidin-biotin-peroxidase reaction (Tanzi et al., *Mol. Brain Res.*:in press; Hyman et al., *Mol. Brain Res.*:in press; Wasco et al., *Alzheimer's disease and related disorders* 1992: selected communications (in press)). (B) a negative control 45-mer corresponding to the other strand of the same region of APLP2 shows no significant staining. Magnification=16×.3.

DETAILED DESCRIPTION OF THE INVENTION

I. Definitions

To aid in the understanding of the specification and claims, including the scope to be given such terms, the following definitions are provided.

Gene. By the term "gene" is intended a DNA sequence which encodes through its template or messenger RNA a sequence of amino acids characteristic of a specific peptide. Further, the term includes intervening, non-coding regions, as well as regulatory regions, and can include 5' and 3' ends.

Gene sequence. The term "gene sequence" is intended to refer generally to a DNA molecule. As used herein, the term is meant to include both a DNA molecule which contains one or more genes, or gene fragments, as well as a DNA molecule which contains a non-transcribed or non-translated sequence. The term is further intended to include any combination of gene(s), gene fragment(s), non-transcribed sequence(s) or non-translated sequence(s) which are present on the same DNA molecule.

The present sequences may be derived from a variety of sources including DNA, cDNA, synthetic DNA, RNA, or combinations thereof. Such gene sequences may comprise genomic DNA which may or may not include naturally occurring introns. Moreover, such genomic DNA may be obtained in association with promoter regions or poly A sequences. The gene sequences, genomic DNA or cDNA may be obtained in any of several ways. Genomic DNA can be extracted and purified from suitable cells, such as brain cells, by means well known in the art. Alternatively, mRNA can be isolated from a cell and used to produce cDNA by reverse transcription or other means.

cDNA. The term "cDNA" includes genes from which the intervening sequences have been removed.

Recombinant DNA. By the term "recombinant DNA" is meant a molecule that has been recombined by in vitro splicing cDNA or a genomic DNA sequence.

Cloning Vehicle. A plasmid or phage DNA or other DNA sequence which is able to replicate in a host cell. The cloning vehicle is characterized by one or more endonuclease recognition sites at which such DNA sequences may be cut in a determinable fashion without loss of an essential biological function of the DNA, which may contain a marker suitable for use in the identification of transformed cells. Markers include, for example, tetracycline resistance or ampicillin resistance. The word vector can be used to connote a cloning vehicle.

Expression Control Sequence. A sequence of nucleotides that controls or regulates expression of structural genes when operably linked to those genes. They include the lac systems, the tip system major operator and promoter regions of the phage lambda, the control region of fd coat protein and other sequences known to control the expression of genes in prokaryotic or eukaryotic cells.

Expression vehicle. A vehicle or vector similar to a cloning vehicle but which is capable of expressing a gene which has been cloned into it, after transformation into a host. The cloned gene is usually placed under the control of (i.e., operably linked to) certain control sequences such as promoter sequences. Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Functional Derivative. A "functional derivative" of APLP is a protein which possesses a biological activity (either functional or structural) or immunological characteristics that are substantially similar to a biological activity or immunological characteristics of non-recombinant APLP. A functional derivative of APLP may or may not contain post-translational modifications such as covalently linked carbohydrate, depending on the necessity of such modifications for the performance of a specific function. The term "functional derivative" is intended to include the "fragments," "variants," "analogues," "homologues," or "chemical derivatives" of a molecule.

Fragment. A "fragment" of a molecule such as APLP is meant to refer to any variant of the molecule.

Variant. A "variant" of a molecule such as APLP is meant to refer to a molecule substantially similar in structure and biological activity or immunological characteristics to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

Analog. An "analog" of a molecule such as APLP is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

Operator. A DNA sequence capable of interacting with the specific repressor, thereby controlling the transcription of adjacent gene(s).

Promoter. The term "promoter" is intended to refer to a DNA sequence which can be recognized by an RNA polymerase. The presence of such a sequence permits the RNA polymerase to bind and initiate transcription of operably linked gene sequences.

Promoter region. The term "promoter region" is intended to broadly include both the promoter sequences as well as all gene sequences which may be necessary for the initiation of transcription. The presence of a promoter region is, therefore, sufficient to cause the expression of an operably linked gene sequence.

Operably Linked. As used herein, the term "operably linked" means that the promoter controls the initiation of expression of the gene. A promoter is operably linked to sequence of proximal DNA if upon introduction into a host cell the promoter determines the transcription of the proximal DNA sequence or sequences into one or more species of RNA. A promoter is operably linked to a DNA sequence if the promoter is capable of initiating transcription of that DNA sequence.

Prokaryote. The term "prokaryote" is meant to include all organisms without a true nucleus, including bacteria.

Host. The term "host" is meant to include not only prokaryotes, but also such eukaryotes as yeast and filamentous fungi, as well as plant and animal cells. The term includes any organism or cell that is the recipient of a replicable expression vehicle.

Amyloid Precursor-Like Protein (APLP). This term is meant to include any amyloid precursor-like protein, from any species, including APLP1 and APLP2, especially from human brain, Alzheimer's disease human brain, or a synthetic APLP. The present APLP exhibits at least 40% identity at the amino acid level to APP and/or APLP1 and/or APLP2, more preferably at least 50% identity thereto, and contains an N-terminal cysteine-rich region consisting of at least 10 cysteines, more preferably consists of 12 cysteines. The term is also used in this invention to include any analog, homolog, mutant or derivative of a naturally occurring APLP. The term is also meant to include fragments having less than the naturally occurring number of amino acids, such as partial fragments of natural or synthetic APLP which retain the biological or immunological characteristics of the polypeptides specifically disclosed in this application. The term is also used to include any product which comprises the sequence of a naturally occurring APLP, or analog or homolog thereof, together with one or more flanking amino acids, which still have the same biological or immunological characteristics.

The term is also used to include any peptide which comprises the sequence of a naturally-occurring APLP or an analog thereof together with one or more flanking amino acids, which have the same biological (functional or structural) or immunological characteristics.

The present invention pertains both to expression of full-length APLP's (i.e. APLP1 and APLP2), and to the functional derivatives of these proteins. This term also includes genetic alleles of APLP's including APLP1 and APLP2.

Substantially homologous. The term "substantially homologous" as used herein refers to the ability of a first DNA sequence encoding an APLP to hybridize to a second DNA sequence encoding an APLP under stringent conditions, for example, at about 0.1× sodium citrate sodium chloride buffer (SSC) at a temperature of about 65° C. For example, if an APLP variant is substantially homologous to a mouse APLP, a DNA sequence encoding the APLP variant is capable of hybridizing to a DNA sequence encoding the mouse APLP under stringent conditions.

Substantially pure. The term "substantially pure" means that the protein/molecule is essentially free from any other detectable biological constituents.

Animal. The term "animal" is meant to refer to any living creature including mammals, for example, humans.

Having established the amino acid sequence of both APLP1 and APLP2, a nucleotide probe can be constructed which is complementary to the DNA, or mRNA coding for APLP1 or APLP2 or a fragment thereof. This probe can be used as a diagnostic test to determine the presence of APLPs including APLP1 and APLP2.

II. Genetic Engineering of an APLP

This invention comprises the amino acid sequence of APLP1 and APLP2, genetic sequences coding for APLP1 and for APLP2 mRNA, expression vehicles containing the genetic sequences, hosts transformed therewith, recombinant APLP1 and recombinant APLP2, and antisense RNA produced by such transformed host expression. The invention further comprises antibodies directed against APLP1 and APLP2

The process for genetically engineering APLP1 and APLP2 sequences, according to the invention, is facilitated through the cloning of genetic sequences which are capable of encoding the peptide and through the expression of such genetic sequences. As used herein, the term "genetic sequences" is intended to refer to a nucleic acid molecule (preferably DNA). Genetic sequences which are capable of encoding the present APLP proteins are derived from a variety of sources. These sources include genomic DNA, cDNA, synthetic DNA, and combinations thereof. The preferred source of the genomic DNA or mRNA is brain or neuroblastoma cells. Post mortem RNA procedures can be followed to isolate the RNA. See Sajdel-Sulkowska et al., *J. Neurochem.* 40:670–680(1983). The mRNA may then be used to obtain cDNA by techniques known to those skilled in the art. Probes may be synthesized based on the known amino acid sequence of the present APLP proteins (APLP1 and APLP2) by methods known in the art.

The APLP genomic DNA of the invention may or may not include naturally occurring introns. Moreover, such genomic DNA may be obtained in association with the 5' promoter region of the APLP gene sequences and/or with the 3' transcriptional termination region. Further, such genomic DNA may be obtained in association with the genetic sequences which encode the 5' non-translated region of the APLP mRNA and/or with the genetic sequences which encode the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA, may be retained and employed for transcriptional and translational regulation. APLP genomic DNA can be extracted and purified from any brain cell of an animal, including, for example, mice and humans, or from any cell containing human chromosome 19, or from any cell that expresses APLP by means well known in the art (for example, see *Guide to Molecular Cloning Techniques*, S. L. Berger et al., eds., Academic Press (1987)).

Alternatively, APLP mRNA can be isolated from any cell which produces or expresses APLP, and used to produce cDNA by means well known in the art (for example, see *Guide to Molecular Cloning Techniques,* S. L. Berger et al., eds., Academic Press (1987)). Preferably, the mRNA preparation used will be enriched in mRNA coding for APLP, either naturally, by isolation from cells which are producing large amounts of the protein, or in vitro, by techniques commonly used to enrich mRNA preparations for specific sequences, such as sucrose gradient centrifugation, or both.

For cloning into a vector, such suitable DNA preparations (either human genomic DNA or cDNA) are randomly sheared or enzymatically cleaved, respectively, and ligated into appropriate vectors to form a recombinant gene (either genomic or cDNA) library. A DNA sequence encoding APLP or its functional derivatives may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis et al., (In: *Molecular cloning, A Laboratory Manual,* Cold Spring Harbor Laboratories, Cold Spring Harbor, N,Y., (1982)), and are well known in the art.

Libraries containing APLP clones may be screened and an APLP clone identified by any means which specifically selects for APLP DNA such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated APLP product produced by the host containing the clone.

Oligonucleotide probes specific for APLP which can be used to identify clones to this protein can be designed from knowledge of the amino acid sequence of APLP1 or APLP2. The sequence of amino acid residues in a peptide is designated herein either through the use of their commonly employed three-letter designations or by their single-letter designations. A listing of these three-letter and one-letter designations may be found in textbooks such as *Biochemistry,* Lehninger, A., Worth Publishers, New York, N.Y. (1970). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

Because the genetic code is degenerate, more than one codon may be used to encode a particular amino acid (Watson, J. D., In: *Molecular Biology of the Gene,* 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: *Molecular Biology of the Gene,* 3rd Ed., W. A. Benjamin, Inc., Menlo Park, Calif. (1977)), one or more different oligonucleotides can be identified from the amino acid sequence, each of which would be capable of encoding the APLP. The probability that a particular oligonucleotide will, in fact, constitute the actual APLP coding sequence can be estimated by considering abnormal base pairing relationships and the frequency with which a particular codon is actually used (to encode a particular amino acid) in eukaryotic cells. Such "codon usage rules" are disclosed by Lathe et al., *J. Molec. Biol.* 183:1–12 (1985). Using the "codon usage rules" of Lathe, a single oligonucleotide sequence, or a set of oligonucleotide sequences, that contain a theoretical "most probable" nucleotide sequence capable of encoding the APLP sequences is identified.

The suitable oligonucleotide, or set of oligonucleotides, which is capable of encoding a fragment of an APLP gene (or which is complementary to such an oligonucleotide, or set of oligonucleotides) may be synthesized by means well known in the art (see, for example, *Synthesis and Application of DNA and RNA,* S. A. Narang, ed., 1987, Academic Press, San Diego, Calif.) and employed as a probe to identify and isolate the cloned APLP gene by techniques known in the art. Techniques of nucleic acid hybridization and clone identification are disclosed by Maniatis et al. (In: *Molecular Cloning, A Laboratory Manual,* Cold Spring Harbor Laboratories, Cold Spring Harbor, N.Y. (1982)); Berger et al., (In: *Guide to Molecular Cloning Techniques,* Academic Press (1988)); Sambrook et al., (In: *Molecular Cloning, A Laboratory Manual,* Cold Spring Harbor Press, Cold Spring Harbor, N.Y., 2d ed. (1989); and by Hames et al. (In: *Nucleic Acid Hybridization, A Practical Approach,* IRL Press, Washington, D.C. (1985)), which references are herein incorporated by reference. Those members of the above-described gene library which are found to be capable of such hybridization are then analyzed to determine the extent and nature of the APLP encoding sequences which they contain.

To facilitate the detection of the desired APLP DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby et al., *J. Mol. Biol.* 113:237 (1977) and by T4 DNA polymerase replacement synthesis as described in, for example, Deen et al., *Anal. Biochem.* 135:456 (1983).

Alternatively, polynucleotides are also useful as nucleic acid hybridization probes when labeled with a non-radioactive marker such as biotin, an enzyme or a fluorescent group. See, for example, Leary et al., *Proc. Natl. Acad. Sci. USA* 80:4045 (1983); Renz et al., *Nucl. Acids Res.* 12:3435 (1984); and Renz, M., EMBO J. 6:817 (1983).

Thus, in summary, the actual identification of APLP sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing an APLP (i.e. APLP1 or APLP2) gene.

In an alternative way of cloning an APLP gene, a library is prepared using an expression vector, by cloning DNA or, more preferably cDNA prepared from a cell capable of expressing an APLP, into an expression vector. The library is then screened for members which express the APLP, for example, by screening the library with antibodies to the protein.

The above discussed methods are, therefore, capable of identifying genetic sequences which are capable of encoding an APLP or fragments of this protein. In order to further characterize such genetic sequences, and, in order to produce the recombinant protein, it is desirable to express the proteins which these sequences encode. Such expression identifies those clones which express proteins possessing characteristics of an APLP. Such characteristics may include the ability to specifically bind an APLP antibody and the ability to elicit the production of antibody which are capable of binding to an APLP.

III. Expression of an APLP and Its Functional Derivatives

To express an APLP, transcriptional and translational signals recognizable by an appropriate host are necessary. The cloned APLP encoding sequences, obtained through the methods described above, and preferably in a double-stranded form, may be operably linked to sequences controlling transcriptional expression in an expression vector, and introduced into a host cell, either prokaryote or eukaryote, to produce recombinant APLP or a functional derivative thereof. Depending upon which strand of the APLP encoding sequence is operably linked to the sequences controlling transcriptional expression, it is also possible to express APLP antisense RNA or a functional derivative thereof.

Expression of the APLP in different hosts may result in different post-translational modifications which may alter the properties of the APLP. The present invention encompasses the expression of the APLP, or a functional derivative thereof, in eukaryotic cells, and especially mammalian, insect and yeast cells. Especially preferred eukaryotic hosts are mammalian cells either in vivo, in animals or in tissue culture. Mammalian cells provide post-translational modifications to recombinant APLP which include folding and/or glycosylation at sites similar or identical to that found for a native APLP. Most preferably, mammalian host cells include brain and neuroblastoma cells.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as an APLP encoding sequence and a promoter region sequence linked to the 5' end of the encoding sequence) are said to be operably linked if induction of promoter function results in the transcription of the APLP encoding sequence mRNA and if the nature of the linkage between the two DNA sequences does not (1) result in the introduction of a frame-shift mutation, (2) interfere with the ability of the expression regulatory sequences to direct the expression of the APLP mRNA, antisense RNA, or protein, or (3) interfere with the ability of the APLP template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene.

Expression of the APLP in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer et al., *J. Mol. Appl. Gen.* 1:273–288 (1982)); the TK promoter of Herpes virus (McKnight, S., *Cell* 31:355–365 (1982)); the SV40 early promoter (Benoist et al., *Nature* (London) 290:304–310 (1981)); in yeast, the yeast gal4 gene promoter (Johnston et al., *Proc. Natl. Acad. Sci. USA* 79:6971–6975 (1982); Silver et al., *Proc. Natl. Acad. Sci. USA* 81:5951–5955 (1984)) or a glycolytic gene promoter may be used.

As is widely known, translation of eukaryotic mRNA is initiated at the codon which encodes the first methionine. For this reason, it is preferable to ensure that the linkage between a eukaryotic promoter and a DNA sequence which encodes an APLP, or a functional derivative thereof, does not contain any intervening codons which are capable of encoding a methionine. The presence of such codons results either in a formation of a fusion protein (if the AUG codon is in the same reading frame as the APLP encoding DNA sequence) or a frame-shift mutation (if the AUG codon is not in the same reading frame as the APLP encoding sequence).

If desired, a fusion product of an APLP may be constructed. For example, the sequence coding for APLP may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., metabolite. Also of interest are constructs wherein APLP mRNA and antisense RNA are provided in a transcribable form, but with different promoters or other transcriptional regulatory elements such that induction of APLP mRNA expression is accompanied by repression of antisense RNA expression, and/or repression of APLP mRNA expression is accompanied by induction of antisense RNA expression.

Translational signals are not necessary when it is desired to express APLP antisense RNA sequences.

If desired, the non-transcribed and/or non-translated regions 3' to the sequence coding for APLP can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells. Where the native expression control sequence signals do not function satisfactorily host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert an APLP DNA construct into the host cell chromosomal DNA, or to allow it to exist in an extrachromosomal form.

If the APLP DNA encoding sequence and an operably linked promoter is introduced into a recipient eukaryotic cell as a non-replicating DNA (or RNA) molecule, which may either be a linear molecule or a closed covalent circular molecule which is incapable of autonomous replication, the expression of the APLP may occur through the transient expression of the introduced sequence.

Genetically stable transformants may be constructed with vector systems, or transformation systems, whereby APLP DNA is integrated into the host chromosome. Such integration may occur de novo within the cell or, in a most preferred embodiment, be assisted by transformation with a vector which functionally inserts itself into the host chromosome, for example, with retroviral vectors, transposons or other DNA elements which promote integration of DNA sequences in chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example, the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein et al., *Miami Wntr. Symp.* 19:265–274 (1982); Broach, J. R., In: *The Molecular Biology of the Yeast Saccharomyces: Life Cycle and Inheritance,* Cold Spring Harbor Laboratory, Cold Spring Harbor, N.Y., pp. 445–470 (1981); Broach, J. R., *Cell* 28:203–204 (1982); Bollon et al., *J. Clin. Hematol. Oncol.* 10:39–48 (1980); Maniatis, T., In: *Cell Biology: A Comprehensive Treatise,* Vol. 3, "Gene Expression," Academic Press, N.Y., pp. 563–608 (1980)), and are commercially available. For example, mammalian expression vector systems which utilize the MSV-LTR promoter to drive expression of the cloned gene, and in which it is possible to cotransfect with a helper virus to amplify plasmid copy number, and integrate the plasmid into the chromosomes of host cells have been described (Perkins et al., Mol. *Cell Biol.* 3:1123 (1983); Clontech, Palo Alto, Calif.).

Once the vector or DNA sequence containing the construct(s) is prepared for expression, the DNA construct(s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of an APLP, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, affinity chromatography, electrophoresis, or the like.

The APLP DNA encoding sequences, obtained through the methods above, will provide sequences which, by definition, encode an APLP and which may then be used to obtain APLP antisense RNA genetic sequences as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of an APLP antisense RNA in the transformed cell. Antisense RNA and its expression may be used to interact with an endogenous APLP DNA or RNA in a manner which inhibits or represses transcription or translation of an APLP gene in a highly specific manner. Use of antisense RNA probes to block gene expression is discussed in Lichtenstein, C., *Nature* 333:801–802 (1988). For example, such probes can be used to block the expression of an APLP when the expression is aberrant.

IV. Construction and Identification of Antibodies to an APLP

In the following description, reference will be made to various methodologies well-known to those skilled in the art of immunology. Standard reference works setting forth the general principles of immunology include the work of Catty, D., (*Antibodies, A Practical Approach,* Vol. 1, IRL Press, Washington, D.C. (1988)); Klein, J., (*Immunology: The Science of Cell-Noncell Discrimination,* John Wiley & Sons, New York (1982)); Kennett et al., (*Monoclonal Antibodies, Hybridoma: A New Dimension in Biological Analyses,* Plenum Press, New York (1980)); Campbell, A. ("Monoclonal Antibody Technology," In: *Laboratory Techniques in Biochemistry and Molecular Biology,* Vol. 13 (Burdon, R., et al., eds.), Elsevier, Amsterdam (1984)); and Eisen, H. N. (In: *Microbiology,* 3rd ed. (Davis, B. D., et al., Harper & Row, Philadelphia (1980)).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and $F(ab)_2$ fragments) which are capable of binding an antigen. Fab and $F(ab)_2$ fragments lack the Fc fragment of intact antibody, clear more rapidly from the circulation, and may have less non-specific tissue binding of an intact antibody (Wahl et al., *J. Nucl. Med.* 24:316–325 (1983)).

The antibodies of the present invention have specificity to one or more epitopes present on an APLP (i.e. APLP1 or APLP2) peptide. The antibodies of the invention can be polyclonal or monoclonal, provided that they are made with the present polypeptide or fragment thereof as an immunogen. Both of these types of antibodies can be utilized in the multiple applications described herein below.

The present antibodies can be used to detect the presence of an APLP in a biological specimen such as body fluid, serum, or a tissue sample. An APLP can be detected by contacting the sample with an imaging-effective amount of the present detectably labeled antibody and detecting the label, thereby establishing the presence of the APLP in the sample. The sample can be a tissue section, serum, or other biological specimen, or detection can be carried out by imaging in vivo. An APLP can also be detected by known immunoassay techniques, including, for example, RIA, ELISA, etc., using the present antibodies.

The antibodies of the present invention are prepared by any of a variety of methods. For example, cells expressing an APLP, or a fragment thereof, can be administered to an animal in order to induce the production of sera containing polyclonal antibodies that are capable of binding the APLP. For example, an APLP fragment is chemically synthesized and purified by HPLC to render it substantially free of contaminants. Such a preparation is then introduced into an animal in order to produce polyclonal antisera of high specific activity.

Polyclonal antibodies can be generated n any suitable animal including, for example, mice, rabbits or goats. The present peptide can be injected by itself or linked to appropriate immunoactivating carriers, such as Keyhole's limpet hemocyanin (KLH). See *Antibodies, A Practical Handbook,* Vols. I and II, D. Catty, ed., IRL Press, Washington, D.C. (1988).

Monoclonal antibodies can be prepared in various ways using techniques well understood by those having ordinary skill in the art. For example, monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas,* Elsevier, N. Y., pp. 563–681 (1981)); *Monoclonal Antibodies—Hybridomas: A New Dimension in Biological Analysis,* edited by Roger H. Kennett et al., published by Plenum Press (1980). In general, such procedures involve immunizing an animal with an APLP antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands et al., *Gastroenterology* 80:225–232 (1981), which reference is herein incorporated by reference. The hybridoma cells obtained through such a selection are then assayed to identify clones which secrete antibodies capable of binding the APLP antigen.

Through application of the above-described methods, additional cell lines capable of producing antibodies which recognize epitopes of an APLP can be obtained.

For example, additional hybridomas which produce monoclonal antibodies which enable the detection of an APLP can be easily produced and isolated with minimal screening. Hybridomas producing monoclonal antibodies specific for epitopes which are found on an APLP are most effectively produced by first immunizing an animal from which hybridomas can be produced such as, for example, a Balb/c mouse, with initial subcutaneous injections of Freund's adjuvant, followed by booster injections within a few days. The fusion can be carried out using any of the techniques commonly known to those of ordinary skill in the art. The screening of the hybridomas to determine which ones are producing monoclonal antibodies specific for the present peptide is straightforward and can be done either in a standard ELISA or RIA format. For example, in an RIA screening format the culture supernatant, or ascites fluid from a hybridoma producing monoclonal antibody is reacted with $^{125}$I-peptide.

Of special interest to the present invention are antibodies which are produced in humans, or are "humanized" (i.e. non-immunogenic in a human) by recombinant or other technology such that they will not be antigenic in humans, or will be maintained in the circulating serum of a recipient for a longer period of time.

Humanized antibodies may be produced, for example by replacing an immunogenic portion of an antibody with a corresponding, but nonimmunogenic portion (i.e. chimeric antibodies) (Robinson et al., International Patent Publication PCT/US86/02269; Akira et al., European Patent Application 184,187; Taniguchi, M., European Patent Application 171, 496; Morrison et al., European Patent Application 173,494; Neuberger et al., PCT Application WO 86/01533; Cabilly et al., European Patent Application 125,023; Better et al., *Science* 240:1041–1043 (1988); Liu et al., *Proc. Natl. Acad. Sci. USA* 84:3439–3443 (1987); Liu et al., *J. Immunol.* 139:3521–3526 (1987); Sun et al., *Proc. Natl. Acad. Sci. USA* 84:214–218 (1987); Nishimura et al., Canc. Res. 47:999–1005 (1987); Wood et al., *Nature* 314:446–449 (1985)); Shaw et al., *J. Natl.Cancer Inst.* 80:1553–1559 (1988). General reviews of "humanized" chimeric antibodies are provided by Morrison, S. L. (*Science,* 229:1202–1207 (1985)) and by Oi et al., *BioTechniques* 4:214 (1986)).

Suitable "humanized" antibodies can be alternatively produced as described by Jones et al., *Nature* 321:552–525 (1986); Verhoeyan et al., *Science* 234:1534 (1988), and Beidler et al., *J. Immunol.* 141:4053–4060 (1988).

Antibodies against both highly conserved and poorly conserved regions of an APLP are useful for studies on the control of biosynthesis and catabolism of an APLP in normal and pathologic conditions. Further, these antibodies can be used clinically to monitor the progress of disease states wherein the expression of an APLP is aberrant.

The antibodies of the present invention can be utilized in immunoassays for the detection of an APLP wherever it may occur, including fluid, semi-fluid, or tissue samples, serum, or other biological specimen. The immunoassays can be competitive or sandwich, or as is otherwise well known and they all depend on the formation of antibody-antigen immune complex. These assays are well known to those of skill in the art.

For purposes of the assays, the antibodies can be immobilized or labeled. There are many carriers to which the antibodies can be bound for immobilization and which can be used in the present invention. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding the antibodies, or will be able to ascertain such, using routine experimentation.

Depending on the particular embodiment of the invention, one or more of the antibodies will be coupled with a detectable label such as an enzyme, radioactive isotope, fluorescent compound, chemiluminescent compound, or bioluminescent compound.

Those of ordinary skill in the art will know of other suitable labels for binding to the antibodies or will be able to ascertain such using routine experimentation. Furthermore, the binding of these labels to the antibodies can be done using standard techniques commonly known to those of ordinary skill in the art.

The antibodies can be bound to an enzyme. This enzyme, in turn, when later exposed to its substrate will react to the substrate in such a manner as to produce a chemical moiety which can be detected, as, for example, spectrophotometric or fluorometric means. Examples of enzymes that can be used to detectably label are malate dehydrogenase, staphylococcal nuclease, delta-5-steroid isomerase, yeastalcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholinesterase.

The presence of an antibody can also be detected by labeling it with a radioactive isotope. The presence of the radioactive isotope could then be determined by such means as the use of a gamma counter or a scintillation counter. Isotopes which are particularly useful are $^{3}$H, $^{125}$I, $^{32}$P, $^{35}$S, $^{14}$C, $^{51}$Cr, $^{36}$C, $^{57}$Co, $^{58}$Co, $^{59}$Fe, $^{75}$Se, and $^{152}$Eu.

It is also possible to detect the presence of the antibody by labeling it with a fluorescent compound. When the fluorescently labeled antibody is exposed to light of the proper wavelength, its presence can then be detected due to fluorescence of the dye. among the most important fluorescent labeling compounds are fluorescein isothiocyanate, rhodamine, phycoerythrin, phycocyanin, allophycocyanin, o-phthaldehyde, and fluorescamine.

Another way in which the antibody can be detectably labeled is by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, aromatic-acridinium ester, imidazole, acridinium salt, and oxalate ester.

Likewise, a bioluminescent compound may also be used to label the antibody. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

The antibodies for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in the method.

For example, one of the container means may comprise a first antibody bound to an insoluble or partly soluble carrier. A second container may comprise soluble, detectably-labeled second antibody, in lyophilized form or in solution. The carrier means may also contain a third container means comprising a detectably-labeled third antibody in lyophilized form or in solution. Such a kit can be used for sandwich assays. See, e.g., David et al., U.S. Pat. No. 4,376,110 herein incorporated by reference.

In addition, the carrier means may also contain a plurality of containers each of which comprises different, predetermined amounts of known APLP. These latter containers can then be used to prepare a standard curve into which can be interpolated the results obtained from the sample containing the unknown amount of an APLP antigen.

Imaging can be carried out in vitro or in vivo. In vivo imaging can be done with the labels mentioned previously. In vivo imaging is done with diagnostically effective labeled antibodies. The term "diagnostically effective" means that the amount of detectably labeled antibody administered is sufficient to enable detection of the site of APLP presence when compared to a background signal.

Generally, the dosage of detectably labeled antibody for diagnosis will vary depending on considerations such as age, condition, sex, and extent of disease in the patient, counterindications, if any, and other variables, to be adjusted by the individual physician. Dosage can very from 0.01 mg/kg to 2,000 mg/kg, preferably 0.1 mg/kg to 1,000 mg/kg.

The term "diagnostically labeled" means that the immunoglobulin has attached to it a diagnostically detectable label.

There are many different imaging labels and methods of labeling known to those of ordinary skill in the art. Examples of the types of labels which can be used in the present invention include radioactive isotopes and paramagnetic isotopes.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140–200 keV range, which may be readily detected by conventional gamma cameras.

For in vivo diagnosis, radionuclides may be bound to antibody either directly or indirectly by using an intermediary functional group. Intermediary functional groups which are often used to bind radioisotopes which exist as metallic ions to antibody are diethylenetriaminepentaacetic acid (DTPA) and ethylenediaminetetracetic acid (EDTA). Typical examples of metallic ions which can be bound to immunoglobulins are $^{99m}$Tc, $^{123}$I, $^{111}$In, $^{131}$I, $^{97}$Ru, $^{67}$Cu, $^{67}$Ga, $^{72}$As, $^{89}$Zr, and $^{201}$T1.

The antibodies used in the method of the invention can also be labeled with paramagnetic isotopes for purposes of in vivo diagnosis. Elements which are particularly useful (as in magnetic resonance imaging (MRI) techniques) in this manner include $^{157}$Gd, $^{55}$Mn, $^{162}$Dy, $^{52}$Cr, and $^{56}$Fe.

Preparations of the imaging antibodies for parenteral administration include sterile aqueous or non-aqueous solutions, suspensions, and emulsions. Examples of non-aqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, and inert gases and the like. See, generally, *Remington's Pharmaceutical Science,* 16th ed., Mac Eds. 1980.

Experimental

Example 1

Materials and Methods

Neuroblastoma NB2A cells were maintained as previously described (Magendantz et al., *Proc. Natl. Acad. Sci. USA* 82:6581–6585 (1985)). Radionucleotides were obtained from New England Nuclear and Amersham. Restriction enzymes were obtained from New England Biolabs and PCR reagents from Perkin-Elmer.

Screening of λgt11 Libraries. General techniques for preparing and screening libraries are disclosed in Maniatis et al., *Molecular Cloning, A Laboratory Manual,* Cold Spring Harbor Laboratory, Cold Spring Harbor, N.Y., 2d ed. (1989). Three different libraries were used to obtain mouse brain cDNA clones in λgt11. A random primed and an oligo-dT primed library were obtained from Clontech. An oligo-dT primed library was obtained from Stratagene. Libraries were screened by hybridization to nitrocellulose (BA85, Schleicher and Schuell) or Nylon (Hybond-N, Amersham) according to standard procedures using cDNA that was labeled by random priming (Feinberg et al., *Anal. Biochem.* 132:6–13 (1983)). Positive clones were sized by PCR amplification of the λgt11 insert using primers 1218 and 1222 from New England Biolabs.

Recombinant DNA Techniques

DNA fragments were subcloned into pBluescript (Stratagene) or M13 (New England Biolabs) vectors and both strands were sequenced with Sequenase (U.S. Biochemical) according to the manufacturer's instructions. Sequence analyses were done using the UWGCG programs at the Whitaker College Computing Facility at MIT.

RACE Procedure for Obtaining 5' cDNA Extensions

The RACE (Rapid Amplification of cDNA Ends) procedure that was used is a combination of the methods of Frohman et al. (Frohman et al., *Proc. Natl. Acad. Sci. USA* 85:8998–9002 (1988)) and Ohara et al. (Ohara et al., *Proc. Natl. Acad. Sci. USA* 86:5673–5677 (1989)). For the RACE procedure, the primers were the complements of nucleotides 699–719 and 672–692 of the sequence presented in FIGS. 2A–2E RACE products were subcloned into pBluescript, screened by hybridization to the 5' 120 bp EcoRI-PstI fragment of 69A and positive clones were sequenced.

RNA Analysis

PolyA+RNA was prepared as in Badley et al. (Badley et al., *BioTechniques* 6:114–116 (1988)), using oligo-dT beads (Collaborative Research). For Northern blot analysis the RNA was separated on an agarose gel containing formaldehyde, transferred to nylon (BioTrace, Gelman Sciences) according to standard methods (Sambrook et al., *Molecular Cloning* (*A Laboratory Manual*), Cold Spring Harbor Laboratory, (1989)), and crosslinked to the nylon using a UV Crosslinker (Stratagene). The blots were hybridized and washed according to the method of Church and Gilbert (Church et al., J. *Cell Biol.* 107:1765–1772 (1988)). The molecular weight of the transcripts was determined by using RNA molecular weight markers.

Production Antisera to an APLP Peptide.

A peptide with the sequence QQLRELQRH (SEQ ID NO:1) was obtained from the Biopolymers laboratory of the Howard Hughes Medical Institute and Center for Cancer Research at MIT. 20 mg of the peptide was conjugated to KLH essentially as described in Marcantonio, C. G., and Hynes, R. O., *J. Cell Biol.* 107:1765–1772 (1988), and the immunization of four New Band white rabbits was carried out as described in Schatz et al. (Schatz et al., *Mol. Cell Biol.* 7:3799–3805 (1987)).

Protein Preparation

Protein from neuroblastoma cells was isolated by rinsing the cells with PBS followed by lysing the cells in SDS sample buffer and boiling. Protein from mouse brain was isolated by homogenizing one brain in 1 ml of RIPA buffer (50 nM Tris pH 7.4, 150 mM NaCl, 5 mM EDTA, 1% Triton X-100, 1% Na deoxycholate, 0.1% SDS and protease inhibitors). The homogenate was spun in an Eppendorf centrifuge for 30 minutes at 4° C., combined with SDS sample buffer and boiled.

β-galactosidase Fusion Protein Preparation

A β-galactosidase-APLP1 fusion protein was constructed using standard techniques (Sambrook et al., *Molecular Cloning* (*A Laboratory Manual*), Cold Spring Harbor Laboratory, (1989)). An EcoRI-EcoRI fragment from a λgt11 clone containing 666 nucleotides of the 3' coding portion (nucleotides 1380–2046 of FIGS. 2A–2E), and 258 nucleotides of the untranslated region of the APLP (nucleotides 2047–2305 of FIGS. 2A–2E) was ligated into the EcoRI site of a pUEX5 vector.

To prepare total protein lysates from bacteria containing these plasmids, an overnight culture, diluted 1:10 into L-broth plus ampicillin, was grown for 1.5–2 hours at 300, then induced at 42° (or left at 30° for uninduced samples) for 2.5–3 hours. The bacteria were then spun down, resuspended in 50% SDS sample buffer containing protease inhibitors and sonicated to shear chromosomal DNA.

Western Blot Analysis

Protein samples were subjected to polyacrylamide gel electrophoresis, transferred to nitrocellulose and probed with rabbit antibodies and $^{125}$I-labelled protein A essentially as described in Birgbauer (Birgbauer et al., *J. Cell Biol.* 109:1609–1620(1989)).

Immunofluorescence

Neuroblastoma cells were plated onto glass coverslips approximately forty eight hours before fixation. Twenty four hours before fixation, the concentration of fetal calf serum in the medium of neuroblastoma cells was changed from 10% to 0.1% to induce neurite extension. Twenty minutes before fixation, concanavalin A was added to 20 mg/ml to encourage cell adhesion to the coverslips. Cells were fixed in 3.7% formaldehyde/PBS, permeabilized in acetone and blocked for 30 minutes at 37° in PBS containing 1% calf serum. Primary antibody was diluted into the blocking buffer, applied to the cells for 30 minutes and visualized with FITC conjugated goat antirabbit antibody. Cells were observed and photographed using a Zeiss Axioplan microscope. For the peptide competition experiment, the peptide was preincubated with the primary antibody in blocking buffer for 30 minutes before adding it to the cells (Donaldson et al., *J. Cell Biol.* 111:2295–2306 (1990) and Moremen et al., *J. Biol. Chem.* 260:6654–6662 (1985)).

Results

Identification and Cloning of APLP1

In a screen for cDNA clones encoding a microtubule-associated protein (MAP), a clone was isolated from a mouse brain cDNA library (Stratagene) which was found to have an open reading frame (ORF) homologous to that of APP. The probe that was used to screen was an antibody elicited against MAP. APLP1 is not related to any known MAP.

The cDNA clone in which the APP homology was originally identified contained a portion of the C-terminal coding sequence as well as a portion of the 3' untranslated region. To extend the APLP1 ORF in the 5' direction, probes were used from the 5'-most regions of available cDNA clones to screen two Clontech λgt11 libraries. Repetitive screens using progressively more upstream probes resulted in the isolation of a 1.8 kb cDNA clone, 69A (FIG. 1), whose 5' terminus has an EcoRI site that is present in the coding sequence of APLP1 and is the result of an EcoRI site that escaped methylation during construction of the cDNA library.

Although screening of the cDNA libraries with probes derived from the 5' end of 69A failed to identify any more APLP1 clones, the use of a variation of the RACE procedure developed by Frohman et al. (Frohman et al., *Proc. Natl. Acad. Sci. USA* 85:8998–9002 (1988)) and by Ohara et al. (Ohara et al., *Proc. Natl. Acad. Sci. USA* 86:5673–5677 (1989)) did enable the isolation of several independent, overlapping cDNA clones that extend the APP homology past the 5' EcoRI site of 69A. The longest clone, J (FIG. 1), did not contain an initiator methionine.

The sequence information obtained via the RACE procedure was used to create PCR primers and amplify the 5'-most 100 base pairs encoded by clone J. This PCR product was used as a probe in a screen of a Stratagene mouse brain cDNA library that successfully identified a number of full length APLP1 clones. Two of these were sequenced to obtain the final 313 5' nucleotides as well as the polyadenylation signal and the poly A tail of the APLP1 cDNA. The predicted initiator methionine is in agreement with the eukaryotic consensus initiation sequence (Kozak, M., *Nucl. Acids Res.* 12:857–872 (1984).

APLP1 is Related to APP

The 2361 nucleotides of the cDNA sequence encode an open reading frame of 653 amino acids as is shown in FIGS. 2A–2E (SEQ ID NO:3). The protein is predicted to have a short intracellular C-terminus of 46 amino acids, a membrane spanning domain of 23 amino acids, and a larger extracellular N-terminus. The predicted amino acid sequence and the overall structure of APLP1 is similar to those of APP, which resembles an integral membrane protein (Kang et al., *Nature* 325:733–736 (1987)). The alignment of the two amino acid sequences shown in FIGS. 3A–3B reveals that overall APLP is 42% identical and 64% similar to APP.

APLP1 is a Member of a Family of APP-like Proteins

The identities between APLP1 and APP are concentrated in three distinct regions (FIGS. 4A–4B), where the proteins are 47, 54 and 56% identical and 67, 73 and 74% similar. These same three regions have been shown previously to be shared between APP and a Drosophila APP-like protein (Drosophila APPL), and have been termed the extracellular I (EI), extracellular II (EII) and cytoplasmic (C) domains by these investigators (Rosen et al., *Proc. Natl. Acad. Sci. USA* 86:2478–2482 (1989)). The cytoplasmic domain homology is also present in a partial cDNA clone that has been isolated from a rat testis library (Yan et al., *Proc. Natl. Acad. Sci. USA* 87:2405–2408 (1990)). Only APP contains the βA4 sequence that is found in amyloid plaques.

FIGS. 4A–4B shows the domain alignment of the four proteins mentioned above. A similar alignment has been shown for the relationship between the Drosophila APPL1 and APP (Rosen et al., *Proc. Natl. Acad. Sci. USA* 86:2478–2482 (1989)). The testis cDNA is included only in the C domain comparison since only this portion of the predicted amino acid sequence is known (Yan et al., *Proc. Natl. Acad. Sci. USA* 87:2405–2408 (1990)). EI begins at amino acid 21 in the APLP1 open reading frame and spans 136 amino acids. Overall, 102 of these 136 amino acids (75%) are either identical to amino acids in the respective positions of APP or Drosophila APPL, or they are the same in all three proteins. The most striking conservation within this region is that of 12 cysteine residues in all three of the sequences. There are also two regions of amino acids that are particularly well conserved (underlined in FIGS. 4A–4B), as is an unusually acidic region composed of glutamic and/or aspartic acids that spans amino acids 237–271 in the APLP1 sequence (FIGS. 2A–2E).

EII spans 130 amino acids in the mouse APLP1 sequence. 93 of the 130 APLP1 amino acids (71%) are identical to either one or both of their counterparts in APP or the Drosophila APPL sequences. This region also contains conserved N-glycosylation site in all 3 proteins.

The third domain encompasses the C-terminal cytoplasmic region of all of the proteins, including the predicted amino acid sequence of the rat testis cDNA. The conservation of amino acids among the members of the APP-like family within this domain is particularly strong. Although the four proteins do not share homology within the predicted transmembrane domains (FIGS. 3A–3B Rosen et al., *Proc. Natl. Acad. Sci. USA* 86:2478–2482 (1989); Yan et al., *Proc. Natl. Acad. Sci. USA* 87:2405–2408 (1990)), all of them do contain a 3–4 amino acid span of charged residues (arginine/lysine) at the cytoplasmic face of the membrane (FIGS. 4A–4B). This characteristic is often seen at the membrane-cytoplasmic junction of other proteins, and has been hypothesized to allow for an interaction with phospholipids in the membrane, or to provide a stop transfer signal for membrane bound proteins (Blobel, G., *Proc. Natl. Acad. Sci. USA* 77:1796–1500(1980)).

Northern Blot Analysis

Figure 5:
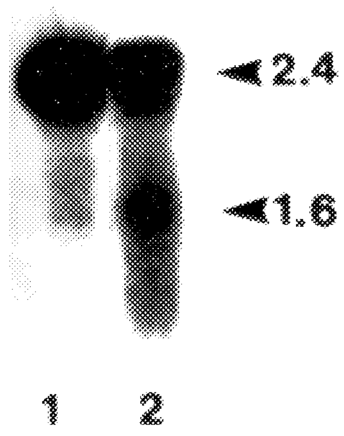
FIG. 5. Northern blots of mouse brain and neuroblastoma RNA. Poly A+RNA (10 μg) from neuroblastoma (lane 1) and mouse brain (lane 2) was separated on agarose gels containing formaldehyde and transferred to nylon as described in Materials and Methods. The blot was probed with DNA corresponding to nucleotides 1482–1995 of the nucleotide sequence shown in FIGS. 2A–2E. Sizes of hybridizing messages in kb are indicated.

FIG. 5 shows autoradiographs of Northern blots containing polyA+RNA from mouse brain and neuroblastoma cells that were probed with DNA corresponding to nucleotides 1791–2305 of FIGS. 2A–2E. These blots reveal that in mouse brain and neuroblastoma cells there are two messages of approximately 2.4 and 1.6 kb that hybridize to this probe. The larger message appears to be present in relatively greater abundance than the smaller message. Because of its size, it is clear that the cDNA that corresponds to the 2.4 kb message, although both messages are consistently seen in Northerns that are probed and washed under stringent conditions. The mouse APLP1 cDNA docs not hybridize to the 3.2 and 3.4 kb APP messages under the conditions used (see Materials and Methods; Kang, J. et al., *Nature* 325:733–736 (1987)).

Generation of Antibodies Against an APLP1 Peptide.

In order to further characterize the protein encoded by the APLP1 cDNA, antibodies were raised to a synthetic peptide which corresponds to a unique sequence of mouse APLP1. The peptide that was used as antigen corresponds to a 9 amino acid segment located near the C-terminus of the APLP1 protein (QQLRELQRH), a region where the four proteins are not homologous.

Figure 6A:
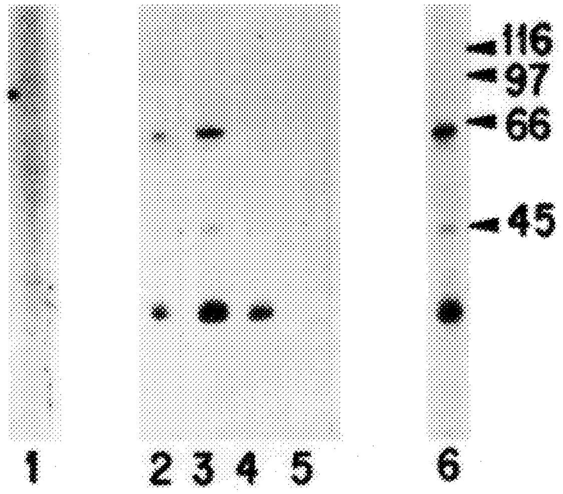
FIGS. 6A–6C. Western Blots using antiserum 301 (See the Example). Mouse brain and neuroblastoma proteins were separated by 7.5% PAGE as described in Materials and Methods.
Figure 6B:
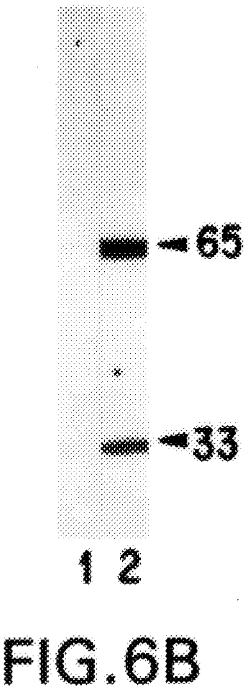

Four rabbits were injected with the peptide as described in Materials and Methods. Two of the four rabbits (301 and 302) produced sera that strongly recognize a 65 kDa mouse brain protein that is not recognized by the appropriate preimmune sera (FIG. 6A). A smaller protein of approximately 33 kDa that is recognized by antiserum 301 may be a proteolytic degradation product of the larger protein. In FIG. 6A, the specificity of the interaction of the antibody with these proteins is demonstrated by the ability to block the binding of antibody 301 to the proteins by preabsorbing with the original peptide (lanes 2–5); an irrelevant peptide has no effect on the interaction of the antibody with either the 65 kDa or 33 kDa protein (lane 6). Antiserum 301 also recognizes a 65 kDa protein present in neuroblastoma cell extracts that is not recognized by preimmune serum (FIG. 6B).

Figure 6C:
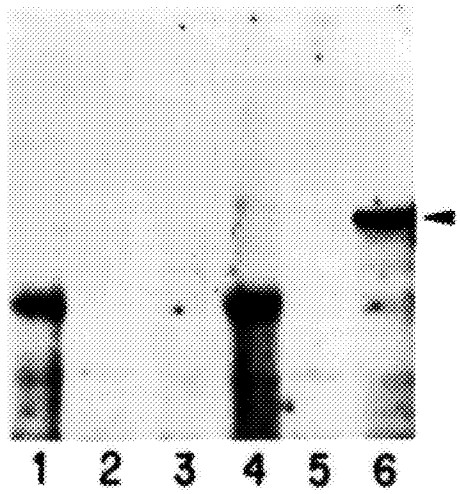

To further confirm the specificity of the 301 antiserum, we determined whether the antiserum would recognize a β-galactosidase fusion protein containing the 222 carboxy-terminal amino acids encoded by the APLP1 cDNA. FIG. 6C shows a Western blot of bacterially produced proteins that were probed with antiserum 301. As can be seen in lane 6 of this figure, antisera 301 does specifically interact with the β-galactidase-APLP1 fusion protein.

There are a number of antibodies that have been generated against the C-terminus of APP. Because the identity between APP and the mouse APLP1 in this region is particularly strong, some of these antisera would also be likely to interact with the mouse APLP1. One of these antisera, R37 (Kang et al., *Nature* 325:733–736 (1987); and Ishii et al., *Neuropatolo. and Appl. Neurobiol.* 15:135–147 (1989)), is directed against the carboxy-terminal 15 amino acids of APP, a region where the two proteins are particularly similar (see FIGS. 4A–4B). R37 does recognize the β-galactosidase-APLP1 fusion protein and a 65 kDa mouse brain protein that comigrates with the 65 kDa protein recognized by antiserum 301 (data not shown). The 15 amino acid sequence used to raise the anti-APP antibody does not overlap the 9 amino acids used to generate antiserum 301. These data suggest that the 65 kDa protein contains two epitopes in common with the APLP1 fusion protein. Antibodies can be made which recognize only APLP1.

Anti-APLP1 Antisera Recognizes a Protein in the Golgi.

The subcellular localization of the protein recognized by antiserum 301 was assayed by immunofluorescence. When neuroblastoma cells are stained with 301, the pattern that is observed is a reticular staining near the nucleus (FIG. 7A and FIG. 7B). Because of 3-dimensional nature of the staining, and the round shape of the cells, the image seen in any one plane of focus appears punctate rather than reticular. An identical pattern is seen with antiserum 302 (data not shown). The pattern itself is reminiscent of Golgi staining, and when these cells are stained with an antibody to a known Golgi enzyme, mannosidase II, a pattern much like that seen with antiserum 301 is observed (FIG. 7C). The inclusion of the original peptide in the antibody incubation inhibited the 301 staining (FIG. 7D). Staining was not seen when preimmune serum was used (FIG. 7E).

Discussion

The present APLP1 cDNA sequence encodes a new member of the APP-like family. The mouse homologue of the human amyloid precursor protein has been cloned previously and is 96.8% identical to the human sequence at the amino acid level (Yamada et al., *Biochem. Biophys. Res. Comm.* 158:906–912 (1987)). Thus, the present APLP1 cDNA, which is 42% identical to the amyloid precursor protein at the amino acid level, is not the mouse homologue of APP and is a distinct, yet related protein.

The two sequences share three domains of homology. The amino acid conservation within these domains include 12 cysteines, an unusually acidic region, a potential N-glycosylation site, a hydrophobic membrane spanning region, and several specific blocks of exact identity. It is clear that the mouse APLP, the Drosophila APPL, the rat testis protein and APP comprise a family of proteins. The extensive conservation of amino acid identity as well as both the overall and specific domain structure within this family of proteins suggests that these proteins share a common function.

There are two potentially interesting observations that can be made concerning the strict conservation of the 7-amino acid sequence located within the cytoplasmic tail of the proteins in the APP-like family (see underlined sequence in the appropriate portion of FIGS. 4A–4B). There is a potential tyrosine phosphorylation site present 8–9 amino acids from the carboxy terminus of all four sequences (Tamkun et al., *Cell 46:271–282* (1986)). APP can be phosphorylated when introduced into transformed embryonic kidney cells (Oltersdorf et al., *J. Biol. Chem.* 265:4492–4497 (1990)) and a peptide containing a portion of the cytoplasmic domain can be phosphorylated on serine and threonine residues in vitro (Gandy et al., *Proc. Natl. Acad. Sci. USA* 85:6218–6221 (1988)), but tyrosine phosphorylation has not yet been demonstrated. Agents that are known to regulate protein phosphorylation appear to affect the rate of proteolytic processing of mature forms of APP (Buxbaum et al., *Proc. Natl. Acad. Sci. USA* 87:6003–6006 (1990)), suggesting that abnormal protein phosphorylation may be involved in the production of βA4. The sequence surrounding this tyrosine also shares homology with the only tyrosine in the α-helical domain that is conserved between several classes of intermediate filaments (Lendahl et al., *Cell 60:585–595* (1990)). The conservation of this potentially phosphorylated tyrosine is intriguing in light of the role that tyrosine phosphorylation is known to play in the regulation of cell growth and differentiation.

The same tyrosine is part of the tetrameric sequence NPxY that is believed to be required for the ligand-independent, coated pit-mediated internalization of the low density lipoprotein receptor (Chen, et al., *J. Biol. Chem.* 265:3116–3123 (1990)). The NPxY sequence is present in the cytoplasmic tails of at least 16 other cell surface receptor molecules-including the β-integrin receptor and members of the EGF receptor family (Chen, et al., *J. Biol. Chem.* 265:3116–3123 (1990)).

The APLP1 cDNA that has been isolated shares at least one epitope with a 65 kDa protein that is present in mouse brain homogenates and neuroblastoma cell extracts, and it shares an epitope with a protein that localizes to the Golgi in neuroblastoma cells. An antiserum that recognizes the Drosophila APPL protein also recognizes a protein in the Golgi (Luo et al., *J. Neurosci* 10:3849–3861 (1990)). In addition, antibodies to the APP give a perinuclear staining pattern suggestive of either Golgi or ER localization when used for immunofluorescence on muscle fibers (Zimmermann et al., *EMBO J.* 7:367–372 (1988)). The N-terminal extracellular portion of both the Drosophila APPL protein and APP can be secreted via cleavage at or near the membrane (Weidman et al., *Cell* 57:115–126 (1989); Zimmermann et al., *EMBO J.* 7:36–372 (1988); and Palmert et al., *Proc. Natl. Acad. Sci. USA* 86:6338–6342 (1989)). Although the normal function of the proteins in the APP family remains cryptic, the present results suggest that APLP1, like APP and the Drosophila APPL may be processed in, or reside in, the (Golgi.

The existence of a family of APP-like proteins implies that these proteins may share a function. The conservation of cysteines at the N-termini is indicative of conserved tertiary and/or quaternary structure, and suggests that these molecules may interact with a common extracellular molecule. Likewise the strong amino acid conservation within the intracellular C-termini suggests that the proteins in this family may interact with a common molecule inside of the cell. A distinct physiological role for APP has yet to be determined. Clues to the function of any of the members of the APP-like family of proteins should help to elucidate the normal function and processing and regulation of APP.

Example 2

Mapping the Human Chromosomal Locus Encoding APLP1

Portions of the mouse brain cDNA and a 1.8 kb partial cDNA isolated from a human brain cDNA library were used to map the human chromosomal locus encoding APLP1. To determine the best restriction digest for the selective identification of the human chromosomal APLP1 fragments, human, mouse and hamster genomic DNAs were analyzed by Southern blot hybridization using the partial human cDNA clone following digestion with EcoRI, HindIII, PstI, and TaqI. EcoRI was chosen for further analysis since it produced human DNA fragments (approximately 8 kb and 3.3 kb, data not shown) that were clearly discernable from the rodent. A panel of DNAs from 31 human-rodent somatic cell lines (Geissler et al., *Somat. Cell Mol. Genet.* 17:197–214 (1991)) of known karyotype was digested with EcoRI. These DNAs were then probed with the human APLP1 cDNA clone and the hybridization pattern was consistent with the assignment of the APLP1 locus to chromosome 19.

To determine the regional position of APLP1 locus on chromosome 19, the full-length mouse brain APLP1 cDNA was hybridized to EcoRI-digested genomic DNA from a number of somatic cell hybrids containing only human chromosome 19or specific fragments of this autosome as well as other chromosomes (G35CCB, G35F3B, GM89A99c7B, G24B2AM, FON1A4, TVB1D, 1016A and 5HL94; FIG. 8). All of these hybrid lines, with the exception of GM89A99c7B, contain the two human specific APLP1 bands. GM89A99c7B contains the reciprocal part of the X:19 translocation occurring in 908K1, G35F3 and G35FCC (FIG. 8). These results exclude the APLP1 locus from the short arm of chromosome 19 and place it between 19q13.2 and the centromere.

Discussion

While no physiological role has been determined for APLP1, its map location is interesting in view of its potential relationship to Alzheimer's disease (AD). The chief component of Alzheimer-associated amyloid is the 39–43 amino acid βA4 peptide which is derived from the larger amyloid precursor protein (APP) encoded by a gene on chromosome 21 (Kang et al., *Nature* 325:733–736 (1987); Robakis et al., *Proc. Natl. Acad. Sci. USA* 84:4190–4194 (1987); Tanzi et al., *Science* 235:880–884 (1987). The gene defect for an early-onset (>65 years of age) form of familial Alzheimer's disease (FAD) has been mapped to chromosome 21 (St. George-Hyslop et al., *Science* 235:885–889 (1987)) and a small percentage (<3%) of FAD appears to be caused by mutations within the APP gene (Chartier-Harlin et al., *Nature* 353:884–846 (1991); Goate et al., *Nature* 349:704–706 (1991); Murrell et al., *Science* 254:97–99 (1991)). Genetic heterogeneity has also been reported for FAD (St. George-Hyslop et al., *Nature* 347:19 4–197 (1990)) and a set of late-onset (>65 years of age) FAD pedigrees have recently demonstrated linkage to chromosome 19 (Pericak-Vance et al., *Am. J. Hum. Genet. 48:1034–1050* (1991)). Because of the regional chromosomal localization of APLP1 to the proximal portion of 19q and the significant homology of this gene to APP, APLP1 is a candidate for the gene defect responsible for a late-onset form of FAD.

Example 3

Isolation and characterization of the Human APLP2 Gene encoding a homologue of the Alzheimer's Associated Amyloid B protein precursor In an attempt to isolate other members of the APP protein family, the mouse APLP1 sequence was first used to scan the Genbank database for homologous sequences. In addition to obtaining matches for APP, APPL, and the partial cDNA from rate testes, a match with an anonymous 274 base pair human brain cDNA entry (Genbank accession number M78104), was noted. This match, which was significant but not identical to mouse APLP1 (63% identity), indicated that M78104 was a small piece of a cDNA encoding a second APLP. In order to characterize the APP-like gene family in more detail, full length cDNAs for this second APLP, APLP2, were isolated. The isolation and characterization of APLP2 cDNA clones from human brain, provide further support for the hypothesis that APP is a member of a highly conserved gene family.

A human brain frontal cortex Lambda Zap II cDNA library (Stratagene) was screened with a probe consisting of a PCR product generated with primers designed to amplify a portion of the 274 base pair partial cDNA sequence identified in Genbank. To prepare the probe, a primer set (5'GCAACCGAATGGACAGGGTA 3' (SEQ ID NO:16) and 5°CAAGGCAGCCA GGTAGTTCTC 3' (SEQ ID NO:17) see FIGS. 9A–9B) was used to amplify a 232 base pair product from a human occipital cortex cDNA library. The PCR product was sequenced to confirm its identity and an internal primer set (5'GTAAAGAAGGAATGGG-AAGAGGC3' (SEQ ID NO:18); and 5'CCATCCGACGGC GGTCATTCAGC3'(SEQ ID NO:19); see FIGS. 9A–9B) was designed and used to amplify a 185 base pair PCR fragment (SG190) that was used for the human brain library screen. Screening, purification and sequencing of the SG190-positive clones, including a full length cDNA were carried out according to standard conditions (Wasco et al., *Proc.Natl.Acad.Sci. USA* 89:10758–10762 (1992)).

Human APLP2 is encoded by a 706 amino acid sequence (SEQ ID NO:4) that is similar to APP and APLP1 in overall structure as well as amino acid sequence. APLP2 is 52% identical, 69% similar to APP695 (FIGS. 9A–9B) and 43% identical, 63% similar to APLP1. Virtually all of the identified domains and motifs that characterize APP, APPL and APLP1 are present in APLP2. Specifically, an N-terminal cysteine-rich region (consisting of 12 cysteines), a novel zinc-binding motif (Bush et al., *Neurobiol. Aging* 13 (supplement 1):A.331 (1992)), an acidic-rich domain, N-glycosylation sites, a hydrophobic membrane spanning domain and a cytoplasmic domain containing a clathrin binding motif and potential serine/threonine, casine kinase I, II and tyrosine phosphorylation sites are conserved in APLP2 (FIGS. 9A–9B). FIGS. 10A–10B shows the amino acids that are identical or conservatively substituted in APLP2, APP and APLP1 demonstrating the extremely high degree of conservation among these proteins. Some of these stretches of homologous amino acids shown in FIGS. 10A–10B may contain potential consensus motifs that are germane to the function of this protein family.

Chromosomal Location of APLP2 Gene

To determine the chromosomal location of the APLP2 gene, a cDNA probe was hybridized to a filter containing Hind III-digested DNA from a panel of 43 human-rodent somatic cell hybrid lines containing either individual or specific sets of human chromosomes (Pelletier et al., *Genomics* 10:1079–1082 (1991); Geissler et al., *Som Cell Gen* 17:207–214 (1991)). The probe detected specific human APLP2 bands in somatic cell hybrid lines consistent with the assignment of the APLP2 gene locus to human chromosome 11. Specifically, a positive signal for human APLP2 was obtained in a somatic cell hybrid line containing DNA from chromosome 11 as its only human material, and in a hybrid containing chromosome 11 and three other human chromosomes.

During the sequencing of the human APLP2 cDNA clones, a single alternatively spliced form containing an exon encoding a 12 amino acid stretch was identified indicating that like APP, APLP2 is alternatively transcribed (FIGS. 9A–9B). Although a portion of the APLP2 cDNA isolated from mouse embryo contained a KPI domain similar to that in APP, a form of adult human APLP2 that contains such a domain has not yet been detected.

Northern Blot Analysis

Northern blot analysis of fetal peripheral tissue and adult brain regions demonstrated that the APLP2 message is approximately 4 kb in size (FIG. 11A–11B). Lighter bands at approximately 3 kb and 2 kb may represent cross-hybridizing messages from other members of the APP/APLP family, or as of yet unisolated APLP2 alternative transcripts. The APLP2 transcript was detected at varying levels in all peripheral and central nervous system tissues tested and displayed a level and pattern of expression that is extremely similar to that of APP (FIG. 11A). Both transcripts are expressed in relatively abundant amounts in brain, heart, and kidney and at lower levels in liver and thymus. However, in contrast to APP, APLP2 is expressed at relatively high levels in the small intestine and lung.

To determine the distribution of APLP2 transcript in the adult human brain Northern blot analysis was carried out on mRNA from 11 different brain regions (FIG. 11B). This same blot had been previously hybridized to APP thus allowing a direct comparison of expression of the two genes (Tanzi et al., *Science* 235:880–884 (1987); Tanzi et al., *Nature* 331:528–530(1988)). The levels of APLP2 mRNA were highest in the temporal association cortex (A20, Tanzi et al., *Nature* 331:528–530(1988)), the posterior perisylvian cortex-supramarginal gyri (A40), the anterior perisylvian cortex-opercular gyri (A44) and frontal pole of the cortex (A10). These regions which are particularly affected in the brains of AD patients, normally contain a relatively large amount of APP RNA. Moderate hybridization was detected in the cerebellar cortex and the caudate-putamen. Relatively weaker hybridization was seen in the striate, extrastriate, and motor cortices (A17, A18 and A4), the hippocampus, and the thalamus. Overall, APLP2 reveals a pattern of expression that is very similar to that of APP (FIG. 11B; Tanzi et al., *Science* 235:880–884 (1987); Tanzi et al., *Nature* 331:528–530(1988)), although, some differences were noted. For example, APLP2 is expressed at relatively higher levels than APP in thalamus, while APP expression is greater than that of APLP2 in Brodman area A40.

FIG. 12 shows the result of Northern blot hybridization of APLP2 and APP cDNA probes to RNA derived from normal and fetal brains with Down syndrome (DS), and from normal and adult brains with AD. Although APP expression is higher in the DS samples, APLP2 expression is not significantly changed. This result is not unexpected given the extra copy of chromosome 21 present in DS patients. APP expression is slightly lower in AD versus normal adult cerebellum, and is dramatically decreased in AD frontal cortex relative to normal (FIG. 12). This decrease in APP expression is probably a reflection of AD-related neuronal loss in these areas which is particularly enhanced in the frontal cortex. Surprisingly, it has presently been found that although APP expression is somewhat decreased in AD cerebellum compound to normal, APLP2 expression is clearly increased in this same AD cerebellum sample (FIG. 12). One possibility is that this may reflect a compensatory increase in APLP2 expression in response to lower levels of APP. It is equally conceivable that increased expression of APLP2 preceded the decrease in APP message.

The present inventors have discovered that APLPs may compete with APP for factors involved with maturation and processing (Wasco et al., *Proc. Natl. Acad. Sci. USA* 89:10758–10762 (1992)). This would require that the two proteins are produced and processed within the same cell populations. To address this issue, non isotopic in situ hybridization studies designed to localize APLP2 mRNA transcripts within the hippocampal formation, a region that is severely affected in AD, have been employed. It was found that the mRNA for APLP2 is contained in both the cell soma and, to some extent, neuronal processes of pyramidal neurons in the hippocampal formation (FIGS. 13A–13B). Much less hybridization was observed in smaller interneurons, glial cells, and endothelial cells. The subcellular localization is similar to that seen for APP and APLP1 messages using the same in situ hybridization procedure (Tanzi et al., *Mol. Brain Res.*:in press; Hyman et al., *Mol. Brain Res.*:in press; Wasco et al., *Alzheimer's disease and related disorders* 1992: selected communications (in press)). Moreover, the cellular specificity and regional distribution of the APLP messages are also extremely similar to those of APP indicating that the APP and APLPs are located within the same sets of neurons in the hippocampal formation.

Based on the overall conservation of amino acid sequence and domain structure within the APP gene family, these proteins may share common functions and, perhaps be processed similarly (Wasco et al., *Proc. Natl. Acad. Sci. USA* 89:10758–10762 (1992)). Recent data further indicate that APLP2 and APP undergo similar processing (unpublished data). Antibodies to APP, APLP1 and APPL recognize proteins in the Golgi (Wasco et al., *Proc. Natl. Acad. Sci. USA* 89:10758–10762 (1992); Zimmermann et al., *EMBO J.* 7:367–372 (1988); Palacios et al., *Mol. Brain Res.* 15:195–206 (1992); Luo et al., *J. Neurosci.* 10:3849–3861 (1990)). Likewise, APLP2 appears to be associated with the Golgi apparatus unpublished data. This suggests that maturation of these proteins in the Golgi very likely involves interaction with common factors. The apparent similarities in the processing and maturation of APP and APLP2 raises the possibility that altered expression of APLP2 or other APLPs could affect the post-translational modification and metabolism of APP in cells where these genes are co-expressed. If APLP2 or other APLPs were to interfere with the proper maturation (e.g. N- or O-glycosylation) of APP, APP could be rerouted into alternative pathways including those predisposed to amyloid formation. Along these same lines, if the metabolic machinery responsible for processing APP were overburdened with members of the APLP family, altered metabolism of APP may occur, perhaps resulting in increased production of amyloidogenic fragments. Therefore, although the APLP2 and APLP1 do not contain an Aβ domain, they may still ultimately affect the maturation and/or metabolism of APP.

All publications mentioned in this specification are indicative of the level of skill of those skilled in the art to which this invention pertains. All publications are herein incorporated by reference, to the same extent as if each individual publication was specifically and individually indicated to be incorporated by reference.

While the invention has been described in connection with the specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 9 amino acids
( B ) TYPE: amino acid
( C ) STRANDEDNESS: both
( D ) TOPOLOGY: linear ( i i ) MOLECULE TYPE: peptide ( x i ) SEQUENCE DESCRIPTION: SEQ ID NO:1:

```
Gln Gln Leu Arg Glu Leu Gln Arg His
1               5               9
```

( 2 ) INFORMATION FOR SEQ ID NO:2:

( i ) SEQUENCE CHARACTERISTICS:
( A ) LENGTH: 2358 base pairs
( B ) TYPE: nucleic acid
( C ) STRANDEDNESS: both
( D ) TOPOLOGY: linear ( i i ) MOLECULE TYPE: DNA ( i x ) FEATURE:
( A ) NAME/KEY: CDS
( B ) LOCATION: 88..2046

( x i ) SEQUENCE DESCRIPTION: SEQ ID NO:2:

```
CGGCACGAGG TGGCGCTGGG AGCTCCTGTC ACCGCTGGGG CCGGGTAGGG GCGGGCGGGA      60

GCGCAGGGAC GTGAGGGCCG AGCGGAC ATG GGG CCC ACC AGC CCC GCC GCT         111
                              Met Gly Pro Thr Ser Pro Ala Ala
                               1               5

CGC GGT CAG GGT CGC CGC TGG CGA CCG CCG CTG CCG CTG TTG CTG CCA       159
Arg Gly Gln Gly Arg Arg Trp Arg Pro Pro Leu Pro Leu Leu Leu Pro
    10                  15                  20

CTG TCA TTG CTG CTT CTG CGC GCG CAG CTC GCC GTC GGG AAC CTG GCT       207
Leu Ser Leu Leu Leu Leu Arg Ala Gln Leu Ala Val Gly Asn Leu Ala
 25                  30                  35                  40

GTT GGG AGC CCC AGC GCG GCC GAG GCT CCG GGG TCG GCT CAA GTG GCT       255
Val Gly Ser Pro Ser Ala Ala Glu Ala Pro Gly Ser Ala Gln Val Ala
                45                  50                  55

GGA CTA TGT GGG CGT CTA ACC CTT CAC CGG GAC TTG CGC ACC GGC CGC       303
Gly Leu Cys Gly Arg Leu Thr Leu His Arg Asp Leu Arg Thr Gly Arg
            60                  65                  70

TGG GAA CCA GAC CCA CAG CGA TCA CGA CGC TGT CTT CTG GAC CCG CAG       351
Trp Glu Pro Asp Pro Gln Arg Ser Arg Arg Cys Leu Leu Asp Pro Gln
        75                  80                  85

CGC GTG CTG GAG TAC TGC AGA CAG ATG TAC CCC GAG CTG CAC ATA GCA       399
Arg Val Leu Glu Tyr Cys Arg Gln Met Tyr Pro Glu Leu His Ile Ala
    90                  95                 100

CGC GTG GAG CAG GCT GCA CAG GCC ATC CCG ATG GAG CGC TGG TGT GGG       447
Arg Val Glu Gln Ala Ala Gln Ala Ile Pro Met Glu Arg Trp Cys Gly
105                 110                 115                 120

GGT ACC CGG AGT GGC AGA TGC GCC CAC CCC CAC CAT GAG GTT GTG CCC       495
Gly Thr Arg Ser Gly Arg Cys Ala His Pro His His Glu Val Val Pro
                125                 130                 135
```

-continued

```
TTC CAT TGC CTG CCT GGC GAA TTC GTG AGT GAA GCC CTG CTA GTG CCC     543
Phe His Cys Leu Pro Gly Glu Phe Val Ser Glu Ala Leu Leu Val Pro
            140                 145                 150

GAA GGC TGT CGG TTC TTG CAC CAG GAG CGT ATG GAC CAG TGT GAG AGT     591
Glu Gly Cys Arg Phe Leu His Gln Glu Arg Met Asp Gln Cys Glu Ser
        155                 160                 165

TCA ACC AGG AGG CAT CAG GAG GCT CAG GAG GCC TGC AGC TCT CAG GGC     639
Ser Thr Arg Arg His Gln Glu Ala Gln Glu Ala Cys Ser Ser Gln Gly
    170                 175                 180

CTC ATC CTG CAC GGC TCT GGC ATG CTT TTG CCC TGT GGC TCT GAT CGG     687
Leu Ile Leu His Gly Ser Gly Met Leu Leu Pro Cys Gly Ser Asp Arg
185                 190                 195                 200

TTC CGA GGT GTG GAG TAT GTA TGC TGT CCA CCT CCC GCA ACT CCC AAC     735
Phe Arg Gly Val Glu Tyr Val Cys Cys Pro Pro Pro Ala Thr Pro Asn
                205                 210                 215

CCA TCT GGG ATG GCA GCT GGT GAC CCC TCT ACC CGG TCC TGG CCC CTG     783
Pro Ser Gly Met Ala Ala Gly Asp Pro Ser Thr Arg Ser Trp Pro Leu
            220                 225                 230

GGG GGC AGA GCA GAG GGA GGT GAG GAT GAA GAG GAG GTG GAA TCT TTC     831
Gly Gly Arg Ala Glu Gly Gly Glu Asp Glu Glu Glu Val Glu Ser Phe
        235                 240                 245

CCT CAG CCA GTA GAC GAT TAC TTC GTA GAG CCC CCT CAG GCT GAA GAA     879
Pro Gln Pro Val Asp Asp Tyr Phe Val Glu Pro Pro Gln Ala Glu Glu
    250                 255                 260

GAA GAG GAA GAG GAG GAA GAA AGG GCC CCA CCT CCC AGC TCC CAC ACC     927
Glu Glu Glu Glu Glu Glu Glu Arg Ala Pro Pro Pro Ser Ser His Thr
265                 270                 275                 280

CCT GTC ATG GTT AGC AGA GTC ACT CCC ACC CCA AGG CCT ACT GAT GGT     975
Pro Val Met Val Ser Arg Val Thr Pro Thr Pro Arg Pro Thr Asp Gly
                285                 290                 295

GTG GAT GTT TAC TTT GGC ATG CCT GGG GAA ATC GGC GAG CAT GAG GGT    1023
Val Asp Val Tyr Phe Gly Met Pro Gly Glu Ile Gly Glu His Glu Gly
            300                 305                 310

TTC CTG AGG GCC AAG ATG GAC CTG GAG GAG CGT AGG ATG CGC CAG ATT    1071
Phe Leu Arg Ala Lys Met Asp Leu Glu Glu Arg Arg Met Arg Gln Ile
        315                 320                 325

AAT GAG GTG ATG CGT GAA TGG GCC ATG GCT GAC AGC CAA TCT AAG AAC    1119
Asn Glu Val Met Arg Glu Trp Ala Met Ala Asp Ser Gln Ser Lys Asn
    330                 335                 340

CTG CCA AAG GCG GAC AGG CAG GCC CTG AAT GAG CAC TTC CAG TCC ATT    1167
Leu Pro Lys Ala Asp Arg Gln Ala Leu Asn Glu His Phe Gln Ser Ile
345                 350                 355                 360

CTG CAG ACC CTG GAA GAA CAA GTG TCT GGT GAA CGG CAA CGC CTG GTG    1215
Leu Gln Thr Leu Glu Glu Gln Val Ser Gly Glu Arg Gln Arg Leu Val
                365                 370                 375

GAG ACC CAC GCC ACC AGA GTC ATC GCT CTG ATC AAC GAC CAG CGC CGA    1263
Glu Thr His Ala Thr Arg Val Ile Ala Leu Ile Asn Asp Gln Arg Arg
            380                 385                 390

GCA GCC CTG GAA GGT TTC CTG GCA GCC TTA CAG GGC GAT CCG CCT CAG    1311
Ala Ala Leu Glu Gly Phe Leu Ala Ala Leu Gln Gly Asp Pro Pro Gln
        395                 400                 405

GCT GAG CGA GTT CTG ATG GCC CTG AGG CGC TAC CTG CGC GCC GAG CAG    1359
Ala Glu Arg Val Leu Met Ala Leu Arg Arg Tyr Leu Arg Ala Glu Gln
    410                 415                 420

AAA GAG CAG AGG CAC ACT CTG AGG CAC TAC CAG CAC GTG GCC GCA GTG    1407
Lys Glu Gln Arg His Thr Leu Arg His Tyr Gln His Val Ala Ala Val
425                 430                 435                 440

GAT CCT GAG AAG GCC CAG CAG ATG CGC TTT CAG GTC CAG ACC CAC CTT    1455
Asp Pro Glu Lys Ala Gln Gln Met Arg Phe Gln Val Gln Thr His Leu
                445                 450                 455
```

-continued

```
CAG GTG ATC GAA GAG CGA ATG AAT CAG AGC CTG GGG CTG CTC GAC CAG    1503
Gln Val Ile Glu Glu Arg Met Asn Gln Ser Leu Gly Leu Leu Asp Gln
            460                 465                 470

AAC CCT CAC CTG GCT CAG GAG CTG CGG CCA CAG ATC CAG GAG CTT CTC    1551
Asn Pro His Leu Ala Gln Glu Leu Arg Pro Gln Ile Gln Glu Leu Leu
        475                 480                 485

CTT GCT GAA CAC TTG GGT CCC AGT GAA CTG GAC GCC TCT GTG CCC GGG    1599
Leu Ala Glu His Leu Gly Pro Ser Glu Leu Asp Ala Ser Val Pro Gly
    490                 495                 500

AGC AGC AGT GAG GAC AAA GGT AGC CTC CAG CCT CCC GAA TCC AAG GAC    1647
Ser Ser Ser Glu Asp Lys Gly Ser Leu Gln Pro Pro Glu Ser Lys Asp
505                 510                 515                 520

GAT CCC CCA GTG ACC CTT CCA AAA GGG TCC ACA GAT CAA GAG TCA TCC    1695
Asp Pro Pro Val Thr Leu Pro Lys Gly Ser Thr Asp Gln Glu Ser Ser
                525                 530                 535

TCC TCT GGG AGA GAG AAG CTA ACT CCA CTG GAG CAG TAT GAG CAA AAG    1743
Ser Ser Gly Arg Glu Lys Leu Thr Pro Leu Glu Gln Tyr Glu Gln Lys
            540                 545                 550

GTG AAT GCA TCC GCC CCG AGG GGG TTT CCG TTC CAC TCG TCA GAT ATC    1791
Val Asn Ala Ser Ala Pro Arg Gly Phe Pro Phe His Ser Ser Asp Ile
        555                 560                 565

CAG CGG GAT GAA CTG GCT CCT TCC GGG ACT GGA GTG TCC CGA GAG GCC    1839
Gln Arg Asp Glu Leu Ala Pro Ser Gly Thr Gly Val Ser Arg Glu Ala
    570                 575                 580

TTG TCA GGT CTG CTG ATC ATG GGA GCT GGA GGA GGC TCT CTC ATT GTC    1887
Leu Ser Gly Leu Leu Ile Met Gly Ala Gly Gly Gly Ser Leu Ile Val
585                 590                 595                 600

CTA TCC TTG CTG CTT CTG CGC AAG AAG AAA CCC TAT GGG ACT ATC AGC    1935
Leu Ser Leu Leu Leu Leu Arg Lys Lys Lys Pro Tyr Gly Thr Ile Ser
                605                 610                 615

CAT GGA GTG GTG GAG GTG GAC CCC ATG CTG ACC CTG GAG GAG CAG CAG    1983
His Gly Val Val Glu Val Asp Pro Met Leu Thr Leu Glu Glu Gln Gln
            620                 625                 630

CTC CGG GAA CTT CAG AGG CAT GGC TAT GAG AAC CCC ACC TAC CGC TTC    2031
Leu Arg Glu Leu Gln Arg His Gly Tyr Glu Asn Pro Thr Tyr Arg Phe
        635                 640                 645

CTG GAA GAA CGA CCT TGACCCCTAC CCTAGCTGCC TTCAGCTGAG CCCTACTGCC    2086
Leu Glu Glu Arg Pro
    650

TTCTTCCGGC CCCCCAAACC CAACTCCCAG CTTCCGGTGG GGGAGGGAGA TCTTGACAAA    2146

TTCATTCTTG TTTCCCCTTC CTAGTTCCAA ATTCCACACC CTTAGAAATC CCCAGCTCCT    2206

GTCCCACAAG GGACCTCTTC ACCTTAATTT ATTTTACGTT AATTTATTGC TCCTTAAGGT    2266

GACCTGGGTC CCAGGTATGT ATGTCACTCC CTGGAATTCA CCATCCCACG TTTCTTCACT    2326

AACATCCCAA TAAACTCCTC TTTCCCTCCG GC                                2358
```

( 2 ) INFORMATION FOR SEQ ID NO:3:

( i ) SEQUENCE CHARACTERISTICS:
( A ) LENGTH: 653 amino acids
( B ) TYPE: amino acid
( D ) TOPOLOGY: linear ( i i ) MOLECULE TYPE: protein ( x i ) SEQUENCE DESCRIPTION: SEQ ID NO:3:

```
Met Gly Pro Thr Ser Pro Ala Ala Arg Gly Gln Gly Arg Arg Trp Arg
 1               5                  10                  15

Pro Pro Leu Pro Leu Leu Leu Pro Leu Ser Leu Leu Leu Leu Arg Ala
            20                  25                  30
```

-continued

Gln Leu Ala Val Gly Asn Leu Ala Val Gly Ser Pro Ser Ala Ala Glu
35 40 45

Ala Pro Gly Ser Ala Gln Val Ala Gly Leu Cys Gly Arg Leu Thr Leu
50 55 60

His Arg Asp Leu Arg Thr Gly Arg Trp Glu Pro Asp Pro Gln Arg Ser
65 70 75 80

Arg Arg Cys Leu Leu Asp Pro Gln Arg Val Leu Glu Tyr Cys Arg Gln
85 90 95

Met Tyr Pro Glu Leu His Ile Ala Arg Val Glu Gln Ala Ala Gln Ala
100 105 110

Ile Pro Met Glu Arg Trp Cys Gly Gly Thr Arg Ser Gly Arg Cys Ala
115 120 125

His Pro His His Glu Val Val Pro Phe His Cys Leu Pro Gly Glu Phe
130 135 140

Val Ser Glu Ala Leu Leu Val Pro Glu Gly Cys Arg Phe Leu His Gln
145 150 155 160

Glu Arg Met Asp Gln Cys Glu Ser Ser Thr Arg Arg His Gln Glu Ala
165 170 175

Gln Glu Ala Cys Ser Ser Gln Gly Leu Ile Leu His Gly Ser Gly Met
180 185 190

Leu Leu Pro Cys Gly Ser Asp Arg Phe Arg Gly Val Glu Tyr Val Cys
195 200 205

Cys Pro Pro Pro Ala Thr Pro Asn Pro Ser Gly Met Ala Ala Gly Asp
210 215 220

Pro Ser Thr Arg Ser Trp Pro Leu Gly Gly Arg Ala Glu Gly Gly Glu
225 230 235 240

Asp Glu Glu Glu Val Glu Ser Phe Pro Gln Pro Val Asp Asp Tyr Phe
245 250 255

Val Glu Pro Pro Gln Ala Glu Glu Glu Glu Glu Glu Glu Glu Glu Arg
260 265 270

Ala Pro Pro Pro Ser Ser His Thr Pro Val Met Val Ser Arg Val Thr
275 280 285

Pro Thr Pro Arg Pro Thr Asp Gly Val Asp Val Tyr Phe Gly Met Pro
290 295 300

Gly Glu Ile Gly Glu His Glu Gly Phe Leu Arg Ala Lys Met Asp Leu
305 310 315 320

Glu Glu Arg Arg Met Arg Gln Ile Asn Glu Val Met Arg Glu Trp Ala
325 330 335

Met Ala Asp Ser Gln Ser Lys Asn Leu Pro Lys Ala Asp Arg Gln Ala
340 345 350

Leu Asn Glu His Phe Gln Ser Ile Leu Gln Thr Leu Glu Glu Gln Val
355 360 365

Ser Gly Glu Arg Gln Arg Leu Val Glu Thr His Ala Thr Arg Val Ile
370 375 380

Ala Leu Ile Asn Asp Gln Arg Arg Ala Ala Leu Glu Gly Phe Leu Ala
385 390 395 400

Ala Leu Gln Gly Asp Pro Pro Gln Ala Glu Arg Val Leu Met Ala Leu
405 410 415

Arg Arg Tyr Leu Arg Ala Glu Gln Lys Glu Gln Arg His Thr Leu Arg
420 425 430

His Tyr Gln His Val Ala Ala Val Asp Pro Glu Lys Ala Gln Gln Met
435 440 445

Arg Phe Gln Val Gln Thr His Leu Gln Val Ile Glu Glu Arg Met Asn
450 455 460

Gln Ser Leu Gly Leu Leu Asp Gln Asn Pro His Leu Ala Gln Glu Leu
465 470 475 480

Arg Pro Gln Ile Gln Glu Leu Leu Leu Ala Glu His Leu Gly Pro Ser
485 490 495

Glu Leu Asp Ala Ser Val Pro Gly Ser Ser Ser Glu Asp Lys Gly Ser
500 505 510

Leu Gln Pro Pro Glu Ser Lys Asp Asp Pro Pro Val Thr Leu Pro Lys
515 520 525

Gly Ser Thr Asp Gln Glu Ser Ser Ser Ser Gly Arg Glu Lys Leu Thr
530 535 540

Pro Leu Glu Gln Tyr Glu Gln Lys Val Asn Ala Ser Ala Pro Arg Gly
545 550 555 560

Phe Pro Phe His Ser Ser Asp Ile Gln Arg Asp Glu Leu Ala Pro Ser
565 570 575

Gly Thr Gly Val Ser Arg Glu Ala Leu Ser Gly Leu Leu Ile Met Gly
580 585 590

Ala Gly Gly Gly Ser Leu Ile Val Leu Ser Leu Leu Leu Leu Arg Lys
595 600 605

Lys Lys Pro Tyr Gly Thr Ile Ser His Gly Val Val Glu Val Asp Pro
610 615 620

Met Leu Thr Leu Glu Glu Gln Gln Leu Arg Glu Leu Gln Arg His Gly
625 630 635 640

Tyr Glu Asn Pro Thr Tyr Arg Phe Leu Glu Glu Arg Pro
645 650

( 2 ) INFORMATION FOR SEQ ID NO:4:

( i ) SEQUENCE CHARACTERISTICS:
( A ) LENGTH: 706 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Ala Ala Thr Gly Thr Ala Ala Arg Ala Ala Thr Gly Arg Leu Leu
1 5 10 15

Leu Leu Leu Leu Val Gly Leu Thr Ala Pro Ala Ala Ala Leu Ala Gly
20 25 30

Tyr Ile Glu Ala Leu Ala Ala Ala Ala Gly Thr Gly Phe Ala Val Ala
35 40 45

Glu Pro Gln Ile Ala Met Phe Cys Gly Lys Leu Asn Met His Val Asn
50 55 60

Ile Gln Thr Gly Lys Trp Glu Pro Asp Pro Thr Gly Thr Lys Ser Cys
65 70 75 80

Phe Arg Thr Lys Glu Glu Val Leu Gln Tyr Cys Gln Glu Met Tyr Pro
85 90 95

Glu Leu Gln Ile Thr Asn Val Met Glu Ala Asn Gln Arg Val Ser Ile
100 105 110

Asp Asn Trp Cys Arg Arg Asp Lys Lys Gln Cys Lys Ser Arg Phe Val
115 120 125

Thr Pro Phe Lys Cys Leu Val Gly Glu Phe Val Ser Asp Val Leu Leu
130 135 140

Val Pro Glu Lys Cys Arg Phe Phe His Lys Glu Arg Met Glu Val Cys
145 150 155 160

-continued

Glu Asn His Gln His Trp His Thr Val Val Lys Glu Ala Cys Leu Thr
165 170 175

Gln Gly Met Thr Leu Tyr Ser Tyr Gly Met Leu Leu Pro Cys Gly Val
180 185 190

Asp Gln Phe His Gly Thr Glu Tyr Val Cys Cys Pro Gln Thr Lys Asp
195 200 205

Tyr Trp Ser Val Ser Lys Glu Glu Glu Glu Glu Glu Asp Glu Glu Glu
210 215 220

Glu Glu Glu Glu Asp Glu Glu Glu Asp Tyr Asp Val Tyr Lys Ser Glu
225 230 235 240

Phe Pro Thr Glu Ala Asp Leu Glu Asp Phe Thr Glu Ala Ala Val Asp
245 250 255

Glu Asp Asp Glu Asp Glu Glu Glu Gly Glu Glu Val Val Glu Asp Arg
260 265 270

Asp Tyr Tyr Tyr Asp Thr Phe Lys Gly Asp Asp Tyr Asn Glu Glu Asn
275 280 285

Pro Thr Glu Pro Gly Ser Asp Gly Thr Met Ser Asp Lys Glu Ile Thr
290 295 300

His Asp Val Lys Val Pro Pro Thr Pro Leu Pro Thr Asn Asp Val Asp
305 310 315 320

Val Tyr Phe Glu Thr Ser Ala Asp Asp Asn Glu His Ala Arg Phe Gln
325 330 335

Lys Ala Glu Lys Glu Gln Leu Ile Glu Arg His Arg Asn Arg Met Asp
340 345 350

Arg Val Lys Lys Glu Trp Glu Glu Ala Glu Leu Gln Ala Lys Asn Leu
355 360 365

Pro Lys Ala Glu Arg Gln Thr Leu Ile Gln His Phe Gln Ala Met Val
370 375 380

Lys Ala Leu Glu Lys Ala Glu Ala Ala Ser Glu Lys Gln Gln Leu Val
385 390 395 400

Glu Thr His Leu Ala Arg Val Glu Ala Met Leu Asn Asp Arg Arg Met
405 410 415

Ala Leu Glu Asn Tyr Leu Ala Ala Leu Gln Arg Ser Asp Pro Pro Arg
420 425 430

Pro His Arg Ile Leu Gln Pro Leu Arg Arg Tyr Val Arg Ala Glu Asn
435 440 445

Lys Asp Arg Leu His Thr Ile Arg His Tyr Gln His Val Leu Ala Val
450 455 460

Asp Pro Glu Lys Ala Ala Gln Met Lys Ser Gln Val Met Thr His Leu
465 470 475 480

His Val Ile Glu Glu Arg Arg Asn Gln Ser Leu Ser Leu Leu Tyr Lys
485 490 495

Asp Pro Tyr Val Ala Arg Ile Gln Glu Asn Asp Glu Leu Leu Gln Ala
500 505 510

Glu Arg Ala Asp Met Asp Gln Phe Thr Ala Ser Ile Ser Glu Thr Pro
515 520 525

Val Asp Val Arg Val Ser Ser Glu Glu Ser Glu Glu Ile Pro Pro Phe
530 535 540

His Pro Phe His Pro Phe Pro Ala Leu Pro Glu Asn Glu Asp Thr Gln
545 550 555 560

Pro Glu Leu Tyr His Pro Met Lys Lys Gly Ser Gly Val Gly Glu Gln
565 570 575

Asp Gly Gly Leu Ile Gly Ala Glu Glu Lys Val Ile Asn Ser Lys Asn
580 585 590

Lys Val Asp Glu Asn Met Val Ile Asp Glu Thr Leu Asp Lys Glu Met
595 600 605

Ile Phe Asn Ala Glu Arg Val Gly Gly Leu Glu Glu Arg Glu Ser Val
610 615 620

Gly Pro Leu Arg Glu Asp Phe Ser Leu Ser Ser Ser Ala Ser Ile Gly
625 630 635 640

Leu Leu Val Ile Ala Val Ala Ile Ala Thr Val Ile Val Ile Ser Leu
645 650 655

Val Met Leu Arg Lys Arg Gln Val Cys Thr Ile Ser His Gly Ile Val
660 665 670

Glu Val Asp Pro Met Leu Thr Pro Glu Glu Arg His Leu Asn Lys Met
675 680 685

Gln Asn His Gly Tyr Glu Asn Pro Thr Tyr Lys Thr Leu Glu Gln Met
690 695 700

Gln Ile
705

( 2 ) INFORMATION FOR SEQ ID NO:5:

( i ) SEQUENCE CHARACTERISTICS:
( A ) LENGTH: 694 amino acids
( B ) TYPE: amino acid
( D ) TOPOLOGY: linear ( i i ) MOLECULE TYPE: protein ( x i ) SEQUENCE DESCRIPTION: SEQ ID NO:5:

Met Leu Pro Gly Leu Ala Leu Leu Leu Leu Ala Ala Trp Thr Ala Arg
1 5 10 15

Ala Leu Glu Val Pro Thr Asp Gly Asn Ala Gly Leu Leu Ala Glu Pro
20 25 30

Gln Ile Ala Met Phe Cys Gly Arg Leu Asn Met His Met Asn Val Gln
35 40 45

Asn Gly Lys Trp Asp Ser Asp Pro Ser Gly Thr Lys Thr Cys Ile Asp
50 55 60

Thr Lys Glu Gly Ile Leu Gln Tyr Cys Gln Glu Val Tyr Pro Glu Leu
65 70 75 80

Gln Ile Thr Asn Val Val Glu Ala Asn Gln Pro Val Thr Ile Gln Asn
85 90 95

Trp Cys Lys Arg Gly Arg Lys Gln Cys Lys Thr His Pro His Phe Val
100 105 110

Ile Pro Tyr Arg Cys Leu Val Gly Glu Phe Val Ser Asp Ala Leu Leu
115 120 125

Val Pro Asp Lys Cys Lys Phe Leu His Gln Glu Arg Met Asp Val Cys
130 135 140

Glu Thr His Leu His Trp His Thr Val Ala Lys Glu Thr Cys Ser Glu
145 150 155 160

Lys Ser Thr Asn Leu His Asp Tyr Gly Met Leu Leu Pro Cys Gly Ile
165 170 175

Asp Lys Phe Arg Gly Val Glu Phe Val Cys Cys Pro Leu Ala Glu Glu
180 185 190

Ser Asp Asn Val Asp Ser Ala Asp Ala Glu Glu Asp Asp Ser Asp Val
195 200 205

Trp Trp Gly Gly Ala Asp Thr Asp Tyr Ala Asp Gly Ser Glu Asp Lys
210 215 220

-continued

```
Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655
```

His His Gly Val Val Glu Val Asp Ala Ala Val Thr Pro Glu Glu Arg
660 665 670

His Leu Ser Lys Met Gln Gln Asn Gly Tyr Glu Asn Pro Thr Tyr Lys
675 680 685

Phe Phe Glu Gln Met Gln
690

( 2 ) INFORMATION FOR SEQ ID NO:6:

( i ) SEQUENCE CHARACTERISTICS:
( A ) LENGTH: 190 amino acids
( B ) TYPE: amino acid
( D ) TOPOLOGY: linear ( i i ) MOLECULE TYPE: peptide ( x i ) SEQUENCE DESCRIPTION: SEQ ID NO:6:

Leu Leu Leu Pro Leu Ser Leu Leu Leu Leu Arg Ala Gln Leu Ala Val
1 5 10 15

Gly Asn Leu Ala Val Gly Ser Pro Ser Ala Ala Glu Ala Pro Gly Ser
20 25 30

Ala Gln Val Ala Gly Leu Cys Gly Arg Leu Thr Leu His Arg Asp Leu
35 40 45

Arg Thr Gly Arg Trp Glu Pro Asp Pro Gln Arg Ser Arg Arg Cys Leu
50 55 60

Leu Asp Pro Gln Arg Val Leu Glu Tyr Cys Arg Gln Met Tyr Pro Glu
65 70 75 80

Leu His Ile Ala Arg Val Glu Gln Ala Ala Gln Ala Ile Pro Met Glu
85 90 95

Arg Trp Cys Gly Gly Thr Arg Ser Gly Arg Cys Ala His Pro His His
100 105 110

Glu Val Val Pro Phe His Cys Leu Pro Gly Glu Phe Val Ser Glu Ala
115 120 125

Leu Leu Val Pro Glu Gly Cys Arg Phe Leu His Gln Glu Arg Met Asp
130 135 140

Gln Cys Glu Ser Ser Thr Arg Arg His Gln Glu Ala Gln Glu Ala Cys
145 150 155 160

Ser Ser Gln Gly Leu Ile Leu His Gly Ser Gly Met Leu Leu Pro Cys
165 170 175

Gly Ser Asp Arg Phe Arg Gly Val Glu Tyr Val Cys Cys Pro
180 185 190

( 2 ) INFORMATION FOR SEQ ID NO:7:

( i ) SEQUENCE CHARACTERISTICS:
( A ) LENGTH: 155 amino acids
( B ) TYPE: amino acid
( D ) TOPOLOGY: linear ( i i ) MOLECULE TYPE: peptide ( x i ) SEQUENCE DESCRIPTION: SEQ ID NO:7:

Ala Lys Met Asp Leu Glu Glu Arg Arg Met Arg Gln Ile Asn Glu Val
1 5 10 15

Met Arg Glu Trp Ala Met Ala Asp Ser Gln Ser Lys Asn Leu Pro Lys
20 25 30

Ala Asp Arg Gln Ala Leu Asn Glu His Phe Gln Ser Ile Leu Gln Thr
35 40 45

-continued

| | | | | | | | | | | | | | | | |
|---|---|---|---|---|---|---|---|---|---|---|---|---|---|---|---|
| Leu | Glu 50 | Glu | Gln | Val | Ser | Gly 55 | Glu | Arg | Gln | Arg | Leu 60 | Val | Glu | Thr | His |
| Ala 65 | Thr | Arg | Val | Ile | Ala 70 | Leu | Ile | Asn | Asp | Gln 75 | Arg | Arg | Ala | Ala | Leu 80 |
| Glu | Gly | Phe | Leu | Ala 85 | Ala | Leu | Gln | Gly | Asp 90 | Pro | Pro | Gln | Ala | Glu 95 | Arg |
| Val | Leu | Met | Ala 100 | Leu | Arg | Arg | Tyr | Leu 105 | Arg | Ala | Glu | Gln | Lys 110 | Glu | Gln |
| Arg | His | Thr 115 | Leu | Arg | His | Tyr | Gln 120 | His | Val | Ala | Ala | Val 125 | Asp | Pro | Glu |
| Lys | Ala 130 | Gln | Gln | Met | Arg | Phe 135 | Gln | Val | Gln | Thr | His 140 | Leu | Gln | Val | Ile |
| Glu 145 | Glu | Arg | Met | Asn | Gln 150 | Ser | Leu | Gly | Leu | Leu 155 | | | | | |

( 2 ) INFORMATION FOR SEQ ID NO:8:

( i ) SEQUENCE CHARACTERISTICS:
( A ) LENGTH: 46 amino acids
( B ) TYPE: amino acid
( D ) TOPOLOGY: linear ( i i ) MOLECULE TYPE: peptide ( x i ) SEQUENCE DESCRIPTION: SEQ ID NO:8:

| | | | | | | | | | | | | | | | |
|---|---|---|---|---|---|---|---|---|---|---|---|---|---|---|---|
| Lys 1 | Lys | Lys | Pro | Tyr 5 | Gly | Thr | Ile | Ser | His 10 | Gly | Val | Val | Glu | Val 15 | Asp |
| Pro | Met | Leu | Thr 20 | Leu | Glu | Glu | Gln | Gln 25 | Leu | Arg | Glu | Leu | Gln 30 | Arg | His |
| Gly | Tyr | Glu 35 | Asn | Pro | Thr | Tyr | Arg 40 | Phe | Leu | Glu | Glu | Arg 45 | Pro | | |

( 2 ) INFORMATION FOR SEQ ID NO:9:

( i ) SEQUENCE CHARACTERISTICS:
( A ) LENGTH: 188 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

| | | | | | | | | | | | | | | | |
|---|---|---|---|---|---|---|---|---|---|---|---|---|---|---|---|
| Met 1 | Leu | Pro | Gly | Leu 5 | Ala | Leu | Leu | Leu | Leu 10 | Ala | Ala | Trp | Thr | Ala 15 | Arg |
| Ala | Leu | Glu | Val 20 | Pro | Thr | Asp | Gly | Asn 25 | Ala | Gly | Leu | Leu | Ala 30 | Glu | Pro |
| Gln | Ile | Ala 35 | Met | Phe | Cys | Gly | Arg 40 | Leu | Asn | Met | His | Asn 45 | Met | Val | Gln |
| Asn | Gly 50 | Lys | Trp | Asp | Ser | Asp 55 | Pro | Ser | Gly | Thr | Lys 60 | Thr | Cys | Ile | Asp |
| Thr 65 | Lys | Glu | Gly | Ile | Leu 70 | Gln | Tyr | Cys | Gln | Glu 75 | Val | Tyr | Pro | Glu | Leu 80 |
| Gln | Ile | Thr | Asn | Val 85 | Val | Glu | Ala | Asn | Gln 90 | Pro | Val | Thr | Ile | Gln 95 | Asn |
| Trp | Cys | Lys | Arg 100 | Gly | Arg | Lys | Gln | Cys 105 | Lys | Thr | His | Pro | His 110 | Phe | Val |
| Ile | Pro | Tyr 115 | Arg | Cys | Leu | Val | Gly 120 | Glu | Phe | Val | Ser | Asp 125 | Ala | Leu | Leu |

Val Pro Asp Lys Cys Lys Phe Leu His Gln Glu Arg Met Asp Val Cys
130 135 140

Glu Thr His Leu His Trp His Thr Val Ala Lys Glu Thr Cys Ser Glu
145 150 155 160

Lys Ser Thr Asn Leu His Asp Tyr Gly Met Leu Leu Pro Cys Gly Ile
165 170 175

Asp Lys Phe Arg Gly Val Glu Phe Val Cys Cys Pro
180 185

( 2 ) INFORMATION FOR SEQ ID NO:10:

( i ) SEQUENCE CHARACTERISTICS:
( A ) LENGTH: 155 amino acids
( B ) TYPE: amino acid
( D ) TOPOLOGY: linear ( i i ) MOLECULE TYPE: peptide ( x i ) SEQUENCE DESCRIPTION: SEQ ID NO:10:

Ala Lys Glu Arg Leu Glu Ala Lys His Arg Glu Arg Met Ser Gln Val
1 5 10 15

Met Arg Glu Trp Glu Glu Ala Glu Arg Gln Ala Lys Asn Leu Pro Lys
20 25 30

Ala Asp Lys Lys Ala Val Ile Gln His Phe Gln Glu Lys Val Glu Ser
35 40 45

Leu Glu Gln Glu Ala Ala Asn Glu Arg Gln Gln Leu Val Glu Thr His
50 55 60

Met Ala Arg Val Glu Ala Met Leu Asn Asp Arg Arg Arg Leu Ala Leu
65 70 75 80

Glu Asn Tyr Ile Thr Ala Leu Gln Ala Val Pro Pro Arg Pro Arg His
85 90 95

Val Phe Asn Met Leu Lys Lys Tyr Val Arg Ala Glu Gln Lys Asp Arg
100 105 110

Gln His Thr Leu Lys His Phe Glu His Val Arg Met Val Asp Pro Lys
115 120 125

Lys Ala Ala Gln Ile Arg Ser Gln Val Met Thr His Leu Arg Val Ile
130 135 140

Tyr Glu Arg Met Asn Gln Ser Leu Ser Leu Leu
145 150 155

( 2 ) INFORMATION FOR SEQ ID NO:11:

( i ) SEQUENCE CHARACTERISTICS:
( A ) LENGTH: 47 amino acids
( B ) TYPE: amino acid
( D ) TOPOLOGY: linear ( i i ) MOLECULE TYPE: peptide ( x i ) SEQUENCE DESCRIPTION: SEQ ID NO:11:

Lys Lys Lys Gln Tyr Thr Ser Ile His His Gly Val Val Glu Val Asp
1 5 10 15

Ala Ala Val Thr Pro Glu Glu Arg His Leu Ser Lys Met Gln Gln Asn
20 25 30

Gly Tyr Glu Asn Pro Thr Tyr Lys Phe Phe Glu Gln Met Gln Asn
35 40 45

( 2 ) INFORMATION FOR SEQ ID NO:12:

( i ) SEQUENCE CHARACTERISTICS:
( A ) LENGTH: 197 amino acids ( B ) TYPE: amino acid
( D ) TOPOLOGY: linear ( i i ) MOLECULE TYPE: peptide ( x i ) SEQUENCE DESCRIPTION: SEQ ID NO:12:

```
Met Cys Ala Ala Leu Arg Arg Asn Leu Leu Leu Arg Ser Leu Trp Val
1               5                   10                  15

Val Leu Ala Ile Gly Thr Ala Gln Val Gln Ala Ala Ser Ser Pro Arg
            20                  25                  30

Trp Pro Gln Ile Ala Val Leu Cys Glu Ala Gly Gln Ile Tyr Gln Pro
        35                  40                  45

Gln Tyr Leu Ser Glu Glu Gly Arg Trp Val Thr Asp Leu Ser Lys Lys
    50                  55                  60

Thr Thr Gly Pro Thr Cys Leu Arg Asp Lys Met Asp Leu Asp Tyr Cys
65                  70                  75                  80

Lys Lys Ala Tyr Pro Asn Arg Asp Ile Thr Asn Ile Val Glu Ser Ser
                85                  90                  95

His Tyr Gln Lys Ile Gly Gly Trp Cys Arg Gln Gly Ala Leu Asn Ala
            100                 105                 110

Ala Lys Cys Lys Gly Ser His Arg Trp Ile Lys Pro Phe Arg Cys Leu
        115                 120                 125

Gly Pro Phe Gln Ser Asp Ala Leu Leu Tyr Pro Glu Gly Cys Leu Phe
    130                 135                 140

Asp His Ile His Asn Ala Ser Arg Cys Trp Pro Phe Val Arg Trp Asn
145                 150                 155                 160

Gln Thr Gly Ala Ala Ala Cys Gln Glu Arg Gly Met Gly Met Arg Thr
                165                 170                 175

Phe Ala Met Leu Leu Pro Cys Gly Ile Ser Val Phe Ser Gly Val Glu
            180                 185                 190

Phe Val Cys Cys Pro
        195
```

( 2 ) INFORMATION FOR SEQ ID NO:13:

( i ) SEQUENCE CHARACTERISTICS:
( A ) LENGTH: 166 amino acids
( B ) TYPE: amino acid
( D ) TOPOLOGY: linear ( i i ) MOLECULE TYPE: peptide ( x i ) SEQUENCE DESCRIPTION: SEQ ID NO:13:

```
Ser Gln Lys Arg Leu Glu Glu Ser His Arg Glu Lys Val Thr Arg Val
1               5                   10                  15

Met Lys Asp Trp Ser Asp Leu Glu Glu Lys Tyr Gln Asp Met Arg Leu
            20                  25                  30

Ala Asp Pro Lys Ala Ala Gln Ser Phe Lys Gln Arg Met Thr Ala Arg
        35                  40                  45

Phe Gln Thr Ser Val Gln Ala Leu Glu Glu Glu Gly Asn Ala Glu Lys
    50                  55                  60

His Gln Leu Ala Ala Met His Gln Gln Arg Val Leu Ala His Ile Asn
65                  70                  75                  80

Gln Arg Lys Arg Glu Ala Met Thr Cys Tyr Thr Gln Ala Leu Thr Glu
                85                  90                  95

Gln Pro Pro Asn Ala His His Val Glu Lys Cys Leu Gln Lys Ile Leu
            100                 105                 110
```

-continued

| | | | | | | | | | | | | | | | |
|---|---|---|---|---|---|---|---|---|---|---|---|---|---|---|---|
| Arg | Ala | Leu | His | Lys | Asp | Arg | Ala | His | Ala | Leu | Ala | His | Tyr | Arg | His |
| | | 115 | | | | | 120 | | | | | 125 | | | |
| Leu | Leu | Asn | Ser | Gly | Gly | Pro | Gly | Gly | Leu | Glu | Ala | Ala | Ala | Ser | Glu |
| | 130 | | | | | 135 | | | | | 140 | | | | |
| Arg | Pro | Arg | Thr | Leu | Glu | Arg | Leu | Ile | Asp | Ile | Asp | Arg | Ala | Val | Asn |
| 145 | | | | | 150 | | | | | 155 | | | | | 160 |
| Gln | Ser | Met | Thr | Met | Leu | | | | | | | | | | |
| | | | | 165 | | | | | | | | | | | |

(2) INFORMATION FOR SEQ ID NO:14:

(i) SEQUENCE CHARACTERISTICS:
(A) LENGTH: 53 amino acids
(B) TYPE: amino acid
(D) TOPOLOGY: linear (ii) MOLECULE TYPE: peptide (xi) SEQUENCE DESCRIPTION: SEQ ID NO:14:

| | | | | | | | | | | | | | | | |
|---|---|---|---|---|---|---|---|---|---|---|---|---|---|---|---|
| Lys | Trp | Arg | Thr | Ser | Arg | Ser | Pro | His | Ala | Gln | Gly | Phe | Ile | Glu | Val |
| 1 | | | | 5 | | | | | 10 | | | | | 15 | |
| Asp | Gln | Asn | Val | Thr | Thr | His | His | Pro | Ile | Val | Arg | Glu | Glu | Lys | Ile |
| | | | 20 | | | | | 25 | | | | | 30 | | |
| Val | Pro | Asn | Met | Gln | Ile | Asn | Gly | Tyr | Glu | Asn | Pro | Thr | Tyr | Lys | Tyr |
| | | 35 | | | | | 40 | | | | | 45 | | | |
| Phe | Glu | Val | Lys | Glu | | | | | | | | | | | |
| | 50 | | | | | | | | | | | | | | |

(2) INFORMATION FOR SEQ ID NO:15:

(i) SEQUENCE CHARACTERISTICS:
(A) LENGTH: 47 amino acids
(B) TYPE: amino acid
(D) TOPOLOGY: linear (ii) MOLECULE TYPE: peptide (xi) SEQUENCE DESCRIPTION: SEQ ID NO:15:

| | | | | | | | | | | | | | | | |
|---|---|---|---|---|---|---|---|---|---|---|---|---|---|---|---|
| Arg | Lys | Arg | Gln | Tyr | Gly | Thr | Ile | Ser | His | Gly | Ile | Val | Glu | Val | Asp |
| 1 | | | | 5 | | | | | 10 | | | | | 15 | |
| Pro | Met | Leu | Thr | Pro | Glu | Glu | Arg | His | Leu | Asn | Lys | Met | Gln | Asn | His |
| | | | 20 | | | | | 25 | | | | | 30 | | |
| Gly | Tyr | Glu | Asn | Pro | Thr | Tyr | Lys | Tyr | Leu | Glu | Gln | Met | Gln | Ile | |
| | | 35 | | | | | 40 | | | | | 45 | | | |

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

GCAACCGAAT GGACAGGGTA 20

(2) INFORMATION FOR SEQ ID NO:17:

(i) SEQUENCE CHARACTERISTICS:
(A) LENGTH: 21 base pairs
(B) TYPE: nucleic acid
(C) STRANDEDNESS: single
(D) TOPOLOGY: linear -continued ( i i ) MOLECULE TYPE: cDNA ( x i ) SEQUENCE DESCRIPTION: SEQ ID NO:17:

C A A G G C A G C C   A G G T A G T T C T   C   2 1

( 2 ) INFORMATION FOR SEQ ID NO:18:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:18:

G T A A A G A A G G   A A T G G G A A G A   G G C   2 3

( 2 ) INFORMATION FOR SEQ ID NO:19:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:19:

C C A T C C G A C G   G C G G T C A T T C   A G C   2 3

What is claimed is:

1. A recombinant amyloid precursor-like protein (APLP), human APLP2, comprising the amino acid sequence of FIG. 9 (SEQ ID NO:4).

2. A peptide of the formula QQLRELQRH (SEQ ID NO:1).

3. An immunogenic peptide fragment comprising the following polypeptide sequence, or subsequence thereof:

QQLRELQRH(SEQ ID NO:1)

said sequence, or said subsequence, being immunogenic so as to induce the production of active antibodies specific to APLP1 (SEQ ID NO:3).

4. The immunogenic peptide fragment of claim 3, coupled to an immunogenic carrier.

5. A recombinant amyloid precursor-like protein (APLP), mouse APLP1, comprising the amino acid sequence of FIG. 2 (SEQ ID NO:3).

* * * * *

UNITED STATES PATENT AND TRADEMARK OFFICE

CERTIFICATE OF CORRECTION

PATENT NO. : 5,891,991

DATED : April 6, 1999

INVENTORS : Wasco *et al.*

It is certified that an error appears in the above-identified patent and that said Letters Patent is hereby corrected as shown below.

On the Title Page, item [75] (Inventors), after "Wilma Wasco," please replace "Boston" with --Cambridge--.

On the face page, in item [75] (Inventors), after "Keith Bupp," please replace "Chalfont, Pa." with --Somerset, N.J.--.

On the face page, in item [75] (Inventors), after "Margaret Magendantz," please replace "Summerville" with --Somerville--.

On the face page, in item [75] (Inventors), after "Randolph Tanzi," please replace "Canton" with --Hull--.

Signed and Sealed this

Twenty-seventh Day of March, 2001

*Attest:*

Nicholas P. Godici

NICHOLAS P. GODICI

*Attesting Officer*

*Acting Director of the United States Patent and Trademark Office*